US008617534B2

(12) United States Patent
Sussman et al.

(10) Patent No.: US 8,617,534 B2
(45) Date of Patent: Dec. 31, 2013

(54) COMPOSITIONS AND METHOD FOR MANIPULATING PIM-1 ACTIVITY IN CIRCULATORY SYSTEM CELLS

(75) Inventors: Mark A. Sussman, San Diego, CA (US); John A. Muraski, San Clemente, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 419 days.

(21) Appl. No.: 12/742,871

(22) PCT Filed: Nov. 14, 2008

(86) PCT No.: PCT/US2008/083693
§ 371 (c)(1),
(2), (4) Date: Jul. 21, 2010

(87) PCT Pub. No.: WO2009/065080
PCT Pub. Date: May 22, 2009

(65) Prior Publication Data
US 2010/0316701 A1 Dec. 16, 2010

Related U.S. Application Data

(60) Provisional application No. 61/091,698, filed on Aug. 25, 2008, provisional application No. 60/988,753, filed on Nov. 16, 2007.

(51) Int. Cl.
*A61K 48/00* (2006.01)
*C12N 15/63* (2006.01)
*A61K 31/70* (2006.01)

(52) U.S. Cl.
USPC ............. 424/93.21; 435/455; 435/320.1

(58) Field of Classification Search
USPC ................ 424/93.21; 435/455, 320.1
See application file for complete search history.

(56) References Cited

U.S. PATENT DOCUMENTS

| | | | | |
|---|---|---|---|---|
| 2002/0076395 A1* | 6/2002 | Crystal et al. | ............ | 424/93.2 |
| 2004/0258669 A1* | 12/2004 | Dzau et al. | ............ | 424/93.21 |
| 2007/0031899 A1* | 2/2007 | Kobayashi et al. | ......... | 435/7.23 |
| 2008/0267921 A1* | 10/2008 | Marban et al. | ............. | 424/93.7 |
| 2012/0128631 A1 | 5/2012 | Sussman | | |

OTHER PUBLICATIONS

Muraski et al. Pim-1 regulates cardiomyocyte survival downstream of Akt. Abstract #1523 in Circulation 114 (18, Suppl. S): p. 11-294, Oct. 31 2006.*
Cottage, C et al. Pim-1 stimulates cardiac progenitor cell proliferation and asymmetric division. Circulation 118 (18, Suppl. 2): p. S321, Abstract No. 1414, 2008).*
Aho et al., "Pim-1 kinase promotes inactivation of the pro-apoptotic Bad protein by phosphorylating it on the Ser112 gatekeeper site", FEBS Letter 571 (2004) 43-49.

Bachmann, "The serine/threonine kinase Pim-1", The International Journal of Biochemistry & Cell Biology 37 (2005) 726-730.
Bhattacharya, "Pim-1 associates with protein complexes necessary for mitosis", Chromosoma (2002) 111:80-95.
Camper-Kirby, "Myocardial Akt Activation and Gender: Increased Nuclear Activity in Females Versus Males", Circulation Research (2001), 88:1020-1027.
Fransioli, "Evolution of the c-kit-Positive Cell Respons to Pathological Challenge in the Myocardium", Stem Cells (2008) 26:1315-1324.
Gude, "Akt Promotes Increased Cardiomyocyte Cycling and Expansion of the Cardiac Progenitor Cell Population", Circulation Research (2006) 99:381-388.
Hammerman, "Pim and Akt oncogenes are independent regulators of hematopoietic cell growth and survival", (2005) 105:4477-4483.
Katakami, "Role of Pim-1 in Smooth Muscle Cell Proliferation", The Journal of Biological Chemistry, vol. 279, No. 52, Issue of Dec. 24, pp. 54742-54749, 2004.
Kato, "Atrial natriuretic peptide promotes cardiomyocyte survival by cGMP-dependent nuclear accumulation of zyxin and Akt", The Journal of Clinical Investigation, vol. 115, No. 10, Oct. 2005, pp. 2716-2730.
Lily, "The PIM-1 serine kinase prolongs survival and inhibits apoptosis-related mitochondrial dysfunction in part through a bcl-2-dependent pathway", Oncogene (1999) 18, 4022-4031.
Macdonald, "Pim kinases phosphorylate multiple sites on Bad and promote 14-3-3 binding and dissociation from Bcl-XL", BMC Cell Biology (2006) 7:1, pp. 1-14.
Mikkers, "Mice Deficient for All PIM Kineses Display Reduced Body Size and Impaired Responses to Hematopoietic Growth Factors", Mol. Cell Biol. 2004, 24(13):6104-6115.
Muraski, "Pim-1 regulates cardiomyocyte survival downstream of Akt", Nature Medicine, vol. 13, No. 12, Oct. 2007, pp. 1467-1475.
Plank, "Calcium dynamics in the failing heart: restoration by β-adrenergic receptor blockade"; Am. J. Physiol. Heart Circ. Physiol. 285: H305-H315, 2003.
Roh, "Overexpression of the Oncogenic Kinase Pim-1 Leads to Genomic Instability", Cancer Res. (2003) 63:8079-8084.
Rota, "Nuclear Targeting of Akt Enhances Ventricular Function and Myxocyte Contractility", Circ. Res. (2005) 97:1332-1341.
Shiraishi, "Nuclear Targeting of Akt Enhances Kinase Activity and Survival of Cardiomyocytes", Circ. Res. (2004) 94:884-891.
Solarogu, "Anti-Apoptotic Effect of Granulocyte-Colony Stimulating Factor After Focal Cerebral Ischemia in the Rat", Neuroscience 143 (2006) 965-974.
Sussman, "Myocardial Aging and Senescence: Where Have the Stem Cells Gone?", Annu. Rev. Physiol. (2004) 66:29-48.
Sussman, "Myofibril Degeneration Caused by Tropomodulin Overexpression Leads to Dilated Cardiomyopathy in Juvenile Mice", J. Clin. Invest., vol. 101, No. 1, Jan. 1998, 51-61.

(Continued)

*Primary Examiner* — Quang Nguyen
(74) *Attorney, Agent, or Firm* — Gregory P. Einhorn; Gavrilovich, Dodd & Lindsey LLP

(57) ABSTRACT

The invention provides compositions (e.g., pharmaceutical compositions) comprising nucleic acids encoding the serine/threonine kinase PIM-1, and methods for making and using them; including methods for inducing cellular proliferation, and protecting cardiac cells from hypoxia and cellular apoptosis. The invention provides compositions (e.g., pharmaceutical compositions) comprising nucleic acids encoding PIM-1, and methods for enhancing the regenerative potential of stem cells in the heart.

8 Claims, 21 Drawing Sheets

(56) References Cited

OTHER PUBLICATIONS

Tsujita, "Evaluation of Left Ventricular Function in Cardiomyopathic Mice by Tissue Doppler and Color M-Mode Doppler Echocardiography", Echocardiography. A. Jrnl. of CV Ultrasound & Allied Tech., vol. 22, No. 3, 2005, pp. 245-253.

Tsujita, "Nuclear targeting of Akt antagonizes aspects of cardiomyocyte hypertrophy", PNAS, Aug. 8, 2006, vol. 103, No, 32. 11946-11951.

Wang, "Pim-1: A serine/threonine kinase with a role in cell survival, proliferation, differentiation and tumorigenesis", J. Vet. Sci. (2001), 2(3), 167-179.

Welch, "Cardiac-Specific IGF-1 Expression Attenuates Dilated Cardiomyopathy in Tropomodulin-Overexpressing Transgenic Mice", Circ. Res. (2002) 90:641-648.

Yan, "The PIM-2 Kinase Phosphorylates BAD on Serine 112 and Reverses BAD-induced Cell Death", The Journal of Biological Chemistry, vol. 278, No. 46, Issue of Nov. 14, pp. 45358-45367, 2003.

Fox et al., "The serine/threonine kinase Pim-2 is a transcriptionally regulated apoptotic inhibitor," Genes Dev. 2003 17:1841-1854.

Fischer, et al., "Cardiac Progenitor Cell Commitment is Inhibited by Nuclear Akt Expression," Circulation Research, 2011; 108:960-970.

Sussman, et al., "Pathogenesis of dilated cardiomyopathy: molecular, structural, and population analyses in tropomodulin-overexpressing transgenic mice", Am J Pathol. Dec 1999;155(6):2101-13.

Fischer et al., "Enhancement of Myocardial Regeneration Through Genetic Engineering of Cardiac Progenitor Cells Expressing Pim-1 Kinase", Circulation 2009, 120:2077-2087.

Gnecchi et al., "Paracrine action accounts for marked protection of ischemic heart by Akt-modified mesenchymal stern cells", Nature Medicine, vol. 11, No. 4, Apr. 2005, pp. 367-368.

Gnecchi et al., "Evidence supporting paracrine hypothesis for Akt-modified mesenchymal stem cell-mediated cardiac protection and functional improvement", The FASEB Journal, vol. 20, Apr. 2006, pp. 661-669.

Mangi et al., "Mesenchymal stem cells modified with Akt prevent remodeling and restore performance of infarcted hearts", Nature Medicine, vol. 9, No. 9, Sep. 2003, pp. 1195-1201.

Mirotsou et al., "Secreted frizzled related protein 2 (Sfrp2) is the key Akt-mesenchymal stem cell-released paracrine factor mediating myocardial survival and repair", PNAS, Jan. 30, 2007, vol. 104, No. 5, pp. 1643-1648.

Mohsin et al., "Human Cardiac Progenitor Cells Engineered with Pim-I Kinase Enhance Myocardial Repair", Journal of the American College of Cardiology, vol. 60, No. 14, 2012, pp. 1278-1287.

Noiseux et al., "Mesenchymal Stemn Cells Overexpressing Akt Dramatically Repair Infarcted Myocardium and Improve Cardiac Function Despite Infrequent Cellular Fusion or Differentiation", Molecular Therapy, vol. 14, No. 6, Dec. 2006. pp. 840-850.

\* cited by examiner

COMPOSITIONS AND METHOD FOR MANIPULATING PIM-1 ACTIVITY IN CIRCULATORY SYSTEM CELLS

CROSS-REFERENCE TO RELATED APPLICATIONS

This United States utility patent application is the §371 national phase of PCT international patent application no. PCT/US2008/083693, having an international filing date of Nov. 14, 2008, which claims benefit of priority to U.S. Provisional Patent Application Ser. No. 61/091,698, filed Aug. 25, 2008; and U.S. Ser. No. 60/988,753, filed Nov. 16, 2007. The aforementioned applications are expressly incorporated herein by reference in their entirety and for all purposes.

FEDERAL FUNDING

This invention was produced in part using funds from the Federal government under one or more of the following grants 5R01HL067245, 1R01HL091102, 1P01HL085577, and 1P01AG023071, all from the National Institutes of Health. Accordingly, the Federal government has certain rights in this invention.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 475442002940Seqlist.txt | Nov. 10, 2008 | 10,066 bytes |

TECHNICAL FIELD

This invention generally relates to cell and molecular biology, treatment or prevention of cardiac disease or injury, and regenerative medicine. Disclosed are compositions (e.g., pharmaceutical compositions) comprising nucleic acids encoding the serine/threonine kinase PIM-1 (and related PIM enzymes), and medical uses and methods relating to alteration of PIM availability or availability in cardiac or vascular system cells or tissues; including inducing or enhancing differentiation, implantation, survival, and function of stem cells, progenitor cells, or adult cells in a cardiac or vascular tissue or environment. Also disclosed are compositions comprising nucleic acids encoding PIM, and methods for enhancing the regenerative potential of stem cells and progenitor cells in a vascular or cardiac environment.

BACKGROUND

Intracellular molecular signaling networks communicate via kinases that phosphorylate target substrates to regulate critical aspects of growth and survival. PIM-1, a proto-oncogenic serine/threonine kinase, was originally discovered as the proviral integration site for Moloney murine Leukemia virus. PIM-1 is up-regulated in prostate cancer. The gene is highly expressed in the liver and spleen during fetal hematopoiesis and primarily in B-lymphoid and myeloid cell lines.

PIM-1 exists in two isoforms with molecular weights of 34 and 44 kDa. The 34 kDa isoform is cytosolic and nuclear localized, while the 44 kDa isoform was recently found to be membrane bound. PIM-1 may be a relatively promiscuous kinase based upon minimal target substrate recognition sequence requirements and capacity for autophosphorylation. Two additional family members, PIM-2 and PIM-3, may exhibit functional redundancy with PIM-1.

Induction of PIM-1 expression is mediated by cytokines and growth factors including LIF, GM-CSF, EGF, and most interleukins, consistent with a role for PIM-1 in proliferation and survival of hematopoeitic cells. PIM-1 mediates proliferative actions through phosphorylation of multiple target substrates, resulting in cell cycle transition, as well as protective effects via phosphorylation of multiple targets. Induction of PIM-1 expression has been linked to AKT (a serine/threonine kinase) in hematopoeitic cells.

SUMMARY

The invention provides compositions, such as pharmaceutical compositions, comprising nucleic acids encoding a serine/threonine kinase PIM, and methods for making and using them; including methods for inducing cardiac or vascular cellular proliferation, and protecting cardiac or vascular cells from hypoxia and cellular apoptosis. In one aspect, the compositions and methods of the invention are used to express PIM-1 (e.g., by upregulating PIM kinase expression and/or activity) to protect cardiomyocytes from hypertrophy and inhibit myocardial apoptosis induced by infarction, reducing infarct size. In another embodiment, the compositions and methods of the invention are used to express PIM to induce cardiac or vascular cellular dedifferentiation and re-expression of stem cell markers; and in one aspect, to over-express PIM to enhance the regenerative potential of stem cells, including stem cell ability to engraft in the heart after a myocardial infarction (post-MI).

One aspect of the disclosure relates to a method, comprising identifying a patient in need of enhanced PIM activity in a vascular system tissue, and enhancing levels of PIM in vascular system tissue of the patient to alter a functional characteristic of cells in that tissue. In one embodiment, the patient has experienced cardiac injury and the enhanced PIM levels facilitate cardiac regeneration to repair that injury. The enhancing step may advantageously comprise enhancing endogenous production of PIM in the vascular system tissue. Alternatively, it may comprise administering to the patient an exogenous PIM. The exogenous PIM may comprise PIM-1, for example, or another material sharing that same function, and may comprise a PIM enzyme in association with a cellular delivery moiety, such as a translocation domain that is attached to the PIM enzyme. In yet another embodiment, the enhancing step comprises administering cells to the patient that produce enhanced levels of PIM. As examples, the administered cells may be stem cells or vascular system progenitor cells. Advantageously, the administered cells comprise a PIM-encoding polynucleotide operatively linked to a non-PIM promoter.

In one embodiment, the enhancing step comprises administering cells to vascular tissue of the patient, and expressing enhanced levels of PIM from the administered cells.

A different embodiment comprises PIM-delivering or enhancing material for treatment of vascular system disease or injury. This material can be, for example, a PIM enzyme linked to a cellular delivery agent, or a cell for introduction into a human or animal, wherein the cell has been altered to permit enhanced production of PIM. In some cases, the cell is a progenitor cell or a stem cell, and the alteration comprises a PIM-encoding polynucleotide under control of a non-PIM promoter. Advantageously, the promoter may be a cardiac-specific promoter, an inducible promoter, an endogenous promoter, an exogenous promoter, or a constituitive promoter. Alternatively, the PIM-enhancer may be an inducer of endogenous PIM expression.

Yet another embodiment is use of a PIM-delivering or enhancing material in the preparation of a medicament for treating vascular system disease or injury.

Still another embodiment is a composition, comprising a vascular system cell or a cell that is differentiatable into a vascular system cell, where the cell comprises a PIM-encoding polynucleotide sequence operably linked to a non-PIM promoter. The cell may be, for example, a stem cell or cardiac progenitor cell. Various types of stem cells that are contemplated include mesenchymal stem cells, cardiac stem cells, adipose-derived stem cells, embryonic stem cells, and hematopoietic stem cells. Advantageously, the promoter is an inducible promoter or a cardiac-specific promoter.

Yet another embodiment is a method for treating cardiac disease or injury, comprising enhancing levels of PIM within diseased or injured cardiac tissue. The cardiac disease or injury may include ischemic injury, hypoxic injury, myocardial infarction, traumatic cardiac injury, cardiac hypertrophy, overpressure injury, congestive heart failure, apoptosis-inducing injury or disease, bacterial infection, viral infection, and conditions that create an enhanced risk of any of the foregoing.

Another embodiment provides pharmaceutical composition formulated for administration to heart muscle comprising:

(i) (a) a PIM-1 encoding nucleic acid;

(b) a PIM-1 encoding nucleic acid inserted in an expression construct or expression vehicle, or a naked PIM-1 encoding nucleic acid operably linked to a promoter;

(c) the pharmaceutical composition of (b), wherein the expression construct or expression vehicle comprises or consists of a vector, a plasmid, a recombinant virus or an artificial chromosome;

(d) the pharmaceutical composition of (c), wherein the expression construct or expression vehicle comprises or consists of a recombinant adeno-associated viral vector; an adenovirus vector, a retroviral vector; or a lentiviral vector;

(e) the pharmaceutical composition of (d), wherein the expression construct or expression vehicle comprises or consists of an immunodeficiency virus derived vector;

(f) the pharmaceutical composition of (e), wherein the immunodeficiency virus derived vector comprises or consists of a human immunodeficiency virus (HIV) derived vector; or (g) the pharmaceutical composition of (f), wherein the human immunodeficiency virus (HIV) derived vector comprises or consists of a human immunodeficiency virus-1 (HIV-1) derived vector;

(h) the pharmaceutical composition of any of (a) to (g), wherein the PIM-1 encoding nucleic acid is operably linked to a promoter;

(i) the pharmaceutical composition of (h), wherein the promoter is a constitutive or an inducible promoter; or (j) the pharmaceutical composition of (i), wherein the promoter is constitutively or inducibly active in a heart cell (a myocyte); and, (ii) a pharmaceutically acceptable excipient.

wherein the pharmaceutical composition formulated for administration to heart muscle.

Also contemplated are liposomes comprising a pharmaceutical compound of the invention; and/or nanoparticles comprising a pharmaceutical compound of the invention.

Still other embodiments include uses of a pharmaceutical compound of the invention, a liposome of the invention, or a nanoparticle of the invention, for the manufacture of a medicament for:

(a) the amelioration, treatment or prevention of cellular apoptosis and/or damage in a cardiac or vascular cell, tissue or organ subsequent to cellular, tissue and/or organ hypoxia, hypoxaemia or anoxia, or subsequent to pressure-overload induced hypertrophy or heart failure, by increasing PIM-1 kinase activity in the cardiac or vascular cell, tissue or organ;

(b) the use of (a), wherein the hypoxia, hypoxaemia or anoxia is caused by an infarction, trauma, surgery, reimplantation, transplantation or a toxin;

(c) inducing cellular dedifferentiation and/or re-expression of a stem cell marker in a cardiac or vascular cell, tissue or organ;

(d) enhancing the retention of engrafted or transplanted cells, tissues or organs by overexpressing or expressing PIM-1 in the cells, tissues or organs;

(e) increasing the expression of bcl-2, bcl-XL and/or phosphorylation of Bad protein in a cardiac or vascular cell, tissue or organ;

(f) the amelioration, treatment or prevention of ischemia reperfusion injury in a cardiac or vascular cell, tissue or organ;

(g) the use of any of (a) to (f), wherein the cardiac or vascular cell, tissue or organ is or is contained in: a heart cell (a myocyte), a heart tissue or a heart or other organ;

(h) overexpressing or expressing PIM-1 in a stem cell or a pluripotent cell to enhance the regenerative potential and/or induce proliferation of the stem cell or pluripotent cell;

(i) overexpressing or expressing PIM-1 in a heart cell (a myocyte) or heart tissue to increase Bcl-XL expression in the heart cell (myocyte) or heart tissue to induce cardioprotective anti-apoptotic signaling and/or to increase myocardial survival signaling;

(j) the use of any of (a) to (i), wherein the cell is a stem cell, an adult stem cell, a hematopoietic stem cell, an adipose-derived stem cell, a mesenchymal stem cell, a c-kit$^+$ stem cell, a human stem cell, an autologous or allogeneic stem cell, an embryonic cell, a tissue-specific resident stem cell, an allogeneic or autologous cell, a progenitor cell, a placental and/or cord blood cell, a Sca-1+ cell, or a CD34+ cell; or (k) the use of any of (a) to (j), wherein the use is for the amelioration, treatment or prevention of cellular apoptosis and/or damage in a cardiac or vascular cell, tissue or organ subsequent to cellular, tissue and/or organ hypoxia, hypoxaemia or anoxia, or subsequent to pressure-overload induced hypertrophy or heart failure; or because of a hypertrophic myocardium, an aged myocardium, a failing myocardium, an ischemic myocardium, a remodeled myocardium, a myocardium damaged by inflammation, infection, chronic stress, disease, diabetes or alcoholism; and/or oxidative damage.

Also included are methods for inducing, upregulating or inserting a PIM-1 nucleic acid or a PIM-1 kinase activity in a cardiac or vascular cell, tissue or organ, comprising:

(a) (i) providing a PIM-1 encoding nucleic acid; and inserting the PIM-1 encoding nucleic acid into the cardiac or vascular cell, tissue or organ; (ii) providing a cell expressing and/or secreting a PIM-1 kinase; (iii) administering PIM-1 kinase or a PIM-1 expressing nucleic acid to the cardiac or vascular cell, tissue or organ; or, (iv) providing a compound that induces or upregulates PIM-1 nucleic acid or a PIM-1 kinase activity in a cardiac or vascular cell, tissue or organ;

(b) the method of (a), wherein the PIM-1 encoding nucleic acid comprises or consists of a PIM-1 encoding message (a PIM-1 encoding mRNA), or a PIM-1 gene;

(c) the method of (a) or (b), wherein the PIM-1 encoding nucleic acid comprises or consists of a human PIM-1 encoding nucleic acid, or a human PIM-1 encoding message (mRNA), or a human PIM-1 gene, or a human PIM-1 gene locus;

(d) the method of any of (a) to (c), wherein the cell is a human cell, a stem cell, an adult stem cell, a hematopoietic stem cell, an adipose-derived stem cell, a mesenchymal stem cell, a c-kit$^+$ stem cell, a human stem cell, an autologous or allogeneic stem cell, an embryonic cell, a tissue-specific resident stem cell, an allogeneic or autologous cell, a progenitor cell, a placental and/or cord blood cell, a Sca-1+ cell, or a CD34+ cell;

(e) the method of any of (a) to (d), wherein the PIM-1 encoding nucleic acid is inserted into a cardiac or vascular cell, tissue or organ ex vivo or in vivo;

(f) the method of any of (a) to (e), wherein a PIM-1 encoding nucleic acid is inserted in an expression construct or expression vehicle;

(g) the method of any of (f), wherein the expression construct or expression vehicle comprises or consists of a vector, a plasmid, a recombinant virus or an artificial chromosome;

(h) the method of any of (g), wherein the expression construct or expression vehicle comprises or consists of a recombinant adeno-associated viral vector; an adenovirus vector, a retroviral vector; or a lentiviral vector;

(i) the method of any of (h), wherein the expression construct or expression vehicle comprises or consists of an immunodeficiency virus derived vector;

(j) the method of any of (i), wherein the immunodeficiency virus derived vector comprises or consists of a human immunodeficiency virus (HIV) derived vector;

(k) the method of any of (j), wherein the human immunodeficiency virus (HIV) derived vector comprises or consists of a human immunodeficiency virus-1 (HIV-1) derived vector;

(l) the method of any of (a) to (k), wherein the PIM-1 encoding nucleic acid is inserted into a cell that does not express wild type (normal) levels of PIM-1 protein;

(m) the method of (l), wherein the PIM-1 encoding nucleic acid is inserted into a cell that does not express wild type (normal) levels of PIM-1 protein-encoding message (mRNA);

(n) the method of (m), wherein the PIM-1 encoding nucleic acid is inserted into a cell that does not comprise a wild type (normal) PIM-1 gene or genomic PIM-1 encoding nucleic acid;

(o) the method of any of (a) to (n), wherein the PIM-1 encoding nucleic acid is inserted into a cardiac or vascular cell, tissue or organ ex vivo and the cardiac or vascular cell, tissue or organ is implanted into an individual in need thereof;

(p) the method of any of (a) to (o), wherein the PIM-1 encoding nucleic acid is inserted into a heart cell, cardiac or vascular tissue or cardiac or vascular organ or a myocyte cell ex vivo and the cell is implanted into a cardiac or vascular cell, tissue or organ or a myocardium (a heart) in need thereof;

(q) the method of any of (a) to (n), wherein the PIM-1 encoding nucleic acid is in vivo inserted into a cardiac or vascular cell, tissue or organ in an individual in need thereof;

(r) the method of (q), wherein the PIM-1 encoding nucleic acid is inserted into a cardiac or vascular cell, tissue or organ or a heart cell or a myocyte cell or a heart in vivo;

(s) the method of (r), wherein the individual has congestive heart failure, or has had a myocardial infarction, or heart muscle damage;

(t) the method of any of (a) to (s), wherein the cardiac or vascular cell, tissue or organ is or is contained in: a heart cell (a myocyte), a heart tissue or a heart or other organ;

(u) the method of (a), wherein the compound that induces or upregulates PIM-1 nucleic acid or a PIM-1 kinase activity in a cardiac or vascular cell, tissue or organ comprises: an interleukin, a cytokine and/or a paracrine factor involved in survival and/or proliferative signaling; an up-regulator of AKT serine/threonine kinase; insulin-like growth factor-1 (IGF-1); insulin; leukemia inhibitory factor (LIF); granulocyte-macrophage colony-stimulating factor (GM-CSF); or epidermal growth factor (EGF);

(v) the method of any of (a) to (u), wherein the wherein PIM-1 activity in the cardiac or vascular cell, tissue or organ is increased by administering an exogenous PIM-1 kinase to the population of cells;

(w) the method of (v), wherein PIM-1 activity is increased by contacting a population of cells with a transfected cell that expresses an exogenous PIM-1 gene;

(x) the method of (v), wherein the population of cells comprises stem cells; or (y) the method of any of (a) to (y), wherein the PIM-1 kinase activity is increased and/or upregulated in the cardiac or vascular cell, tissue or organ by administering a pharmaceutical compound of the invention, a liposome of the invention, or a nanoparticle of the invention, or any combination thereof.

Still other aspects include methods for treating, preventing or ameliorating a disease or condition comprising administering to an individual in need thereof a pharmaceutical compound of the invention, a liposome of the invention, or a nanoparticle of the invention, or any combination thereof, wherein the treatment, prevention and/or amelioration of the disease or condition comprises:

(a) the amelioration, treatment or prevention of cellular apoptosis and/or damage in a cardiac or vascular cell, tissue or organ subsequent to cellular, tissue and/or organ hypoxia, hypoxaemia or anoxia, or subsequent to pressure-overload induced hypertrophy or heart failure; or because of a hypertrophic myocardium, an aged myocardium, a failing myocardium, an ischemic myocardium, a remodeled myocardium, a myocardium damaged by inflammation, infection, chronic stress, disease, diabetes or alcoholism; and/or oxidative damage, by increasing or upregulating PIM-1 kinase activity in the cardiac or vascular cell, tissue or organ;

(b) the method of (a), wherein the cellular apoptosis and/or damage, or the hypoxia, hypoxaemia or anoxia, is caused by an infarction, trauma, surgery, reimplantation, transplantation or a toxin, or by inflammation, infection, chronic stress, diabetes or alcoholism; and/or oxidative damage;

(c) inducing cellular dedifferentiation and/or re-expression of a stem cell marker in a cardiac or vascular cell, tissue or organ;

(d) enhancing the retention of engrafted or transplanted cells, tissues or organs by overexpressing or expressing PIM-1 in the cells, tissues or organs;

(e) increasing the expression of bcl-2, bcl-XL and/or phosphorylation of Bad protein in a cardiac or vascular cell, tissue or organ;

(f) the amelioration, treatment or prevention of ischemia reperfusion injury in a cardiac or vascular cell, tissue or organ;

(g) the method of any of (a) to (f), wherein the cardiac or vascular cell, tissue or organ is or is contained in: a heart cell (a myocyte), a heart tissue or a heart or other organ;

(h) overexpressing or expressing PIM-1 in a stem cell or a pluripotent cell to enhance the regenerative potential and/or induce proliferation of the stem cell or pluripotent cell; or (i) overexpressing or expressing PIM-1 in a heart cell (a myocyte) or heart tissue to increase Bcl-XL expression in the heart cell (myocyte) or heart tissue to induce cardioprotective anti-apoptotic signaling and/or to increase myocardial survival signaling.

(j) the method of any of (a) to (i), wherein the cell is a stem cell, an adult stem cell, a hematopoietic stem cell, an adipose-derived stem cell, a mesenchymal stem cell, a c-kit+ stem cell, a human stem cell, an autologous or allogeneic stem cell, an embryonic cell, a tissue-specific resident stem cell, an allogeneic or autologous cell, a progenitor cell, a placental and/or cord blood cell, a Sca-1+ cell, or a CD34+ cell.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 6 graphically summarizes that non-infected cells (NI) or GFP-expressing cells show comparable TUNEL labeling following doxorubicin treatment, whereas Pimwt expressing cells show significant reductions of TUNEL positive nuclei ($p<0.05$); and FIG. 7 illustrates a micrograph demonstrating that cells expressing the DN construct show enhanced TUNEL labeling; while FIG. 6 shows quantitative results, the FIG. 7 panels illustrate representative fields of infected cardiomyocytes showing GFP fluorescence (green) overlay with actin filaments revealed by phalloidin (red) in GFP only, GFP-Pim-wt and GFP-Pim-DN samples, as described in detail in Example 2, below.

FIG. 9(A) illustrates a confocal microscopy of cultured cardiomyocytes infected with adenoviruses expressing nuclear-targeted β-galactosidase (B-gal), Akt wild-type (Akt wt), or nuclear targeted Akt (Akt-nuc) detected with myc-tag antibody (Tag); FIG. 9(B) illustrates an immunoblot blot showing increased Pim-1 expression in cardiomyocyte cells infected with adenovirus encoding nuclear-targeted Akt (Akt-nuc), as described in detail in Example 2, below.

FIG. 11 left panel illustrates a PCR of genomic DNA samples from Pim-1 transgenic mice, and FIG. 11 right panel illustrates an immunoblot of cardiac lysates, as described in detail in Example 2, below.

FIG. 12a and FIG. 12b graphically illustrate echocardiographic measurement of posterior (12a) and anterior (12b) wall dimension (PWD and AWD respectively) in NTG and Pim-DN animals at two week intervals; FIG. 12c graphically illustrates heart weight to body weight ratios in NTG and Pim-DN animals at 10 and 22 weeks of age; FIG. 12d graphically illustrates histogram data representing counts of TUNEL positive myocytes per $mm^2$ in 17-22 week old NTG and Pim-DN transgenics, as described in detail in Example 3, below.

FIGS. 14a to 14f illustrate line graphs representing weekly echo-cardiographic assessment of NTG and Pim-wt sham and TAC banded hearts for anterior wall dimension (AWD 14d, 14a), posterior wall dimension (PWD 14d, 14b), end diastolic dimension (EDD, 14c), end-systolic dimension (ESD, 14d), percent fractional shortening (FS, 14e), and ejection fraction (EF, 14f), as described in detail in Example 3, below.

FIG. 15a, FIG. 15b and FIG. 1c show in vivo hemodynamic assessment of NTG and Pim-wt hearts 4 and 10 weeks after sham or TAC operation, as described in detail in Example 3, below.

FIG. 16a graphically illustrates a histogram representing infarct size 7 days post-MI as a percent of left-ventricular free wall in Pim-KO hearts; FIG. 16b graphically illustrates data showing the number of TUNEL positive myocytes per $mm^2$ 7 days post-MI in Pim-KO hearts; FIG. 16c graphically illustrates in vivo hemodynamic measurements of NTG and Pim-KO mice 5 days following MI; FIG. 16e graphically illustrates immunoblot quantitation of survival protein levels 7 days post-infarction in Pim-KO and NTG control hearts; FIG. 16f graphically illustrates infarct size measurements 10 days post-infarction;

FIG. 16g graphically illustrates the number of TUNEL-labeled CM/m2 in LV 10 days after MI, as described in detail in Example 3, below.

FIG. 17A illustrates a cell growth assessment using trypan blue assay of control, CGW, and CGW-Pim-wt transduced CPCs; FIG. 17B illustrates an MTT assay on control, CGW, CGW-Pim-wt transduced CPCs; FIG. 17C illustrates the proliferation rate of Pim-1 expressing CPC's treated with or without 10 uM of Quercetagentin, a specific Pim-1 activity inhibitor, as described in detail in Example 4, below.

FIGS. 18A-C graphically illustrate electro-cardiographic assessment of AWD (FIG. 18A), EF (FIG. 18B), and FS (FIG. 18C), in sham (■), PBS injected (●), CGW (▲), and CGW-Pim-WT (♦) cardiac progenitor cells; FIG. 18D-F graphically illustrates in vivo hemodynamic measurements of left ventricular developed pressure (LVDP) (FIG. 18D), left ventricular end diastolic pressure (LVEDP) (FIG. 18E), and dP/dT maximum and minimum (FIG. 18F) were used to assess cardiac function 12 weeks post-intramyo-cardial injection of PBS, eGFP, and Pim-1 expressing CPCs, as described in detail in Example 4, below.

FIG. 20A-C illustrates electrocardiographic assessment of FS (FIG. 20A), EF (FIG. 20B), and AWD (FIG. 20C), in sham (■), PBS injected (●), CGW (▲), and CGW-Pim-WT (♦) cardiac progenitor cells 32 weeks post CPC transplantation, as described in detail in Example 4, below.

Like reference symbols in the various drawings indicate like elements.

DETAILED DESCRIPTION

Figure 1:
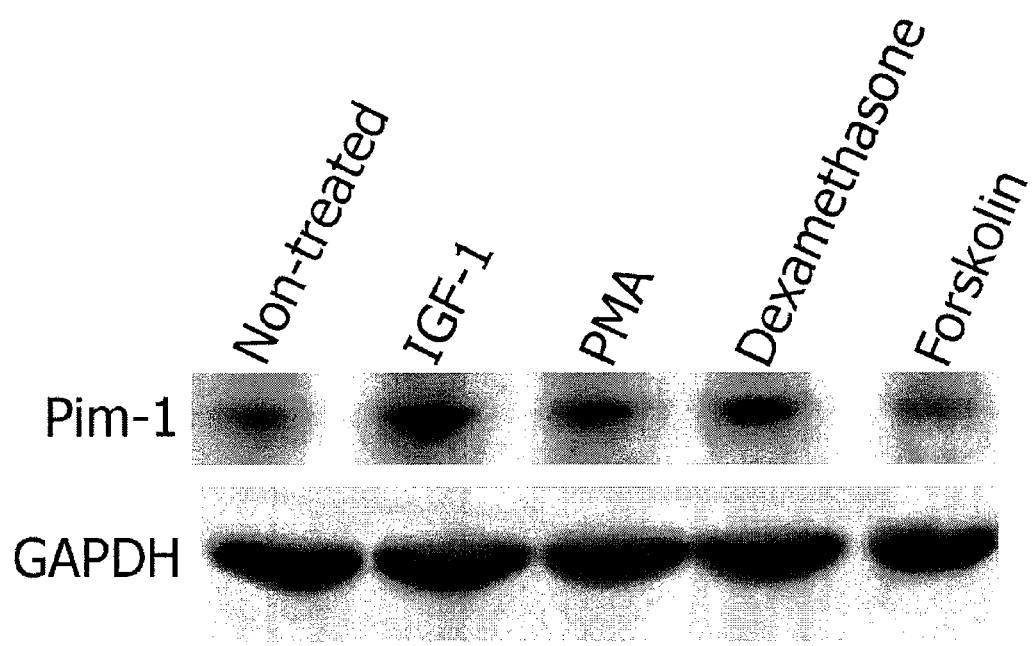
FIG. 1 illustrates immunoblots demonstrating that cardioprotective stimuli induces Pim-1 expression, as described in detail in Example 2, below.

The present disclosure includes the discovery of new roles for PIM-1, its isoforms, and other PIM enzymes having equivalent or overlapping targets and substrates. Specifically, these enzymes have a role in cardiac and other circulatory system protection, survival, repair, regeneration, and recovery, and in the implantation, differentiation, function, and survival of stem cells, progenitor cells, or differentiated cells introduced into circulatory system tissues. These discoveries form the basis for new cardiac therapies, including repair of damaged heart tissue and implantation, expansion, and survival of implanted stem cells or progenitor cells that differentiate into functional heart tissue. Prior to this invention, enhancement of PIM activity was not known to have any prophylactic or therapeutic utility in heart tissue, heart cells, or in other circulatory system cells or tissues.

We show that circulatory system disease or injury can be attenuated, halted, prevented, or reversed, and that damaged circulatory system tissue can be replaced, repaired, or regenerated, by enhancement of PIM activity in that tissue. Ways in which PIM activity can be enhanced are described in more detail below, but include upregulation of endogenous PIM production, direct introduction of materials having PIM activity into tissues or cells, introduction of polynucleotide encoding a PIM material into existing cells of a human or animal, removing cells from a subject and altering those cells to express enhanced levels of PIM, then reintroducing the cells into the subject, introducing exogenous cells into the subject that have been engineered to produce enhanced levels of PIM, including stem cells or progenitor cells that include a PIM-encoding polynucleotide under the control of a non-PIM promoter, including an inducible promoter, a constituitive promoter, or a cardiac-specific promoter.

The term "PIM" is used herein to refer to a serine or threonine kinase, including the various PIM enzymes, e.g., PIM-1, PIM-2, and PIM-3, further including any isoforms thereof. For example, the serine/threonine kinase PIM-1 is known to exist in two isoforms, and references to PIM and PIM-1 herein are intended to encompass both isoforms, unless otherwise specified. In addition, although certain cells, constructs, polynucleotides, techniques, uses, and methods are described in connection with one particular PIM, such as PIM-1, such descriptions are exemplary, and should be taken as also including the other PIM enzymes having similar activity.

The term "PIM activity" and "PIM kinase activity" refer to the enzymatic or physiological activity of the PIM enzymes, e.g., the activity of a PIM-1, and encompasses use of other materials having similar activity. The discoveries set forth herein relate to altering characteristics of living cells by enhancing a particular kinase activity in the cells. Of course, as is well known, enzyme variants exist or can be readily constructed, having conservative amino acid substitutions, cross-linking, cross-species domain substitutions, truncations, and the like, while preserving a physiologically-effective level of enzymatic activity (in this case, kinase activity for the PIM-1 target). The present discoveries are not focused only on a particular kinase, but include the discovery of an entirely new role for PIM kinase activity in vascular system cells and tissues. Thus, the results discussed herein flow from alteration of PIM kinase activity, regardless of the exact modality by which that is achieved.

The term "vascular system" is used herein to refer to the blood vessels and the heart, and all the tissues and cells of which they are comprised, including cardiac smooth muscle, cardiomyocytes, cardiomyoblasts, vascular wall, endothelium, vascular smooth muscle, vascular connective tissue, and other known cells and tissues of the vascular system.

The term "stem cell" is used broadly to include totipotent, pluripotent, and multipotent cells that can differentiate into vascular system cells, including cardiac cells. "Progenitor cells" overlaps somewhat with multipotent stem cells, and includes cells that are at least partially differentiated but that are multipotent or unipotent, in that they have the ability to differentiate into at least one type of vascular system cells.

The terms "treat" and "treatment" are used broadly, to include both prophylactic and therapeutic treatments. Similarly, when referring to disease or injury of circulatory system tissues, those terms are used broadly to include fully developed disease or injury, as well as incipient or threatened disease or injury. Thus, a patient at risk of or beginning to develop a particular condition, is considered to have that condition "treated" when methods as disclosed herein are used to reduce the risk of development or progression of that condition, as well as when an already-developed condition is reversed, inhibited, cured, or ameliorated, and when the rate of development of a condition is halted or slowed.

Those being treated are referred to variously as patients, individuals, subjects, humans, or animals. Treatments identified as useful for one category are also useful for other categories, and selection of a particular term (other than "human") is not intended to be limiting, but rather just a use of an alternative expression.

The disclosure includes compositions, such as pharmaceutical compositions, comprising nucleic acids encoding a PIM serine/threonine kinase, such as PIM-1, and methods for making and using them; including methods for inducing cardiac or vascular cellular proliferation, and protecting cardiac or vascular cells from hypoxia and cellular apoptosis. In one aspect, the compositions and methods of the invention are used to express PIM-1 to protect cardiomyocytes from hypertrophy and inhibit myocardial apoptosis induced by infarction, reducing infarct size. In another embodiment, the compositions and methods of the invention are used to express PIM-1 to induce cardiac or vascular cellular dedifferentiation and re-expression of stem cell markers; and in one aspect, to overexpress PIM-1 to enhance the regenerative potential of stem cells, including stem cell ability to engraft in the heart after a myocardial infarction (post-MI). In another embodiment, the compositions and methods of the invention are used to express PIM-1 to increase Bcl-XL expression to induce cardioprotective anti-apoptotic signaling, thus increasing myocardial survival signaling.

Also disclosed are compositions, such as pharmaceutical compositions, comprising nucleic acids encoding the serine/threonine kinase PIM-1 and methods for preventing or inhibiting cell or tissue damage, e.g., cardiomyocyte cell death or inhibiting an ischemic or reperfusion related injury; including preventing or inhibiting the irreversible cellular and tissue damage and cell death caused by ischemia, e.g., ischemia subsequent to reperfusion (which can exacerbates ischemic damage by activating inflammatory response and oxidative stress).

The disclosure further provides compositions, such as pharmaceutical compositions, comprising nucleic acids encoding a serine/threonine kinase PIM and methods for regulating cardiac or vascular cellular proliferation and survival.

Using human and murine myocardial samples, we have demonstrated that both human and murine myocardial cells show elevated PIM-1 expression in failing hearts; where the elevated PIM-1 has predominantly a nuclear localization. We have also shown that acute cardiomyopathic challenge also induces PIM-1 expression with nuclear and perinuclear distribution in mouse myocardium.

Expression of PIM-1 in postnatal mouse myocardium decreases with aging, and cardioprotective stimuli associated with AKT activation and nuclear-targeted AKT in particular increase PIM-1 expression. We disclose that cardiomyocyte apoptosis is inhibited by PIM-1 via increased expression of bcl-2, bcl-XL, and phosphorylation of Bad$^{S112}$. Ischemia reperfusion injury is enhanced in PIM-1 knockout mice. Since loss of PIM-1 expression or activity leads to increased AKT expression without associated cardioprotective effects, PIM-1 represents a critical and novel facet of survival signaling downstream of AKT in the myocardium.

Treatments and Medical Uses

Detailed strategies for enhancing PIM activity within circulatory tissues are provided below. Regardless of the method by which PIM activity is increased, we have discovered that enhancement of PIM activity has multiple beneficial effects in cardiac and other circulatory system tissues.

Initially, the care provider may wish to perform a patient selection step. This may include, for example, assessing whether a patient is in need of one or more of the various treatments, or identifying a patient in need of such treatment. Two significant categories of need warrant some discussion.

First, there are individuals with readily-diagnosable existing conditions, including known disease or injury to cardiac or other circulatory tissue that is treatable with the compositions, methods, or techniques contemplated herein. In those cases, diagnosis or identification of the disease or injury would constitute diagnosis, selection, or identification of an individual in need of the specified treatment.

Second, there are individuals in need of treatment that is more prophylactic, for example, treatment that takes advantage of the powerful cardioprotective properties exerted by PIM. In some cases, identification can take place by recognizing an inchoate disease or injury that would otherwise progress, for example, injury or other factors that have or will initiate apoptosis, or conditions or factors that enhance the risk of developing a particular condition. Identification and treatment of those individuals may be desirable to prevent development of a disease or injury or to slow its development.

In between these two alternatives are individuals with existing disease or injury, which disease or injury is likely to progress. Identification and treatment of those individuals is also contemplated.

One significant condition lending itself to treatment through enhancement of PIM activity in cardiac tissue is myocardial infarction or other ischemic injury. Prophylactic treatment is desirable, when high risk of ischemic injury can be identified. However, in many cases, the patient will be treated after the injury has occurred. Treatment should be commenced as soon as is practicable after the injury.

Similarly, PIM-activity enhancement can be used to treat a number of other conditions and to create desired physiological effects, by treating a subject to enhance PIM activity in vascular, cardiac, or other circulatory system cells or tissues. These include prevention, reduction, or reversal of cardiac hypertrophy, including but not limited to maladaptive hypertrophic remodeling; promoting cardiac cell survival and inhibiting apoptosis of those cells; enhancing cardiac contractility; improving cardiac ejection fraction; enhancing vascular growth and repair; and promoting differentiation of stem cells and progenitor cells toward cardiac or vascular tissue.

In another aspect, the methods contemplated herein include, but are not limited to, inhibition of cardiac apoptosis; inhibition of cardiac fibrosis; inhibition of cardiac remodeling; inhibition of cardiac hypertrophy; preservation or reduced loss of ejection fraction in damaged hearts; enhanced preservation of contractile function; decrease in cardiac necrosis; reduction in lesion size following ischemic injury; and increasing cardiac cellularity and decreasing myocyte volume. All of these methods can be practiced prophylactically (to prevent or reduce a particular condition that would otherwise be likely to occur) and therapeutically (to treat a condition that is already in existence, including treatment to slow progression of a condition).

From another perspective, conditions that may lead to treatment by enhancement of PIM activity include (but are not limited to) congenital heart conditions; ischemic injury of any kind to heart tissue; damage from infarction; cardiac reperfusion injury; traumatic cardiac injury; congestive heart failure injury; and injury relating to cardiac infection with a pathogen, including viral, bacterial, and parasitic pathogens. In addition to identifying an individual having a condition for which PIM treatment is desirable, methods of treating the individual can include a step of increasing the level of PIM activity in a target tissue, such as vascular tissue or cardiac tissue. This step can be practiced in the various ways disclosed herein. By way of example, and not limitation, those include administering factors or drugs to the patient, systemically or locally, that upregulate endogenous PIM expression; administering PIM protein, preferably in combination with a delivery modality, such as a linked transduction domain, a liposome, an antibody, or the like; administering PIM-encoding polynucleotide to the patient, including naked DNA administration, administration of the polynucleotide in a viral vector, liposome, or other delivery modality; electroporation of cells of a subject to deliver DNA; and administering an autologous cell to the subject (e.g., into the heart) that has been altered to enhance PIM expression, including cardiomyocytes, cardiac progenitor cells, cardiac stem cells, mesenchymal stem cells, hematopoietic stem cells, adipose-derived stem cells, and the like.

When administering cells to a human patient, for example, to treat a cardiac condition, the number of cells can be any amount effective to enhance cardiac function or structure or treat a target condition. Exemplary, non-limiting amounts include $10^5$ to $10^{10}$ cells, more typically $10^6$ to $10^9$ cells.

Exemplary, non-limiting amounts of PIM protein administered to an adult human heart can be, for example, from about $10^{-4}$ g to about $10^{-10}$ g, calculated as the pure PIM protein. Exemplary, non-limiting amounts of DNA include about 0.05 to 500 ug/kg, or 0.5 to 50 ug/kg body weight, and in the case of viral particles, formulated at a titer of about at least $10^{10}$, $10^{11}$, $10^{13}$, $10^{14}$, $10^{15}$, $10^{16}$, or $10^{17}$ physical particles per milliliter. In one aspect, the PIM-1 encoding nucleic acid is administered in about 10, 20, 30, 40, 50, 60, 70, 80, 90, 100, 110, 120, 130, 140 or 150 or more microliter (µl) injections. Doses and dosage regimens can be determined by conventional range-finding techniques known to those of ordinary skill in the art. For example, in alternative embodiments, about $10^6$, $10^7$, $10^8$, $10^9$, $10^{10}$, $10^{11}$, $10^{12}$, $10^{13}$, $10^{14}$, $10^{15}$, $10^{16}$ or $10^{17}$ viral (e.g., lentiviral) particles are delivered to the individual (e.g., a human patient) in one or multiple doses.

In other embodiments, an intracardiac single administration (e.g., a single dose) comprises from about 0.1 µl to 1.0 µl, 10 µl or to about 100 µl of a pharmaceutical composition of the invention. Alternatively, dosage ranges from about 0.5 ng or 1.0 ng to about 10 µg, 100 µg to 1000 µg of PIM-1 expressing nucleic acid is administered (either the amount in an expression construct, or as in one embodiment, naked DNA is injected).

PIM Sequences

Some embodiments include nucleic acid constructs comprising a PIM-encoding sequence, e.g., a PIM-1 expressing message or a PIM-1 gene. In one aspect, PIM-expressing nucleic acids used to practice this invention include PIM-1 genomic sequences, or fragments thereof, including coding or non-coding sequences, e.g., including introns, 5' or 3' non-coding sequences, and the like. Also encompassed are PIM-encoding mRNA sequences.

In one aspect, the PIM-1 expressing, or PIM-1 inducing or upregulating, composition is a nucleic acid, including a vector, recombinant virus, and the like; and a recombinant PIM-1 is expressed in a cell in vitro, ex vivo and/or in vivo.

In one aspect, a PIM-1 expressing nucleic acid encodes a human PIM-1, such as Genbank accession no. AAA36447 (see also, e.g., Domen (1987) Oncogene Res. 1 (1):103-112), SEQ ID NO:1.

In another aspect, a PIM-1 expressing nucleic acid encodes a human PIM-1 kinase 44 kDa isoform, see e.g., Genbank accession no. AAY87461 (see also, e.g., Xie (2006) Oncogene 25 (1), 70-78), SEQ ID NO:2.

In a further aspect, a PIM-1 expressing nucleic acid comprises a human PIM-1 kinase message (mRNA), see e.g., Genbank accession no. NM_002648 (see also, e.g., Zhang (2007) Mol. Cancer. Res. 5 (9), 909-922), SEQ ID NO:3.

Also disclosed are human DNA sequences of PIM-2 (SEQ ID NO:4) and PIM-3 (SEQ ID NO:5).

In alternative embodiments, nucleic acids of this invention are operatively linked to a transcriptional regulatory sequence, e.g., a promoter and/or an enhancer, e.g., cardiac-specific, promoters to drive (e.g., regulate) expression of Pim-1. Promoters and enhancers used to practice this invention can be of any type and/or origin, an in one embodiment promoters specific to the species receiving the Pim-1 construct are used; e.g., humans can receive human promoters, mice receive murine promoters, etc. In other embodiments, promoters from heterologous species can be used; e.g., mammals or vertebrates receiving promoters that originate from other mammals or vertebrates, or viral or synthetic promoters active in the appropriate specie and/or cell type also can be used. These promoters can comprise, for example, a α-myosin heavy chain promoter; a cardiac troponin-T promoter; a MLC-2v promoter; and any other promoter that drives expression in cardiac tissue but does not drive significant expression in other tissues. In one embodiment, promoters and enhancers active in primordial cells or stem cells, e.g., myocardial stem cells, can be operatively linked to drive expression of Pim-1.

Nucleic Acid Delivery—Gene Therapy Vehicles

In one aspect, this disclosure provides constructs or expression vehicles, e.g., expression cassettes, vectors, viruses (e.g., lentiviral expression vectors, e.g., see SEQ ID NO:4), and the like, comprising a PIM-encoding sequence, e.g., a PIM-1 encoding message or a PIM-1a gene, for use as ex vivo or in vitro gene therapy vehicles, or for expression of PIM-1 in heart tissue, a cardiac or vascular cell, tissue or organ to practice the methods of this invention, and for research, drug discovery or transplantation.

In one aspect, an expression vehicle used to practice the invention can comprise a promoter operably linked to a nucleic acid encoding a PIM protein (or functional subsequence thereof). For example, the invention provides expression cassettes comprising nucleic acid encoding a PIM-1 protein operably linked to a transcriptional regulatory element, e.g., a promoter.

In one aspect, an expression vehicle used to practice the invention is designed to deliver a PIM-1 encoding sequence, e.g., a PIM-1 gene or any functional portion thereof to a cardiac tissue or cell of an individual. Expression vehicles, e.g., vectors, used to practice the invention can be non-viral or viral vectors or combinations thereof. The invention can use any viral vector or viral delivery system known in the art, e.g., adenoviral vectors, adeno-associated viral (AAV) vectors, herpes viral vectors (e.g., herpes simplex virus (HSV)-based vectors), retroviral vectors, lentiviral vectors and baculoviral vectors.

In one aspect of the invention, an expression vehicle, e.g., a vector or a virus, is capable of accommodating a full-length PIM-1 gene or a message, e.g., a cDNA. In one aspect, the invention provides a retroviral, e.g., a lentiviral, vector capable of delivering the nucleotide sequence encoding full-length human PIM-1 in vitro, ex vivo and/or in vivo. An exemplary lentiviral expression vector backbone (no "payload" included, e.g., no PIM-1 sequence included) that can be used to practice this invention is set forth in SEQ ID NO:4.

In one embodiment, a lentiviral vector used to practice this invention is a "minimal" lentiviral production system lacking one or more viral accessory (or auxiliary) gene. Exemplary lentiviral vectors for use in the invention can have enhanced safety profiles in that they are replication defective and self-inactivating (SIN) lentiviral vectors. Lentiviral vectors and production systems that can be used to practice this invention include e.g., those described in U.S. Pat. Nos. 6,277,633; 6,312,682; 6,312,683; 6,521,457; 6,669,936; 6,924,123; 7,056,699; and 7,198,784; any combination of these are exemplary vectors that can be employed in the practice of the invention. In an alternative embodiment, non-integrating lentiviral vectors can be employed in the practice of the invention. For example, non-integrating lentiviral vectors and production systems that can be employed in the practice of the invention include those described in U.S. Pat. No. 6,808,923.

The expression vehicle can be designed from any vehicle known in the art, e.g., a recombinant adeno-associated viral vector as described, e.g., in U.S. Pat. App. Pub. No. 20020194630, Manning, et al.; or a lentiviral gene therapy vector, e.g., as described by e.g., Dull, et al. (1998) J. Virol. 72:8463-8471; or a viral vector particle, e.g., a modified retrovirus having a modified proviral RNA genome, as described, e.g., in U.S. Pat. App. Pub. No. 20030003582; or an adeno-associated viral vector as described e.g., in U.S. Pat. No. 6,943,153, describing recombinant adeno-associated viral vectors for use in the eye; or a retroviral or a lentiviral vector as described in U.S. Pat. Nos. 7,198,950; 7,160,727; 7,122,181 (describing using a retrovirus to inhibit intraocular neovascularization in an individual having an age-related macular degeneration); or U.S. Pat. No. 6,555,107.

Any viral vector can be used to practice this invention, and the concept of using viral vectors for gene therapy is well known; see e.g., Verma and Somia (1997) Nature 389:239-242; and Coffin et al ("Retroviruses" 1997 Cold Spring Harbour Laboratory Press Eds: J M Coffin, S M Hughes, H E Varmus pp 758-763) having a detailed list of retroviruses. Any lentiviruses belonging to the retrovirus family can be used for infecting both dividing and non-dividing cells with a PIM-1-encoding nucleic acid, see e.g., Lewis et al (1992) EMBO J. 3053-3058.

Viruses from lentivirus groups from "primate" and/or "non-primate" can be used; e.g., any primate lentivirus can be used, including the human immunodeficiency virus (HIV), the causative agent of human acquired immunodeficiency syndrome (AIDS), and the simian immunodeficiency virus (SIV); or a non-primate lentiviral group member, e.g., including "slow viruses" such as a visna/maedi virus (VMV), as well as the related caprine arthritis-encephalitis virus (CAEV), equine infectious anemia virus (EIAV) and/or a feline immunodeficiency virus (FIV) or a bovine immunodeficiency virus (BIV).

In alternative embodiments, lentiviral vectors used to practice this invention are pseudotyped lentiviral vectors. In one aspect, pseudotyping used to practice this invention incorporates in at least a part of, or substituting a part of, or replacing all of, an env gene of a viral genome with a heterologous env gene, for example an env gene from another virus. In alternative embodiments, the lentiviral vector of the invention is pseudotyped with VSV-G. In an alternative embodiment, the lentiviral vector of the invention is pseudotyped with Rabies-G.

Lentiviral vectors used to practice this invention may be codon optimized for enhanced safety purposes. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available. Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms. Codon optimization has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimization also overcomes the Rev/RRE requirement for export, rendering optimized sequences Rev independent. Codon optimization also reduces homologous recombination between different constructs within the vector system (for example between the regions of overlap in the gag-pol and env open reading frames). The overall effect of codon optimization is therefore a notable increase in viral titer and improved safety. The strategy for codon optimized gag-pol sequences can be used in relation to any retrovirus.

Vectors, recombinant viruses, and other expression systems used to practice this invention can comprise any nucleic acid which can infect, transfect, transiently or permanently transduce a cell. In one aspect, a vector used to practice this invention can be a naked nucleic acid, or a nucleic acid complexed with protein or lipid. In one aspect, a vector used to practice this invention comprises viral or bacterial nucleic acids and/or proteins, and/or membranes (e.g., a cell membrane, a viral lipid envelope, etc.). In one aspect, expression systems used to practice this invention comprise replicons (e.g., RNA replicons, bacteriophages) to which fragments of DNA may be attached and become replicated. In one aspect, expression systems used to practice this invention include, but are not limited to RNA, autonomous self-replicating circular or linear DNA or RNA (e.g., plasmids, viruses, and the like, see, e.g., U.S. Pat. No. 5,217,879), and include both the expression and non-expression plasmids.

In one aspect, a recombinant microorganism or cell culture used to practice this invention can comprise "expression vector" including both (or either) extra-chromosomal circular and/or linear nucleic acid (DNA or RNA) that has been incorporated into the host chromosome(s). In one aspect, where a vector is being maintained by a host cell, the vector may either be stably replicated by the cells during mitosis as an autonomous structure, or is incorporated within the host's genome.

In one aspect, an expression system used to practice this invention can comprise any plasmid, which are commercially available, publicly available on an unrestricted basis, or can be constructed from available plasmids in accord with published procedures. Plasmids that can be used to practice this invention are well known in the art.

In alternative aspects, a vector used to make or practice the invention can be chosen from any number of suitable vectors known to those skilled in the art, including cosmids, YACs (Yeast Artificial Chromosomes), megaYACS, BACs (Bacterial Artificial Chromosomes), PACs (P1 Artificial Chromosome), MACs (Mammalian Artificial Chromosomes), a whole chromosome, or a small whole genome. The vector also can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook. Bacterial vectors which can be used include commercially available plasmids comprising genetic elements of known cloning vectors.

Pharmaceutical Compositions

The invention provides compositions, including pharmaceutical compositions, and methods for expressing PIM; e.g., for expressing PIM-1 or another functionally-equivalent kinase to protect cardiomyocytes from hypertrophy and to inhibit myocardial apoptosis induced by infarction, and to reduce infarct size. (Functional equivalence is considered to exist based on ability to act on the same substrate and produce the same product, and does not require identical kinetics.) In another embodiment, the pharmaceutical compositions of the invention are used to express PIM-1 to induce cardiac or vascular cellular dedifferentiation and re-expression of stem cell markers; and in one aspect, to overexpress PIM-1 to enhance the regenerative potential of stem cells, including stem cell ability to engraft in the heart after a myocardial infarction (post-MI).

In one aspect, the PIM-1 expressing, or PIM-1 inducing or upregulating, composition is a nucleic acid, including a vector, recombinant virus, and the like; and a recombinant PIM-1 is expressed in a cell in vitro, ex vivo and/or in vivo.

In alternative embodiments, in practicing use of the pharmaceutical compositions and methods of this invention, compounds that induce or upregulate PIM nucleic acid or a PIM kinase activity in the heart or a cardiac or vascular cell, tissue or organ are administered. For example, compounds that can be administered in practicing use of the pharmaceutical compositions and methods of this invention can comprise: an interleukin, a cytokine and/or a paracrine factor involved in survival and/or proliferative signaling; an up-regulator of AKT serine/threonine kinase; insulin-like growth factor-1 (IGF-1); insulin; leukemia inhibitory factor (LIF); granulocyte-macrophage colony-stimulating factor (GM-CSF); or epidermal growth factor (EGF). Okadaic acid and SV40 small T antigen inhibit or block negative regulation of PIM-1 by protein phosphatase 2A, and can thus be used to increase PIM-1 levels. See Maj, et al., Oncogene 26(35):5145-53 (2007).

In alternative embodiments, the PIM-expressing, or PIM-inducing or upregulating, compositions of the invention are formulated with a pharmaceutically acceptable carrier. In alternative embodiments, the pharmaceutical compositions of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents of the invention can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the PIM-expressing, or inducing or upregulating, compositions of the invention include those suitable for systemic administration, direct local vascular or cardiac administration, or alternatively oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations of this invention may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a chimeric polypeptide or peptidomimetic of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals can be used to deliver PIM-1 expressing, or PIM-1 inducing or upregulating, compositions of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In practicing this invention, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols.

In practicing this invention, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing this invention, the pharmaceutical compounds can be parenterally administered, such as by intravenous (IV) administration or administration into a body cavity or lumen of the heart. Use of catheters that temporarily block flow of blood from the heart while incubating the stem cells or a viral construct in heart tissue can be used, as well as recirculation systems of well-known type that isolate the circulation in all or a part of the heart to increase the dwell time of an introduced agent (e.g., stem cell, construct, naked DNA, PIM protein, viral or other vector) in the heart. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations of the invention can be delivered by the use of liposomes (see also discussion, below). By using liposomes, particularly where the liposome surface carries ligands specific for target cells, or are otherwise preferentially directed to a specific organ, one can focus the delivery of the active agent into target cells of the heart or other part of the circulatory system in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations of the invention can be administered for prophylactic and/or therapeutic treatments. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). For example, in alternative embodiments, pharmaceutical compositions of the invention are administered in an amount sufficient to treat, prevent and/or ameliorate the deleterious effects on the heart of a myocardial infarction (post-MI); to protect cardiomyocytes from hypertrophy and to inhibit myocardial apoptosis induced by infarction, and to reduce infarct size. In another embodiment, the pharmaceutical compositions of the invention are used to express PIM-1 to induce cellular dedifferentiation and re-expression of stem cell markers; and in one aspect, to overexpress PIM-1 to enhance the regenerative potential of stem cells, including stem cell ability to engraft in the heart post-MI.

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. Methods for preparing parenterally or non-parenterally administrable formulations are known or apparent to those skilled in the art and are described in more detail in such publications as Remington's.

The methods of the invention can further comprise co-administration with other drugs or pharmaceuticals, e.g., compositions for treating heart attacks, congestive heart failure and related symptoms or conditions. For example, the methods and/or compositions and formulations of the invention can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Nanoparticles and Liposomes

The invention also provides nanoparticles and liposomal membranes comprising the PIM-1-expressing compounds of this invention which target specific molecules, including biologic molecules, such as polypeptide, including cardiac or vascular or stem cell surface polypeptides, including heart cell (e.g., myocyte) cell surface polypeptides. In alternative embodiments, the invention provides nanoparticles and liposomal membranes targeting diseased and/or injured heart cells, or stem cells, such as any pluripotent cell.

In alternative embodiments, the invention provides nanoparticles and liposomal membranes comprising (in addition to comprising compounds of this invention) molecules, e.g., peptides or antibodies, that selectively target diseased and/or injured heart cells, or stem cells. In alternative embodiments, the invention provides nanoparticles and liposomal membranes using interleukin receptors and/or other receptors to target receptors on cells, e.g., diseased and/or injured heart cells, or stem cells. See, e.g., U.S. patent application publication no. 20060239968.

Thus, in one aspect, the compositions of the invention are specifically targeted to stem cells or heart cells, such as myocytes.

The invention also provides nanocells to allow the sequential delivery of two different therapeutic agents with different modes of action or different pharmacokinetics, at least one of which comprises a composition of this invention. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients suffering from any disease or condition as described herein, e.g., such as congestive heart failure or heart attack (myocardial infarction). For example, in treating myocardial infarction, an antibody and/or angiogenic agent can be contained in the outer lipid vesicle of the nanocell, and a composition of this invention is loaded into the nanocore. This arrangement allows the antibody and/or angiogenic agent to be released first and delivered to the injured tissue.

The invention also provides multilayered liposomes comprising compounds of this invention, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome of the invention may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharide or an oligosaccharide, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

The invention also provides nanoparticles comprising compounds of this invention to deliver a composition of the invention as a drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

Gene Therapy Delivery Methods

The PIM-1 expressing nucleic acid compositions of the invention can be delivered for ex vivo or in vivo gene therapy to deliver a PIM-1 encoding nucleic acid. In one aspect, PIM-1 expressing nucleic acid compositions of the invention, including non-reproducing viral constructs expressing high levels of the human PIM-1 protein, are delivered ex vivo or for in vivo gene therapy.

The PIM-1 expressing nucleic acid compositions of the invention can be delivered to and expressed in a variety of cardiac or vascular cells to induce cellular proliferation, and/or to protect cardiac or vascular cells from hypoxia and cellular apoptosis. PIM-1 so expressed (by practicing the composition and methods of this invention) can protect cardiomyocytes from hypertrophy and inhibit cell death induced by myocardial infarction (e.g. heart attack), reducing the amount of muscle affected. In addition, PIM-1 overexpression (by practicing the composition and methods of this invention) in cardiac or vascular cells, e.g., in heart cells, results in cellular reversion; the cardiac or vascular cells become stem cell like; complete with re-expression of stem cell markers (such as cardiac stem cell markers).

In one aspect, overexpression of PIM-1 (by practicing the compositions and methods of this invention) enhances the regenerative potential of stem cells and their ability to repair a damaged or injured organ (e.g., an injured heart after a heart attack). In one aspect, the invention provides compositions and methods for overexpressing PIM-1 using a controlled system using cultured stem cells prior to reintroduction in the adult human to enhance their ability to repair the organ following injury.

The invention provides use of PIM-1 for a clinical therapy for repair of a number of tissues damaged by low oxygen or other means through use of a conditional control element that allows control of PIM-1 expression. For example, PIM-1 expressing nucleic acid delivery vehicles, e.g., expression constructs, such as vectors or recombinant viruses, can be injected directly into the organ (e.g., a heart) to protect it from immediate injury. Expression of the protein can be then activated through an oral prescription drug (formulations for which are discussed above).

In one embodiment vectors used to practice this invention, e.g., to generate a PIM-expressing cell, are bicistronic. In one embodiment, a MND (or, myeloproliferative sarcoma virus LTR-negative control region deleted) promoter is used to drive Pim-1 expression. In one embodiment, a reporter is also used, e.g., an enhanced green florescent protein (eGFP) reporter, which can be driven off a viral internal ribosomal entry site (vIRES). In alternative embodiments, all constructs are third generation self-inactivating (SIN) lentiviral vectors and incorporate several elements to ensure long-term expression of the transgene. For example, a MND promoter allows for high expression of the transgene, while the LTR allows for long-term expression after repeated passage. In alternative embodiments, the vectors also include (IFN)-β-scaffold attachment region (SAR) element; SAR elements have been shown to be important in keeping the vector transcriptionally active by inhibiting methylation and protecting the transgene from being silenced.

In alternative embodiments, as a secondary course of therapy, PIM-1 expressing nucleic acid delivery vehicles, e.g., expression constructs, such as vectors or recombinant viruses, can be used to enhance proliferation during culture of adult stem cells extracted from the patient's damaged heart or other organ. In alternative embodiments, blood, fat, or marrow-derived stem cells can also be used. PIM-1 expression can be activated through addition of the drug to culture media. After a number of days in culture, the expression of PIM-1 can be then turned off through removal of the drug; and, in one aspect, the increased number of cells produced in culture are reintroduced into the damaged area contributing to an enhanced repair process.

The invention can incorporate use of any non-viral delivery or non-viral vector systems are known in the art, e.g., including lipid mediated transfection, liposomes, immunoliposomes, lipofectin, cationic facial amphiphiles (CFAs) and combinations thereof.

In one aspect, expression vehicles, e.g., vectors or recombinant viruses, used to practice the invention are injected directly into the heart muscle. In one aspect, the PIM-1 encoding nucleic acid is administered to the individual by direct injection. Thus, in one embodiment, the invention provides sterile injectable formulations comprising expression vehicles, e.g., vectors or recombinant viruses, used to practice the invention.

In alternative embodiments, it may be appropriate to administer multiple applications and employ multiple routes, e.g., directly into the heart muscle and intravenously, to ensure sufficient exposure of target cells (e.g., myocytes or stem cells) to the expression construct. Multiple applications of the expression construct may also be required to achieve the desired effect.

One particular embodiment of the invention is the ex vivo modification of stem cells of any origin or any pluripotent cell to enhance PIM-1 expression, followed by administration of the stem cells to a human or other mammalian host, or to any vertebrate. The stem cells may be directly or locally administered, for example, into cardiac tissue in the same manner as in existing stem cell therapy for cardiac injury or insufficiency. Alternatively, systemic administration is also contemplated. The stem cells may be autologous stem cells or heterologous stem cells. They may be derived from embryonic sources or from infant or adult organisms. The enhancement of PIM-1 expression may for example be the result of upregulation of the expression of existing chromosomal PIM-1-encoding sequence in the stem cells, or may be the result of insertion of an exogenous polynucleotide operably encoding PIM-1. As discussed in other contexts herein, a PIM-1-encoding insert in such stem cells may advantageously be under inducible expression control. In addition, the use of a "suicide sequence" of known type In alternative embodiments, one or more "suicide sequences" are also administered, either separately or in conjunction with a nucleic acid construct of this invention, e.g., incorporated within the same nucleic acid construct (such as a vector, recombinant virus, and the like. See, e.g., Marktel S, et al., Immunologic potential of donor lymphocytes expressing a suicide gene for early immune reconstitution after hematopoietic T-cell-depleted stem cell transplantation. Blood 101:1290-1298 (2003). Suicide sequences used to practice this invention can be of known type, e.g., sequences to induce apoptosis or otherwise cause cell death, e.g., in one aspect, to induce apoptosis or otherwise cause cell death upon administration of an exogenous trigger compound or exposure to another type of trigger, including but not limited to light or other electromagnetic radiation exposure.

In one aspect, a PIM-1 encoding nucleic acid-comprising expression construct or vehicle of the invention is formulated at an effective amount of ranging from about 0.05 to 500 ug/kg, or 0.5 to 50 ug/kg body weight, and can be administered in a single dose or in divided doses. However, it should be understood that the amount of a PIM-1 encoding nucleic acid of the invention, or other the active ingredient (e.g., a PIM-1 inducing or upregulating agent) actually administered ought to be determined in light of various relevant factors including the condition to be treated, the age and weight of the individual patient, and the severity of the patient's symptom; and, therefore, the above dose should not be intended to limit the scope of the invention in any way.

In one aspect, a PIM-1 encoding nucleic acid-comprising expression construct or vehicle of the invention is formulated at a titer of about at least $10^{10}$, $10^{11}$, $10^{12}$, $10^{13}$, $10^{14}$, $10^{15}$, $10^{16}$, or $10^{17}$ physical particles per milliliter. In one aspect, the PIM-1 encoding nucleic acid is administered in about 10, 20, 30, 40, 50, 60, 70, 80, 90, 100, 110, 120, 130, 140 or 150 or more microliter (µl) injections. Doses and dosage regimens can be determined by conventional range-finding techniques known to those of ordinary skill in the art. For example, in alternative embodiments, about $10^6$, $10^7$, $10^8$, $10^9$, $10^{10}$, $10^{11}$, $10^{12}$, $10^{13}$, $10^{14}$, $10^{15}$, $10^{16}$ or $10^{17}$ viral (e.g., lentiviral) particles are delivered to the individual (e.g., a human patient) in one or multiple doses.

In other embodiments, an intracardiac single administration (e.g., a single dose) comprises from about 0.1 µl to 1.0 µl, 10 µl or to about 100 µl of a pharmaceutical composition of the invention. Alternatively, dosage ranges from about 0.5 ng or 1.0 ng to about 10 µg, 100 µg to 1000 µg of PIM-1 expressing nucleic acid is administered (either the amount in an expression construct, or as in one embodiment, naked DNA is injected). Any necessary variations in dosages and routes of administration can be determined by the ordinarily skilled artisan using routine techniques known in the art.

In one embodiment, a PIM-1 expressing nucleic acid is delivered in vivo directly to a heart using a viral stock in the form of an injectable preparation containing pharmaceutically acceptable carrier such as saline. The final titer of the vector in the injectable preparation can be in the range of between about $10^8$ to $10^{14}$, or between about $10^{10}$ to $10^{12}$, viral particles; these ranges can be effective for gene transfer.

In one aspect, PIM-1 expressing nucleic acids (e.g., vector, transgene) constructs are delivered to the myocardium by direct intracoronary injection, e.g., using a standard percutaneous catheter based methods under fluoroscopic guidance. Alternatively, PIM-1 expressing nucleic acids (e.g., vector, transgene) constructs are delivered to organs and tissues, e.g., the heart, directly into both coronary and/or peripheral arteries, e.g., using a lipid-mediated gene transfer.

In these aspects, including direct intracoronary injection, or directly into both coronary and/or peripheral arteries, can be at an amount sufficient for the PIM-1 expressing nucleic acids (e.g., vector, transgene) to be expressed to a degree which allows for sufficiently effective; e.g., the amount of the PIM-1 expressing nucleic acid (e.g., vector, transgene) injected can be in the range of between about $10^8$ to $10^{14}$, or between about $10^{10}$ to $10^{12}$, viral particles. The injection can be made deeply (such as 1 cm within the arterial lumen) into the lumen of the coronary arteries, and can be made in both coronary arteries, as the growth of collateral blood vessels is highly variable within individual patients. By injecting the material directly into the lumen of the coronary artery by coronary catheters, it is possible to target the PIM-1 expressing nucleic acid (e.g., vector, transgene) rather effectively, and to minimize loss of the recombinant vectors to the proximal aorta during injection. Any variety of coronary catheter, or Stack perfusion catheters, and the like can be used. See, e.g., U.S. Patent App. Pub. No. 20040132190.

In one aspect, the invention combines a therapeutic PIM-1 nucleic acid with a genetic "sensor" that recognizes and responds to the oxygen deprivation that follows the reduced blood flow, or ischemia, from coronary artery disease and heart attack. As soon as the oxygen declines, the sensor turns on the therapeutic gene, thereby protecting the heart. In addition to its potential for patients with heart disease, the aspect of this invention is useful for any condition in which circulatory system tissues are susceptible to loss of blood supply, including stroke, shock, trauma and sepsis.

Direct PIM Delivery

In addition to cellular and nucleic acid approaches, PIM proteins can also be delivered directly to the affected cardiac or other circulatory tissues. Because PIM acts intracellularly, it is preferred to utilize a delivery strategy to facilitate intracellular delivery of PIM.

One technique that can be used is to provide the PIM in a vehicle that in taken up by or that fuses with a target cell. Thus, for example, PIM can be encapsulated within a liposome or other vesicle, as described in more detail above in connection with polynucleotide delivery to cells.

Alternatively, the PIM may be linked to a transduction domain, such as TAT protein. In some embodiments, PIM enzyme can be operably linked to a transduction moiety, such as a synthetic or non-synthetic peptide transduction domain (PTD), Cell penetrating peptide (CPP), a cationic polymer, an antibody, a cholesterol or cholesterol derivative, a Vitamin E compound, a tocol, a tocotrienol, a tocopherol, glucose, receptor ligand or the like, to further facilitate the uptake of the PIM by cells.

A number of protein transduction domains/peptides are known in the art and facilitate uptake of heterologous molecules linked to the transduction domains (e.g., cargo molecules). Such peptide transduction domains (PTD's) facilitate uptake through a process referred to as macropinocytosis. Macropinocytosis is a nonselective form of endocytosis that all cells perform.

Exemplary peptide transduction domains (PTD's) are derived from the *Drosophila* homeoprotein antennapedia transcription protein (AntHD) (Joliot et al., New Biol. 3:1121-34, 1991; Joliot et al., Proc. Natl. Acad. Sci. USA, 88:1864-8, 1991; Le Roux et al., Proc. Natl. Acad. Sci. USA, 90:9120-4, 1993), the herpes simplex virus structural protein VP22 (Elliott and O'Hare, Cell 88:223-33, 1997), the HIV-1 transcriptional activator TAT protein (Green and Loewenstein, Cell 55:1179-1188, 1988; Frankel and Pabo, Cell 55:1189-1193, 1988), and more recently the cationic N-terminal domain of prion proteins. Preferably, the peptide transduction domain increases uptake of the biomolecule to which it is fused in a receptor independent fashion, is capable of transducing a wide range of cell types, and exhibits minimal or no toxicity (Nagahara et al., Nat. Med. 4:1449-52, 1998). Peptide transduction domains have been shown to facilitate uptake of DNA (Abu-Amer, supra), antisense oligonucleotides (Astriab-Fisher et al., Pharm. Res, 19:744-54, 2002), small molecules (Polyakov et al., Bioconjug. Chem. 11:762-71, 2000) and even inorganic 40 nanometer iron particles (Dodd et al., J. Immunol. Methods 256:89-105, 2001; Wunderbaldinger et al., Bioconjug. Chem. 13:264-8, 2002; Lewin et al., Nat. Biotechnol. 18:410-4, 2000; Josephson et al., Bioconjug., Chem. 10:186-91, 1999).

Fusion proteins with such trans-cellular delivery proteins can be readily constructed using known molecular biology techniques.

In addition, any of the polynucleotides encoding PIM molecules can be linked to the foregoing domains to facilitate transduction of those polynucleotides into target cells, in vivo or in vitro.

Kits and Libraries

The invention provides kits comprising compositions of this invention and methods of the invention, including PIM-expressing, or PIM-inducing or upregulating compositions and/or nucleic acids of the invention, including vectors, recombinant viruses and the like, transfecting agents, transducing agents, cardiac or vascular cells and/or cell lines, instructions (regarding the methods of the invention), or any combination thereof. As such, kits, cells, vectors and the like are provided herein.

The invention will be further described with reference to the following examples; however, it is to be understood that the invention is not limited to such examples.

EXAMPLE 1

Demonstrating the Therapeutic Efficacy of Upregulating PIM-1

This example demonstrates that the compositions of the invention comprising nucleic acids encoding the serine/threonine kinase PIM-1, and the methods of this invention, are effective for inducing cellular proliferation, and protecting cells from hypoxia and cellular apoptosis; and to express PIM-1 kinase to protect cardiomyocytes from hypertrophy and/or inhibit myocardial apoptosis induced by infarction, reducing infarct size; and to express PIM-1 to induce cellular dedifferentiation and re-expression of stem cell markers; and to overexpress PIM-1 to enhance the regenerative potential of stem cells, including stem cell ability to engraft in the heart after a myocardial infarction (post-MI). These data demonstrate that in using compositions and methods described herein, PIM-1 functions as a defense against apoptotic stimuli induced during ischemic/reperfusion injury resulting from myocardial infarction, pressure-overload induced hypertrophy, and heart failure.

Results

PIM-1 is Expressed in the Human Myocardium and Upregulated in Failure.

Immunohistochemistry of normal and failing human heart samples indicates that PIM-1 expression is distributed throughout the cytoplasm in normal adult human myocardium. In contrast, in failing human heart samples, PIM-1 becomes mostly nuclear. Immunoblotting of human heart lysates demonstrates that PIM-1 expression increases 2.65-fold in the failing human myocardium when compared to normal controls. A similar pattern is seen in tropomodulin overexpressing transgenic (TOT) mice, a DCM model. Though PIM-1 is expressed at low levels in the 6 month old wildtype (NTG) mouse, expression in the TOT mouse is increased 5.9-fold and was mostly nuclear.

PIM-1 Expressed in the Mouse Myocardium is Developmentally Regulated.

Immunoblot analysis of myocardial lysates from mice at various time points after birth demonstrates decreasing PIM-1 expression with age. Neonatal heart samples exhibit 6.3-fold more PIM-1 than 30 week old mice. Postnatal expression levels decline, but remain significantly elevated, until 8 weeks of age when they became comparable to 30 week old hearts. Confocal microscopy of mouse hearts at various developmental time points show PIM-1 expression is predominantly nuclear in neonates, becomes increasingly cytosolic in early adulthood, and is virtually absent in the 30 week old adult. This is corroborated by immunoblotting of subcellular fractionated myocardium for PIM-1. PIM-1 expression is 10.5-fold and 5.2-fold more nuclear and 5.0 and 4.6-fold less cytosolic in neonatal hearts and 8 week old hearts respectively when compared to 30 week old mouse myocardium.

PIM-1 Exhibits Cardioprotective Effects In Vivo.

Using an art-accepted animal model, these data demonstrate that expression of PIM-1 in vivo has a cardioprotective effect. PIM-1 localization and expression were examined in hearts from 3-month old normal mice processed four days after sham or cardio-myopathic injury resulting from infarction (MI) or pressure overload (TAC). Four days following TAC banding to induce pressure-overload hypertrophy, a marked peri-nuclear increase in PIM-1 immunoreactivity is observed in cardiomyocytes surrounding major vessels. Similarly, peri-nuclear PIM-1 immunoreactivity is increased in border zone cardiomyocytes, but is unaffected in healthy regions of remote myocardium. PIM-1 positive border zone cardiomyocytes are negative for "terminal deoxynucleotidyl transferase-mediated dUTP-biotin nick end labeling" (TUNEL) labeling and exhibit increased Bcl-XL expression indicative of cardioprotective anti-apoptotic signaling, demonstrating a role for PIM-1 in myocardial survival signaling, also demonstrating the compositions and methods of the invention can be effective in myocardial survival signaling by expressing and/or upregulating PIM-1 kinase expression and/or activity.

A protective role for PIM-1 was confirmed using hearts of mice deficient for PIM-1 by genetic deletion subjected to ex vivo ischemia/reperfusion injury together with age and sex matched controls. Hearts of PIM-1 knockout mice exhibited statistically significant decreases in functional recovery following 45 minutes of reperfusion, as measured by left-ventricular developed pressure. TUNEL staining of paraffin embedded sections from hearts subjected to ex vivo ischemia reveals a 2.4-fold increase in the number of TUNEL positive cardiomyocytes in the PIM-1 knockout mice versus wildtype controls.

PIM-1 induces anti-apoptotic protein expression and protects cardiomyocytes in vitro. GFP-tagged cDNAs for wildtype 34 kDa PIM-1 (PIM-wt) or a kinase dead (K67M) mutant (PIM-DN) as previously described[10] were used to generate recombinant adenoviruses used for infection of neonatal rat cardiomyocyte cultures. Immunoblotting of lysates from cultures expressing GFP-PIM-wt or GFP-PIM-DN accumulate 64 kDa GFP-PIM-1 fusion proteins recognized by either GFP or PIM-1 antibodies. Cardiomyocytes overexpressing GFP-PIM-wt exhibit a statistically significant decrease in TUNEL labeling compared to EGFP infected controls. In comparison, GFP-PIM-DN overexpression induced a 30.8% increase in apoptotic cardiomyocytes (*p<0.05). Cultured cardiomyocytes were protected from apoptotic challenge with doxorubicin or deoxyglucose by GFP-PIM-wt overexpression (p<0.01 for both groups), whereas GFP-PIM-DN overexpression exacerbated apoptotic effects (p<0.01, and *p<0.05 respectively). Consistent with these results, GFP-PIM-DN induced a 3.6-fold increase in caspase3 cleavage and an 80% increase in cleaved poly (ADP-ribose) polymerase (PARP). In comparison, GFP-PIM-wt produced significant increases in bcl-XL and bcl-2 expression (2.2-fold and 25.4-fold, respectively) when compared to control (*p<0.01). GFP-PIM-wt also increased phosphorylation of Bad at the serine 112 residue (S112) by 16.7-fold versus uninfected control while levels of total Bad remained unchanged (*p<0.01).

PIM-1 is Induced by Cardioprotective Stimuli.

These data demonstrate that the compositions and methods of the invention can be used to increase the expression of PIM-1 to provide a cardioprotective effect, e.g., after a myocardial infarction. Treatment of neonatal rat cardiomyocyte cultures with cardioprotective agents including Leukemia Inhibitory Factor (LIF), Insulin-like Growth Factor (IGF-1), dexamethasone, and PMA, for 2 hours prior to assay induced PIM-1 immunoreactivity compared to control cells as visualized by confocal microscopy. PIM-1 immunoreactivity was not induced by phenylephrine, endothelin-1, forskolin, or estradiol (FIG. 4A). LIF, IGF, PMA, and dexamethasone induced PIM-1 expression by 2.8, 2.7, 2.3, and 2.0-fold respectively (*p<0.05, p<0.01). The adenylate cyclase activator, forskolin, reduced PIM-1 expression by 45% versus control cultures (p<0.01).

IGF-1 Induction of Pim-1 Expression is Akt-Dependent.

PIM-1 expression in response to IGF-1 treatment is significantly reduced in the presence of the PI3 kinase inhibitor wortmannin or inactivated AKT (AKT-DN) by 4.0-fold and 9.1-fold respectively (**p<0.001). A role for nuclear accumulation of AKT resulting following IGF stimulation[11] was confirmed, as overexpression of nuclear-targeted AKT[12] increased PIM-1 expression in cultured cardiomyocytes by 2.1-fold compared to uninfected controls (*p<0.05). In contrast, overexpression of wildtype AKT (AKT-wt) decreased expression of PIM-1 1.4-fold versus uninfected control (*p<0.05). Confocal micrographs of cultured cardiomyocytes demonstrate that expression of nuclear-targeted AKT induces increased nuclear localization of PIM-1 (FIG. 5C). Consistent with in vitro results, immunohistochemistry of hearts from six-month-old cardiac-specific nuclear-targeted AKT transgenics exhibit increased PIM-1 immunoreactivity and nuclear localization compared to controls and a representative immunoblot corroborates increased PIM-1 expression.

PIM-1 and AKT Exhibit Feedback Relationships.

AKT expression and phosphorylation ($S^{473}$) increase in response to overexpression of GFP-PIM-DN in cultured cardiomyocytes (FIG. 6A). Comparable findings of increased phospho-AKT$^{473}$ were observed with confocal microscopy of immunolabeled myocardial sections from 2-month old PIM-KO mice. Increased phospho-AKT$^{473}$ and total AKT in immunoblots of whole heart lysates from PIM-KO mice correlated with the immunostaining, demonstrating that regulation of Akt expression and activity depends, in part, upon PIM-1 levels.

Discussion

Using an art-accepted animal model, these data demonstrate that the compositions and methods of the invention can be used to increase the expression of PIM-1 to provide a cardioprotective effect (a myocardium protective effect), e.g., after a myocardial infarction. Molecular regulation of cardioprotection endures as a highly significant research avenue for therapeutic interventional strategies in the treatment of myocardial injury and heart failure. With this invention's discovery of a central role for PIM-1 in cardioprotection, as demonstrated by the data presented herein, a new facet of signaling has been uncovered with profound implications for regulation of cardiomyocyte survival and AKT-mediated effects. Taken together, data presented here provide the first evidence of PIM-1 expression and protective effects in the myocardium and demonstrate a reciprocal feedback mechanism between PIM-1 and AKT. The codependent interrelationship between AKT and PIM-1 previously documented in the hematopoeitic system[7] indicates both molecules work in concert.

PIM-1 Functions as a Defense Against Apoptotic Stimuli Induced During Ischemia/Reperfusion Injury PIM-1 has not previously been studied in the myocardial context studies. In non-cardiac cells is has been demonstrated that PIM-1 as a critical regulator of proliferation and cell survival signaling, e.g., as reviewed in ref[1] (see below). Using the compositions and methods of this invention, PIM-1 functions as a defense against apoptotic stimuli induced during ischemia/reperfusion injury resulting from myocardial infarction, pressure-overload induced hypertrophy, and heart failure. Although PIM-1 level is developmentally down-regulated, expression reappears in cardiomyocytes following cardiac injury by pressure-overload induced by TAC banding and myocardial infarction. PIM-1 is one of several protooncogenes participating in the "immediate early response" gene profile expressed following cardiac injury[13] including c-fos, c-myc[14], Raf and Ras. PIM-1 has been shown to cooperate with c-myc in activation of c-Myb dependent cellular proliferation in other tissues[15-17] suggesting synergistic effects between oncogenes may help preserve the myocardium in reaction to injury.

PIM-1 Potentiates Intracellular Anti-Apoptotic Signaling

Figure 3:
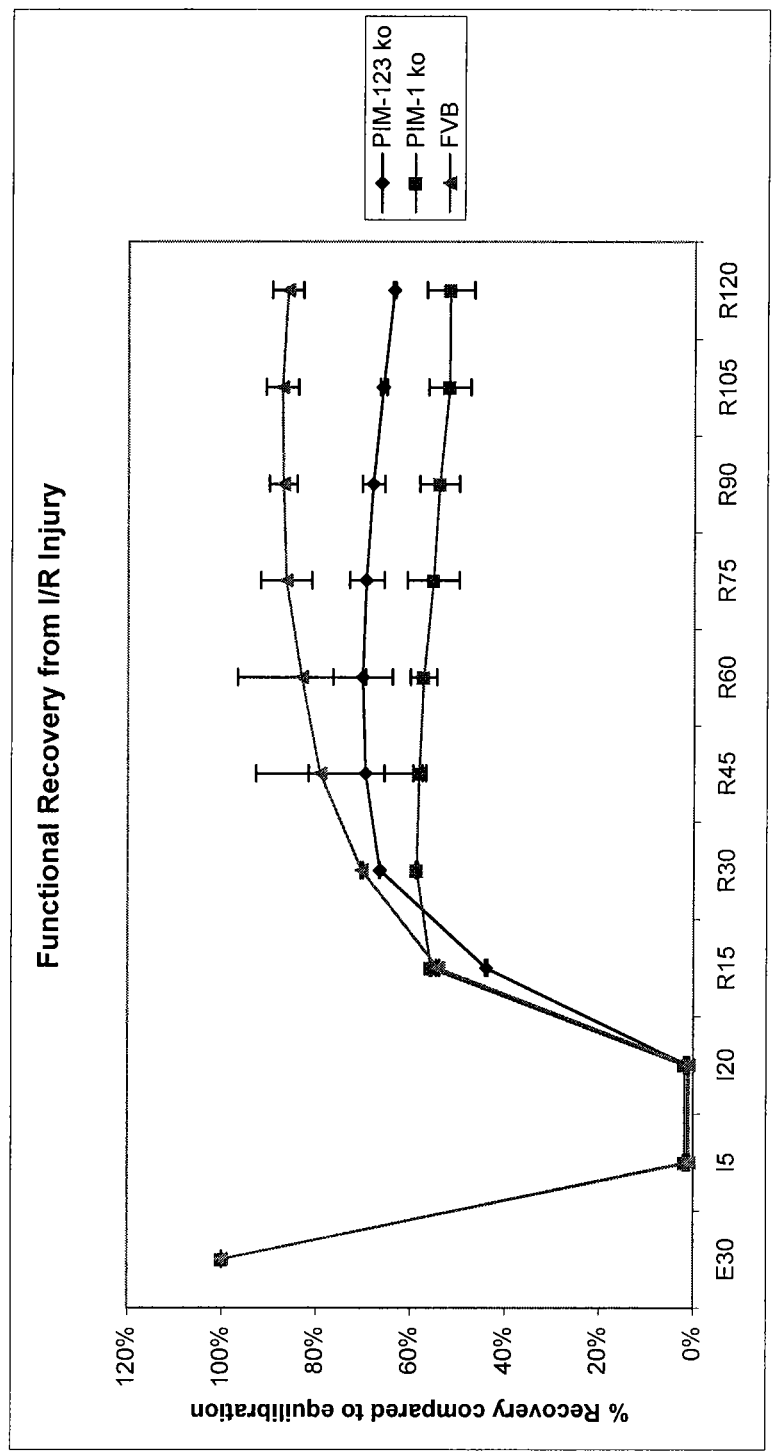
FIG. 3 graphically illustrates data showing that Pim-1 preserves hemodynamic function in ischemia-reperfusion injury, as described in detail in Example 2, below.

In addition to its proliferative effects, these data also demonstrate that PIM-1 potentiates intracellular anti-apoptotic signaling. Consistent with findings in non-cardiac cells,[17,18,19] adenoviral overexpression of PIM-1 protects neonatal rat cardiomyocytes from doxorubicin and deoxyglucose induced apoptosis through induction of bcl-2 and Bcl-XL expression as well as phosphorylation of Bad (FIG. 3). It is also possible that PIM-1 serves as the downstream effector of AKT induced p53 inhibition, since induction of mdm2 expression, phosphorylation, and p53 degradation is mediated by PIM-1[17] and AKT protects against doxorubicin induced apoptosis through a p53-dependent mechanism[20]. Furthermore, inactivation of PIM-1 induced apoptotic signaling in the cardiomyocyte context, exacerbating doxorubicin induced apoptosis. PIM-1 inactivation may also increase apoptotic activity through increasing generation of reactive-oxygen species and mitochondrial pore permeability, as has been found in other cellular contexts[18].

Several well known cardioprotective factors including LIF, the PKC activator PMA, the glucocorticoid dexamethasone, and IGF-1 significantly increased PIM-1 expression (FIG. 4), consistent with published reports showing induction of PIM-1 by PMA treatment of T cells[21] as well as gp130 receptor ligands including IL-6 and LIF[22, reviewed in 1]. These ligands and their cognate receptor are increased in the failing heart[23 24 25 26] as well as during development and hypertrophy of the myocardium.[27] With regard to other inductive stimuli, PMA-mediated PKC activation is cardioprotective,[28-30] correlative findings show PIM-1 is rapidly induced by PMA treatment in T cells.[21] IGF-1 mediates myocardial survival signaling[40-42] and stem cell proliferation[43] although we were unable to find prior published demonstration of PIM-1 induction by IGF. Results indicate that IGF-1 induced PIM-1 expression is AKT dependent and that nuclear-targeted AKT expression induces significant increases in PIM-1 expression in vitro and in vivo. Conversely, inactivation or ablation of PIM-1 expression induced AKT expression and activation, but increased AKT activation is unable to enhance recovery or reduce apoptosis following ischemia/reperfusion injury in PIM-1 null animals.

These results indicate that PIM-1 is an important mediator of cardioprotection downstream from comparatively well documented AKT signaling in the myocardium responsible for cardioprotection. Following growth factor or cytokine receptor activation, AKT is phosphorylated resulting in a conformational change which releases AKT from the membrane allowing it to transit through the cytosol and eventually to the nucleus where it affects transcription of target genes[31] and exerts cardioprotective activity.[12] Recent research demonstrates similar substrate specificity shared by PIM-1 and AKT[3], and that the widely employed PI3K inhibitor LY294002™ binds to and inhibits PIM-1 activity[32]. Therefore, previous studies involving the use of LY294002™ require reinterpretation in the context of AKT-dependent PIM-1 signaling in the myocardium.

Cardioprotective effects together with heightened expression in both postnatal/juvenile myocardium and pathologically challenged hearts implicate PIM-1 in promotion of phenotypic characteristics typically associated with a youthful myocardium. Indeed, the cytokine expression profile of neonatal myocardium share marked similarities with that exhibited by AKT-nuc transgenic hearts. It appears that many of the beneficial effects previously ascribed to Akt-nuc[11,12,33] (see references below) may depend, at least in part, upon induction of PIM-1 expression.

Methods

Neonatal Rat Cardiomyocyte Cultures infections and treatments. Neonatal rat cardiomyocyte cultures were prepared as described previously[12]. Cells to be subjected to treatments were placed in media with 2% serum overnight and then treated with the appropriate agent and harvested or fixed after the pre-described timepoint. Cardiomyocytes were infected with adenovirus for two hours, washed in PBS and then re-fed M199 with 2% FBS and 50 µg/ml pen/strep, and 100 µM glutamine.

Nuclear and cytosolic extraction. Hearts were washed in PBS, transferred to 2 ml of 0.57M STEAKM (0.57 M sucrose, 25 mM KCL, 5% $MgCl_2$, 1 mM DTT, 0.5 mM PMSF, 500 µl protease inhibitor and 50 µl phosphatase inhibitor), homogenized in ice using polytron and centrifuged for 10 minutes at 1000×g.

Pellets were resuspended in 1.5 mL of 0.57M STEAKM™, homogenized in tight fitting pestle and centrifuged at 1000×g for 10 minutes at 4° C. Supernatant was collected for cytosolic fraction.

Pellets were re-suspended in 750 µl of 0.57M STEAKM™ with 0.5% TRITON-X™ and centrifuged at 1000×g for 10 minutes at 4° C. Supernatant was collected for membrane fraction.

Pellets were re-suspended in 300 µl of 2.3M STEAKM™ (2.3M sucrose, 25 mM KCL, 5% $MgCl_2$, 1 mM DTT, 0.5 mM PMSF, 500 µl of protease inhibitor and 50 µl of phosphatase inhibitor). 2 volumes of 0.57M STEAKM™ was added and the pellets were gently mixed.

A layer of 2.7M STEAKM™ (2.7M sucrose, 25 mM KCL, 5% $MgCl_2$, 1 mM DTT, 0.5 mM PMSF, 500 µl of protease inhibitor and 50 µl of phosphatase inhibitor) was made at the bottom of an ultracentrifuge tube followed by a 2.4M STEAKM™ (2.4M sucrose, 25 mM KCL, 5% $MgCl_2$, 1 mM DTT, 0.5 mM PMSF, 500 µl of protease inhibitor and 50 µl of phosphatase inhibitor). The homogenate layer was added. The 3 layers were centrifuged at 112,000×g for 1 hour at 4° C. White interface between 2.7 and 2.4M STEAKM™ was collected for nuclear fraction. 5 volumes of 0.57 STEAKM™ was added and the pellets were centrifuged at 2000×g for 20 minutes at 4° C. The pellet was re-suspended in sample buffer containing phosphatase inhibitors and protease inhibitors.

Immunoblotting. Infected cardiomyocytes were harvested 24 hours after infection in SDS denaturing sample buffer, sonicated and boiled for 10 minutes, and quantitated using the Bradford assay. Mouse whole heart lysates were generated from flash frozen hearts pulverized in a mortar and pestle then resuspended in SDS denaturing sample buffer, sonicated, boiled for 10 minutes and quantitated using Bradford assay. Approximately 50 µg of each sample was loaded on a 4-15% gradient Bis-Acrylamide Tris Glycine gel and transferred to PVDF. Blots were blocked in 3% BSA for 1 hour, and probed with primary antibodies (PIM-1 (Cell Signaling Technology), c-jun (Cell Signaling Technology), HISTONE3™ (Cell Signaling Technology), GFP (Molecular Probes), bcl-2 (Santa Cruz), bcl-XL (Cell Signaling Technology), PHOSPHO-BADS112™ (Biosource) AKT (Cell Signaling Technology), GAPDH (Research Diagnostics Inc.), PHOSPHO-AKTS473™ (Cell Signaling Technology), total PARP (Biosource), cleaved PARP (Biosource), and cleaved caspase3 (Cell Signaling Technologies)) diluted in blocking solution overnight at 4° C. Blots were washed in TBS-0.5% Tween three times and probed with fluorescent or alkaline phosphatase conjugated secondary antibodies diluted 1:5000 in blocking solution for 1 hour at room temperature followed by three washes in TBS-0.5% Tween. Blots were scanned using a TYPHOON 9410 IMAGER™ (GE Healthcare) and quantitated using IMAGEQUANT 5.2™ software (GE Healthcare). All quantitation is based on standardization to loading controls.

Adenoviral constructs. AKT-nuc and AKT wildtype adenoviruses were prepared as described previously, see reference[12]. PIM-wt and PIM-DN adenoviruses were prepared by subcloning of the NheI/SmaI fragments from pEGFP-N1 PIM-1 and pEGFP-N1PIM-DN™ plasmids described previouslyl[10], into the pDC315io™ (Microbix) adenoviral shuttle vector. [32]Sequence verified shuttle vectors were cotransfected with the genomic pBHGloxΔE1,3Cre into 293iq™ cells (Microbix) to generate the adenovirus. Purified plaques were isolated and expanded for use in experiments.

Immunohistochemistry. Hearts were fixed and embedded and cardiomyocytes fixed and permeabilized as described previously[12]. Staining of cultured neonatal rat cardiomyocytes was performed with antibodies described above diluted 1:25 in PBS containing 10% horse serum overnight at 4° C. Slides were washed in PBS and probed with fluorescent conjugated secondary antibodies (1:100) for one hour at room temperature, and Texas Red phalloidin (1:50 Molecular Probes) to identify actin filaments. Slides were washed three times in PBS, and stained for 30 minutes with TOPRO-3™ (1:5000 Molecular Probes) to identify nuclei, washed once and cover-slipped using VECTRASHIELD™ (Vectra Labs). Paraffin embedded samples were cut at 4 µm and deparaffinized through a standard series of Xylene and graded Ethanol steps to water. Antigen retrieval was performed in 10 mM Citrate pH6.0. PIM-1 and phospho-AKT signals were amplified using the TYRAMIDE AMPLIFICATION KIT™ (Perkin Elmer) with primary concentrations of 1:500 for both antibodies, and secondaries 1:3000. Slides were washed following the amplification process, and stained with TOPRO-3 (Molecular Probes) to identify nuclei, washed and coverslipped with VECTRASHIELD™ (Vectra Labs). Confocal imaging of stained slides was performed on a Leica LCS confocal microscope. For comparison purposes, all slides were treated identically and scanned using the same settings in each experiment.

Doxorubicin and deoxyglucose induction of apoptosis. Cardiomyocytes were infected with GFP, PIM-wt, and PIM-DN viruses as described earlier. Twenty-four hours after infection, cells were treated with 1 μM Doxorubicin or 1 mM deoxyglucose for 16 hours then labeled for TUNEL using the 1N SITU CELL DEATH DETECTION KIT™, TMR red (Roche Applied Science) per manufacturer instructions. Number of infected TUNEL positive cells was counted for each treatment on a Nikon DIAPHOT 420™ fluorescent scope.

Myocardial infarction and trans-aortic constriction. Mice were placed under anesthesia, and the chest wall surgically opened. To induce an acute ischemic event, the left anterior descending artery (LAD) was located and ligated using 8-0 nylon suture. To induce pressure overload, the aorta was banded with 8-0 prolene using a 27 gauge needle as a guide. Sham animals were treated identically except the LAD or aorta were not ligated. Animal hearts were harvested as described above and embedded into paraffin.

Ex Vivo Ischemia/Reperfusion. Ex vivo ischemia/reperfusion was performed as described previously[34]. Sections from four hearts from each experimental group were cut and analyzed for cell death using TUNEL labeling (1N SITU CELL DEATH DETECTION KIT™, TMR red (Roche Applied Science)) according to the kit directions.

Statistical Analysis. Statistical analysis was performed using student T test, and analysis of variance (ANOVA) as appropriate. P values less than 0.05 were considered significant.

REFERENCES FOR EXAMPLE 1

1. Wang, Z. et al. PIM-1: a serine/threonine kinase with a role in cell survival, proliferation, differentiation and tumorigenesis. J Vet Sci 2, 167-79 (2001).
2. Xie, Y. et al. The 44 kDa PIM-1 kinase directly interacts with tyrosine kinase Etk/BMX and protects human prostate cancer cells from apoptosis induced by chemotherapeutic drugs. Oncogene (2005).
3. Bullock, A. N., Debreczeni, J., Amos, A., Knapp, S. & Turk, B. E. Structure and substrate specificity of the PIM-1 kinase. J. Biol. Chem., M510711200 (2005).
4. Palaty, C. K. et al. Identification of the autophosphorylation sites of the *Xenopus laevis* PIM-1 proto-oncogene-encoded protein kinase. J Biol Chem 272, 10514-21 (1997).
5. Bachmann, M. & Moroy, T. The serine/threonine kinase PIM-1. Int J Biochem Cell Biol 37, 726-30 (2005).
6. Aho, T. L. et al. PIM-1 kinase promotes inactivation of the pro-apoptotic Bad protein by phosphorylating it on the Ser112 gatekeeper site. FEBS Lett 571, 43-9 (2004).
7. Hammerman, P. S., Fox, C. J., Birnbaum, M. J. & Thompson, C. B. PIM and Akt oncogenes are independent regulators of hematopoietic cell growth and survival. Blood 105, 4477-83 (2005).
8. Krumenacker, J. S., Narang, V. S., Buckley, D. J. & Buckley, A. R. Prolactin signaling to PIM-1 expression: a role for phosphatidylinositol 3-kinase. J Neuroimmunol 113, 249-59 (2001).
9. Krishnan, N., Pan, H., Buckley, D. J. & Buckley, A. Prolactin-regulated PIM-1 transcription: identification of critical promoter elements and Akt signaling. Endocrine 20, 123-30 (2003).
10. Bhattacharya, N. et al. PIM-1 associates with protein complexes necessary for mitosis. Chromosoma 111, 80-95 (2002).
11. Camper-Kirby, D. et al. Myocardial Akt activation and gender: increased nuclear activity in females versus males. Circ Res 88, 1020-7 (2001).
12. Shiraishi, I. et al. Nuclear targeting of Akt enhances kinase activity and survival of cardiomyocytes. Circ Res 94, 884-91 (2004).
13. Sugden, P. H. & Clerk, A. Cellular mechanisms of cardiac hypertrophy. J Mol Med 76, 725-46 (1998).
14. Izumo, S., Nadal-Ginard, B. & Mandavi, V. Protooncogene Induction and Reprogramming of Cardiac Gene Expression Produced by Pressure Overload. PNAS 85, 339-343 (1988).
15. Katakami, N. et al. Role of PIM-1 in smooth muscle cell proliferation. J Biol Chem 279, 54742-9 (2004).
16. Hoefnagel, J. J. et al. Distinct types of primary cutaneous large B-cell lymphoma identified by gene expression profiling. Blood (2004).
17. Ionov, Y. et al. PIM-1 protein kinase is nuclear in Burkitt's lymphoma: nuclear localization is necessary for its biologic effects. Anticancer Res 23, 167-78 (2003).
18. Lilly, M., Sandholm, J., Cooper, J. J., Koskinen, P. J. & Kraft, A. The PIM-1 serine kinase prolongs survival and inhibits apoptosis-related mitochondrial dysfunction in part through a bcl-2-dependent pathway. Oncogene 18, 4022-31 (1999).
19. Macdonald, A. et al. PIM kinases phosphorylate multiple sites on Bad and promote 14-3-3 binding and dissociation from Bcl-XL. BMC Cell Biol 7, 1 (2006).
20. Fujiwara, Y. et al. Inhibition of the PI3 kinase/Akt pathway enhances doxorubicin-induced apoptotic cell death in tumor cells in a p53-dependent manner. Biochem Biophys Res Commun 340, 560-6 (2006).
21. Wingett, D., Long, A., Kelleher, D. & Magnuson, N. S. PIM-1 proto-oncogene expression in anti-CD3-mediated T cell activation is associated with protein kinase C activation and is independent of Raf-1. J Immunol 156, 549-57 (1996).
22. Rahman, Z., Yoshikawa, H., Nakajima, Y. & Tasaka, K. Down-regulation of PIM-1 and Bcl-2 is accompanied with apoptosis of interleukin-6-depleted mouse B-cell hybridoma 7TD1 cells. Immunol Lett 75, 199-208 (2001).
23. Eiken, H. G. et al. Myocardial gene expression of leukaemia inhibitory factor, interleukin-6 and glycoprotein 130 in end-stage human heart failure. Eur J Clin Invest 31, 389-97 (2001).
24. Hirota, H. et al. Circulating interleukin-6 family cytokines and their receptors in patients with congestive heart failure. Heart Vessels 19, 237-41 (2004).
25. Jougasaki, M. et al. Leukemia inhibitory factor is augmented in the heart in experimental heart failure. Eur J Heart Fail 5, 137-45 (2003).
26. Sheng, Z. et al. Cardiotrophin 1 (CT-1) inhibition of cardiac myocyte apoptosis via a mitogen-activated protein kinase-dependent pathway. Divergence from downstream CT-1 signals for myocardial cell hypertrophy. J Biol Chem 272, 5783-91 (1997).
27. Wollert, K. C. & Chien, K. R. Cardiotrophin-1 and the role of gp130-dependent signaling pathways in cardiac growth and development. J Mol Med 75, 492-501 (1997).

28. Sato, T., O'Rourke, B. & Marban, E. Modulation of mitochondrial ATP-dependent K+ channels by protein kinase C. Circ Res 83, 110-4 (1998).
29. Sato, T., Saito, T., Saegusa, N. & Nakaya, H. Mitochondrial Ca2+-activated K+ channels in cardiac myocytes: a mechanism of the cardioprotective effect and modulation by protein kinase A. Circulation 111, 198-203 (2005).
30. Philipp, S. et al. Postconditioning protects rabbit hearts through a protein kinase C-adenosine A2b receptor cascade. Cardiovasc Res 70, 308-14 (2006).
31. Pekarsky, Y. et al. Tcl1 enhances Akt kinase activity and mediates its nuclear translocation. Proc Natl Acad Sci USA 97, 3028-33 (2000).
32. Jacobs, M. D. et al. PIM-1 Ligand-bound Structures Reveal the Mechanism of Serine/Threonine Kinase Inhibition by LY294002. J. Biol. Chem. 280, 13728-13734 (2005).
33. Rota, M. et al. Nuclear targeting of Akt enhances ventricular function and myocyte contractility. Circ Res 97, 1332-41 (2005).
34. Kato, T. et al. Atrial natriuretic peptide promotes cardiomyocyte survival by cGMP-dependent nuclear accumulation of zyxin and Akt. J Clin Invest 115, 2716-2730 (2005).

EXAMPLE 2

Demonstrating the Therapeutic Efficacy of Upregulating PIM-1

This example also demonstrates that the compositions of the invention comprising nucleic acids encoding the serine/threonine kinase PIM-1, and the methods of this invention, are effective for inducing cellular proliferation, and protecting cells from hypoxia and cellular apoptosis; and to express PIM-1 kinase to protect cardiomyocytes from hypertrophy and/or inhibit myocardial apoptosis induced by infarction, reducing infarct size.

Until relatively recently, dogma held that cardiomyocytes rarely underwent programmed cell death, were impervious to the effects of aging, and incapable of regeneration. The last decade of cardiovascular research has produced major paradigm shifts in the perceptions of cardiomyocyte biology. The emerging picture of the myocardium is quite unlike previous notions of a tenaciously steadfast contracting cell that persists throughout the lifespan of the organism. Instead, cardiomyocytes like many other cell types in the body possess a finite lifespan characterized by ongoing processes of birth, survival, death, and (more controversially) regeneration. Consequently, this new perspective has reinvigorated research into the molecular mechanisms that regulate survival and the cardiomyocyte life cycle.[1]

Cellular proliferation and survival are regulated, in part, by the action of signaling cascades that lead to activation of kinases such as protein kinase C (PKC), Akt/PKB, and PIM-1. Voluminous research in the context of the cardiovascular system has established both PKC and Akt/PKB as fundamental pillars upon which cardiomyocyte function is maintained. In contrast, the cardiovascular role of PIM-1 and influences of this kinase upon cardiomyocyte structure and/or function are virtually nonexistent. Despite this dearth of cardiac-related knowledge, published studies of hematopoeitic and oncogenic cells suggest that the effects of PIM-1-mediated signaling are as significant and far reaching as those ascribed to PKC or Akt/PKB. Similarities between these kinases are readily apparent: 1) phosphorylation of serine/threonine residues in target substrates, 2) regulation of cell survival and/or proliferation, and 3) intriguing propensity for nuclear accumulation.[2-4] Between PIM-1 and Akt/PKB there are additional connections such as similar target substrate specificities, coordinate regulation of PIM-1 expression by Akt activation, and blunting of activation by treatment with the PI3-K inhibitor LY294002.[5-7] Collectively, this evidence implicates PIM-1 for an important role in myocardial signaling, and supportive findings documenting PIM-1 expression and function in cardiomyocytes are presented herein.

PIM-1 was originally identified as a proto-oncogene and subsequently found to be a highly conserved serine/threonine kinase. Unlike other serine/threonine kinases (e.g. Akt, MAPK, PKA or PKC), PIM-1 phosphotransferase activity is not regulated by upstream kinases—it is active in nascent translated form. Thus, PIM-1 activity is regulated by concerted control of gene transcription, mRNA translation, and protein degradation. The target phosphorylation consensus sequence for PIM-1 is found in proteins mediating transcription, cell growth, proliferation, and survival. While PIM-1 overexpression alone is not highly oncogenic, it does predispose cells to transformation upon exposure to mutagens.[8,9] In general, PIM-1 up-regulation enhances cell survival whereas loss of PIM-1 increases apoptotic cell death. The protective effect of PIM-1 is dependent upon kinase activity as borne out by experiments using a dominant negative kinase dead mutant construct.[10,11] Occasional exceptions wherein PIM-1 activity increases cell death seem to result from differences in the cellular backgrounds where PIM-1 was studied. Increased PIM-1 expression also associated with cellular differentiation[4,12,13] as well as proliferation.[14,15] Studies with myocardium demonstrate changes in PIM-1 expression during postnatal development and aging that form the basis of studies for this invention.

PIM-1 expression is stimulated by a variety of hormones, cytokines and mitogens, many of which are associated with cardioprotective signaling.[16,17] These multiple inductive stimuli lead to an accepted survival kinase in the myocardium: Akt/PKB. However, the connection of Akt-mediated effects to PIM-1 mediated signaling has been overlooked. In fact, expression of PIM-1 is increased by Akt activation[18] and studies using LY294002 to block PI3-K activity were also inadvertently inhibiting PIM-1 kinase activity as well.[5] Despite apparent parallels between PIM-1 and Akt, these kinases exhibit distinct effects in regulation of cell growth and survival.[6] PIM-1 shares homology with two related family members that have largely overlapping functions named PIM-2 and PIM-3. Parallels of signal transduction between PIM family members and Akt are a primary focus of ongoing research in non-myocyte cells.

Independent aspects of PIM-1 mediated signaling are waiting to be teased apart from overlaps with Akt using knockout mouse lines in conjunction with overexpression approaches, thereby providing new insight regarding regulation of myocardial survival and proliferation. Such studies with hematopoeitic cells have revealed that PIM and Akt are critical components of overlapping but independent signaling pathways responsible for enhancement of growth and survival.[6,7] Mouse lines engineered with deletion of PIM-1 or triple knockouts deficient for all PIM kinases are viable without severe phenotypic effects.[19] However, we have found cardiac-specific consequences following ischemia reperfusion damage in the PIM-1 knockout mouse line. This data validates the role of PIM-1 in response to and protection from cardiomyopathic challenge.

Fundamentals of PIM-1 signal transduction are predominantly based in studies of hematopoeitic and oncogenic cells where the kinase was first identified. PIM-1 is a downstream effector of many cytokines that operate through "Signal Transducers and Activators of Transcription" known by the STAT acronym. Both STAT3 or STATS bind directly to the PIM-1 promoter and induce expression.[20] PIM-1 expression is inhibited by negative feedback loop regulatory control of the Jak/STAT pathway through interaction with Suppressors Of Cytokine Signaling (also known as SOCS).[17] PIM-1 protein stability is also decreased through action of serine/threonine phosphatase PP2a.[21] Pivotal roles of STAT, SOCS, and PP2a signaling in the myocardium[22]-24 implicate PIM-1 as an attractive candidate effector molecule to mediate biological effects in cardiomyocytes.

The list of target molecules for PIM-1 kinase continues to accumulate new members every year, many of which regulate cell cycle progression and apoptosis. Regulation of cell cycle proliferation by PIM-1 in vascular smooth muscle cells confirms a role of PIM-1 in the cardiovascular system.[14] In the context of this proposal, the capacity of PIM-1 to inactivate pro-apoptotic Bad protein via phosphorylation and enhance Bcl-2 activity[7,25,26] is reminiscent of prior investigations of cardiomyocyte survival signaling.[27,28] The capacity of PIM-1 to inhibit apoptotic cell death by preserving mitochondrial integrity is a fundamental hypothesis in this proposal studied in Specific Aim 4. Removal/recycling of mitochondria and other intracellular organelles by autophagy is regulated in part by Akt-dependent signaling (reviewed in reference 29, below).

Recent advances support a central role for PIM kinases in proliferative and survival signaling. Cytokine-responsive gp130 signaling cascades lie directly upstream of PIM kinase activation,[30,31] yet extensive studies in the cardiovascular system have yet to explore the contribution of PIM to reported protective effects. Furthermore, intermingling of PIM and Akt-mediated effects are established[5-7] along with the pivotal role of Akt in the cardiovascular system, (reviewed in references 32 and 33, below) yet the contribution of PIM kinases in myocardial signaling remains virtually unknown. Specific Aim 3 is designed to tease apart the relationship of Akt and PIM in the myocardium. Results point to PIM as a pivotal regulator of proliferation and survival in the myocardium.

C. PIM-1 is Expressed in Cardiomyocytes Exposed to Cardioprotective Stimuli

PIM-1 is expressed in cardiomyocytes exposed to cardioprotective stimuli. Unlike Akt, PIM-1 is constitutively active and regulated by protein production/degradation rates. Constitutive low level production of PIM-1 is detectable in cardiomyocytes under basal conditions both in cultured cells as well as normal myocardium. We cultured neonatal rat cardiomyocytes, which we treated with IGF-1, PMA, dexamethasone, LIF, phenyl-ephedrine, endothelin-1, estradiol, and forskolin and then assayed for PIM-1 protein levels. The first four factors significantly increased PIM-1 expression, whereas little or no increase was seen with the others over a 2 hour period.

FIG. 1 illustrates immunoblots demonstrating that cardioprotective stimuli induces Pim-1 expression. Cultured neonatal rat cardiomyocytes were treated with various factors to increase Pim-1 protein level as indicated above each lane including IGF-1, PMA, dexamethasone, and forskolin. Induction is evident in response to IGF-1, PMA and dexamethasone, whereas forskolin has no discernable effect. Similarly, other stimuli including phenylephrine, endothelin-1, or estradiol did not markedly increase Pim-1 protein expression in this time frame of exposure, which was two hours.

PIM-1 is induced in cardiomyocytes in response to cardiomyopathic injury. Low level PIM-1 expression is markedly increased following cardiomyopathic challenge in hearts of mice subjected to either infarction by coronary occlusion or pressure overload resulting from transverse aortic constriction (TAC) at four days after procedures. In comparison, PIM-1 is concentrated within the nuclei of selected cardiomyocytes in chronic heart failure from a genetically engineered mouse model (tropomodulin overexpressing transgenic[34]). In all cases, PIM-1 protein level is elevated relative to sham-operated control mice. The elevation of PIM-1 under these circumstances is presumably mediated by paracrine cytokine signaling within the challenged myocardium.

Figure 2:
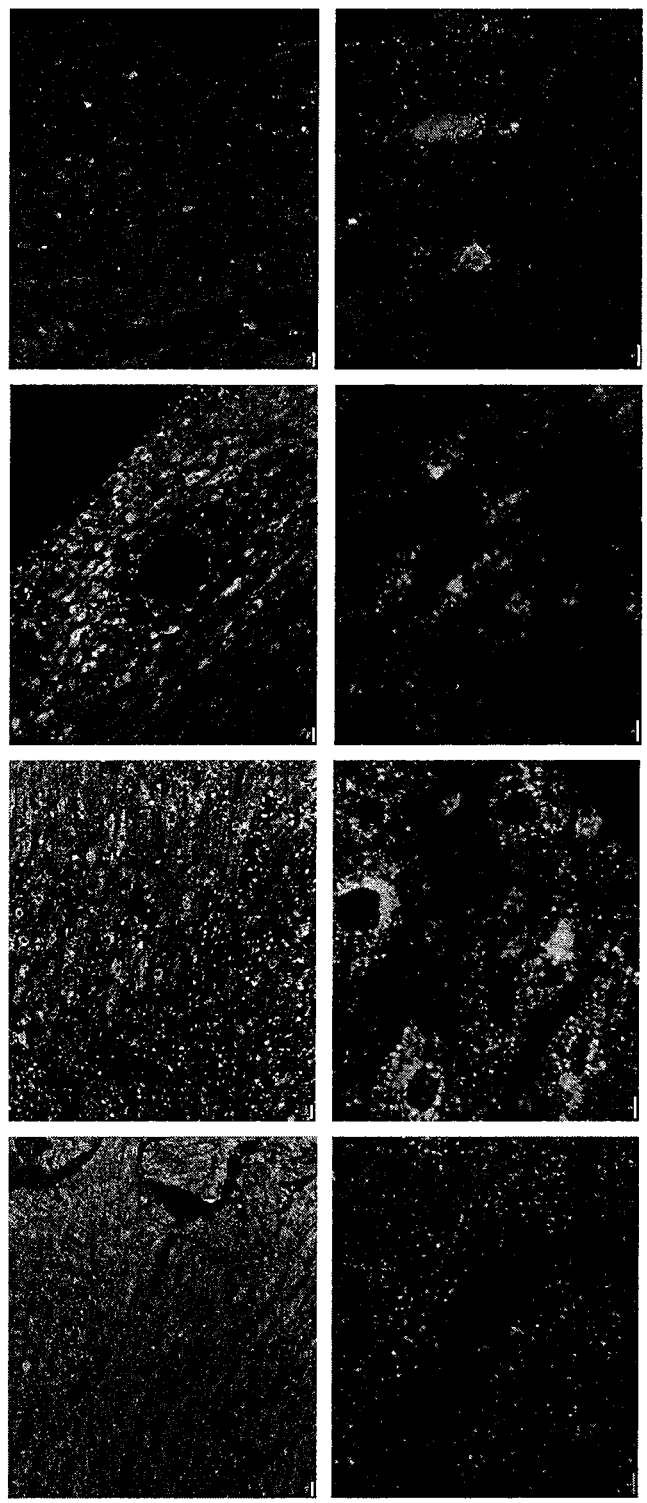
FIG. 2 illustrates confocal micrographs showing that cardiomyopathic stimuli induce Pim-1 expression in surviving myocardium: a widefield view is shown in the micrographs of the upper row, with selected regions is shown in higher magnification to reveal cellular detail is shown in the micrographs of the lower row, as described in detail in Example 2, below.

FIG. 2 illustrates confocal micrographs showing that cardiomyopathic stimuli induce Pim-1 expression in surviving myocardium. Confocal micrographs show induction of Pim-1 protein expression relative to sham-operated controls (Sham) in response to acute myocardial injury induced four days after infarction in the border zone (MI) or near vasculature after pressure overload after four days (TAC). Both acute injury models show accumulation of Pim-1 in perinuclear areas, whereas a genetically engineered transgenic model of chronic dilated cardiomyopathy shows Pim-1 accumulation within select nuclei (TOT). Sections were labeled with antibody to Pim-1 (green), phalloidin to decorate actin filaments (red), and TOPRO dye for nuclei (blue). Widefield view (upper row) with selected regions shown in higher magnification to reveal cellular detail (lower row).

Loss of PIM-1 signaling impairs functional recovery following ischemia-reperfusion injury. Genetically engineered mouse lines lacking PIM-1 or a triple knockout lacking PIM-1, 2, and 3 created as described[19] have been established in our colony. Hearts from these mice were subjected to ex vivo treatment[35] leading to ischemia-reperfusion damage. Functional recovery of the PIM-knockout lines was significantly impaired relative to age, strain, and gender-matched control hearts. Hemodynamic recovery of the triple knockout line was comparable to that of the single isoform PIM-1 knockout line, indicating that the PIM-1 isoform is the critical member of the PIM family to mediate protective signaling in response to ischemia-reperfusion challenge.

FIG. 3 graphically illustrates data showing that Pim-1 preserves hemodynamic function in ischemia-reperfusion injury. Hearts harvested from mouse normal (FVB, green or upper line) as well as genetically engineered lines lacking Pim-1 (PIM-1 ko, pink or lower line) or Pim-1, 2, and 3 (PIM 1, 2, 3 ko; blue or middle line) were subjected to ischemia reperfusion challenge and hemodynamic recovery of function was assessed as previously described.[32] Pim knockout mouse lines show significant impairment ($p<0.01$ for time points beyond one hour of reperfusion).

PIM-1 expression is developmentally regulated in postnatal growth. Elevation of PIM-1 in postnatal development is consistent with our observation that PIM-1 promotes growth and proliferation of cardiomyocytes in the postnatal heart. In addition, we have also observed PIM-1 expression in cardiac progenitor cells of adult hearts coincident with c-kit and Sca-1 stem cell markers. Correlation of PIM-1 expression in stem cell populations would be consistent with observations from hematopoeitic cell biology demonstrating PIM-1 plays a role in proliferation and survival.[6,19]

Figure 4:
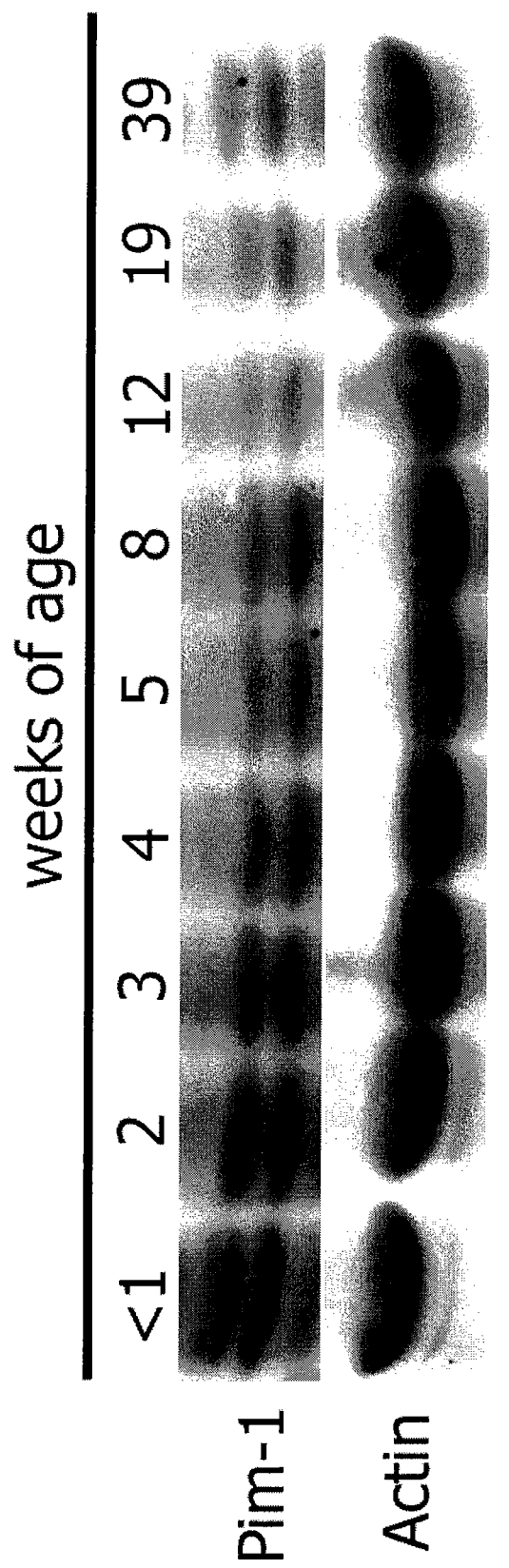
FIG. 4 illustrates immunoblots demonstrating Pim-1 expression is highest in postnatal hearts and decreases with age, as described in detail in Example 2, below.

FIG. 4 illustrates immunoblots demonstrating Pim-1 expression is highest in postnatal hearts and decreases with age. Immunoblot showing Pim-1 protein expression at the indicated weeks after birth: data including samples from less than one week, and 2, 3, 4, 5, 8, 12, 19 and 39 weeks of age. Actin is shown as a loading control to verify comparable protein sample concentration between lanes.

PIM-1 is expressed by recombinant adenoviral vectors. Overexpression of PIM-1 or dominant-negative PIM-1 lacking kinase activity has been accomplished by creation of adenoviral vectors. We have engineered these constructs with GFP fluorescent tags to track their expression without the need for anti-PIM-1 antibodies, allowing to directly visualize exogenous protein expression. These constructs have been valuable for understanding the effects of PIM-1 accumulation in cardiomyocytes.

Figure 5:
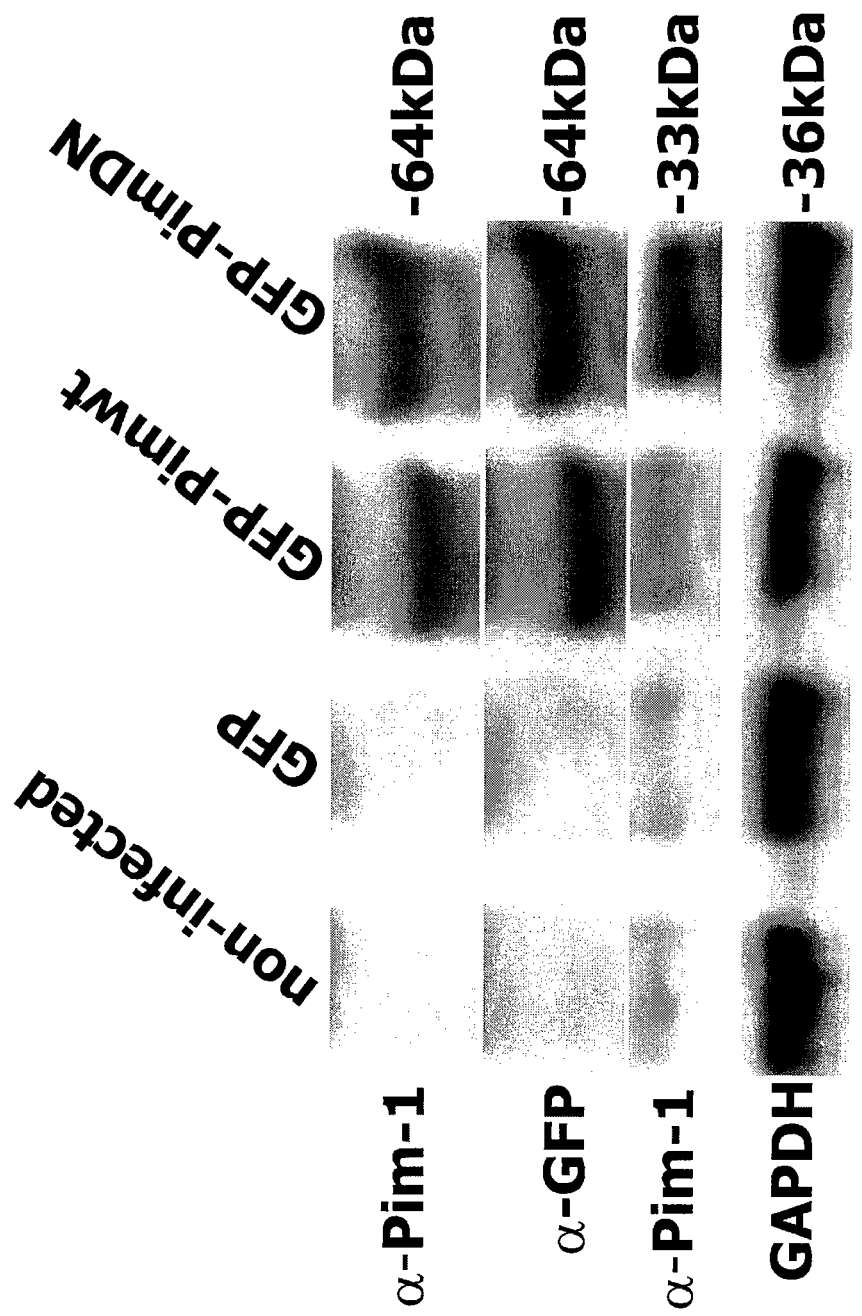
FIG. 5 illustrates immunoblots demonstrating Pim-1 expression in cardiomyocytes from recombinant adenoviral vectors, as described in detail in Example 2, below.

FIG. 5 illustrates immunoblots demonstrating Pim-1 expression in cardiomyocytes from recombinant adenoviral vectors. Cardiomyocytes were infected (or not infected, noting the "non-infected" control) with GFP-tagged constructs of Pim-1 in wild-type (GFP-Pimwt) or kinase-dead (GFP-PimDN) forms (and GFP only). Apparent mobility of GFP-fusion constructs (~65 kDa) differs from native Pim-1 (approximately 33 kDa). Note induction of native Pim-1 resulting from overexpression of GFP-PimDN, presumably as a compensatory mechanism. GAPDH shown to demonstrate comparable loadings between lysates.

PIM-1 overexpression protects against apoptotic challenge with doxorubicin. Overexpression of PIM-1 in cultured cardiomyocytes inhibits apoptosis resulting from exposure to doxorubicin as measured by TUNEL labeling. Neonatal rat cardiomyocyte cultures were infected with recombinant adenoviruses expressing GFP, PIM-1 wild-type (PIMwt), or PIM-1 dominant negative (DN) overnight prior to apoptotic stimulation with doxorubicin. With reference to FIG. 1, non-infected cells (NI) or GFP-expressing cells show comparable TUNEL labeling following doxorubicin treatment, whereas PIMwt expressing cells show significant reductions of TUNEL positive nuclei ($p<0.05$). Cells expressing the DN construct show enhanced TUNEL labeling. In contrast, the mutant kinase-dead PIM-1 construct accumulates to lower protein levels than PIM-1 wild-type, yet significantly increases apoptosis compared to GFP-expressing control cells.

Figure 6:
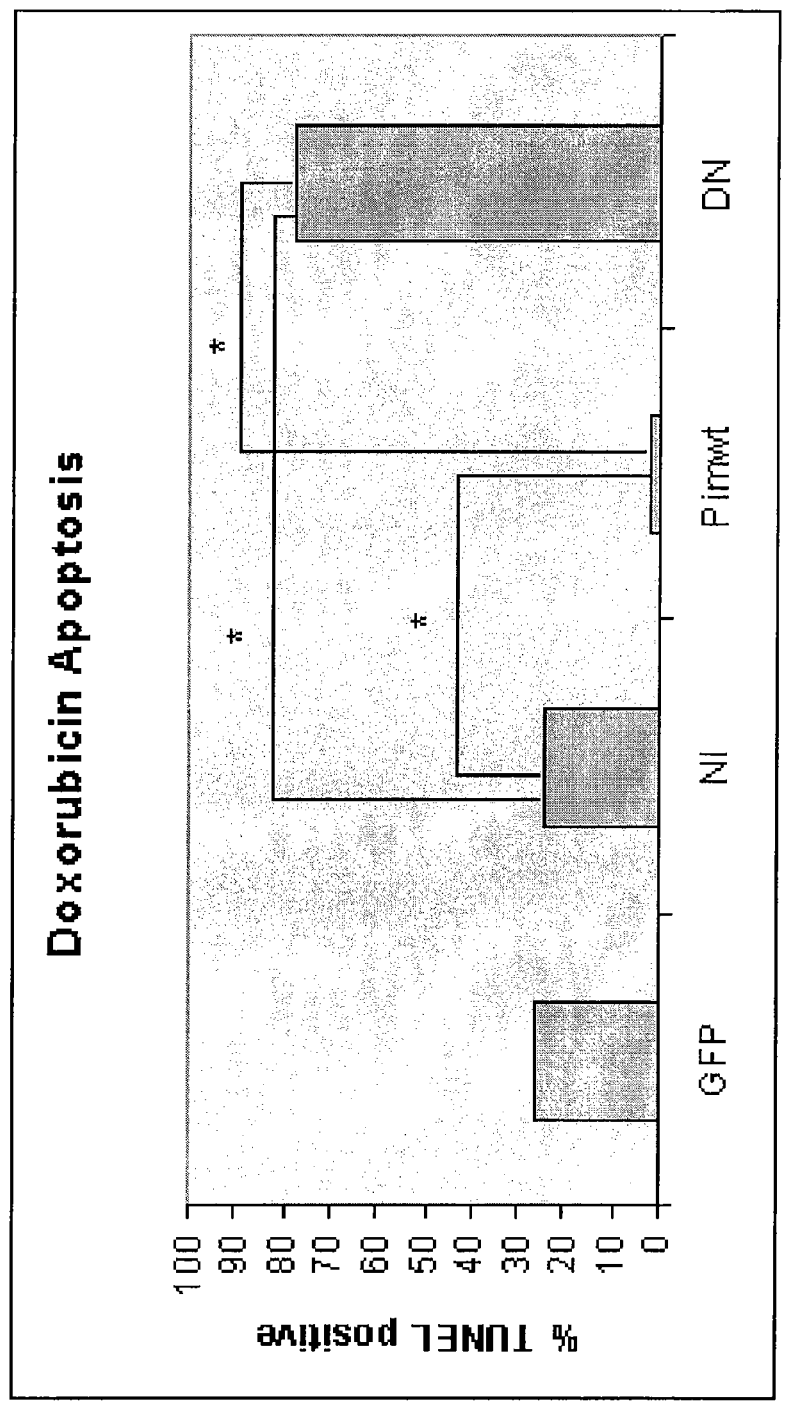
FIGS. 6 and 7 show how Pim-1 inhibits apoptosis in cardiomyocytes.
Figure 7:
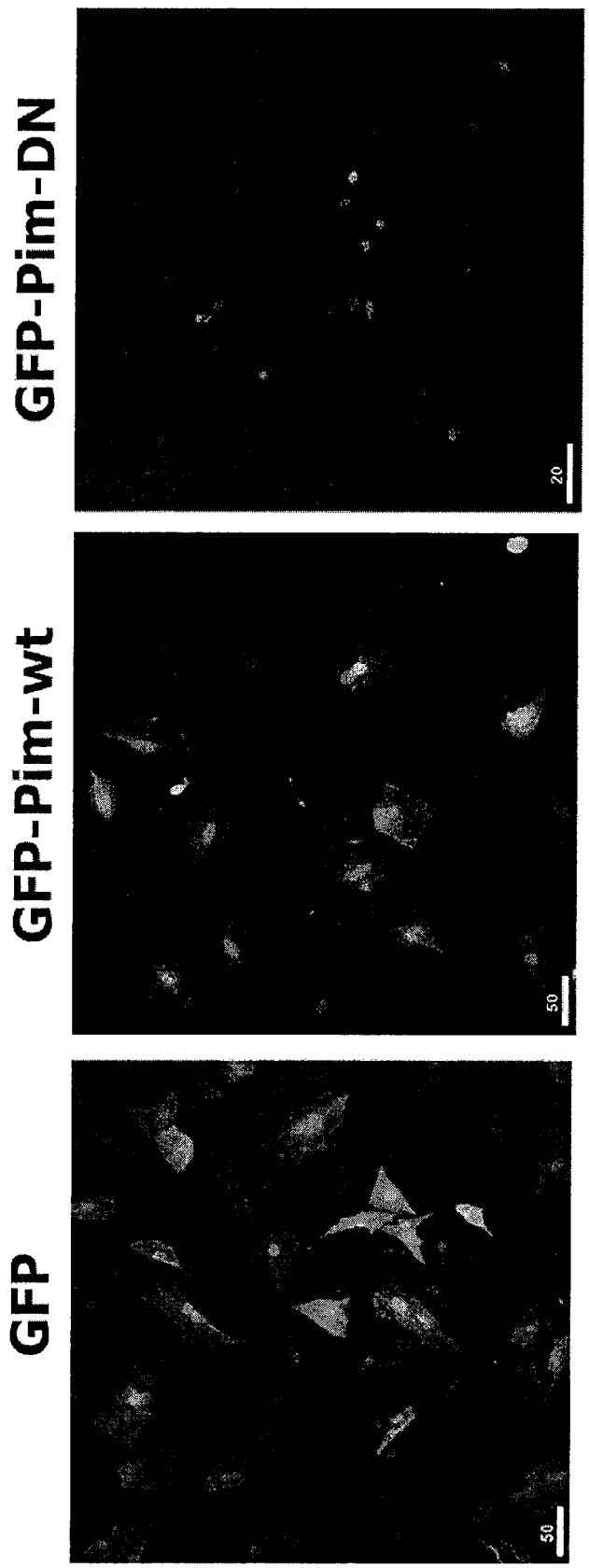

FIGS. 6 and 7 show how Pim-1 inhibits apoptosis in cardiomyocytes. Neonatal rat cardiomyocyte cultures were infected with recombinant adenoviruses expressing GFP, Pim-1 wild-type (Pimwt), or Pim-1 dominant negative (DN) overnight prior to apoptotic stimulation with doxorubicin. As graphically summarized in FIG. 6, non-infected cells (NI) or GFP-expressing cells show comparable TUNEL labeling following doxorubicin treatment, whereas Pimwt expressing cells show significant reductions of TUNEL positive nuclei ($p<0.05$). FIG. 7 illustrates a micrograph demonstrating that cells expressing the DN construct show enhanced TUNEL labeling; while FIG. 6 shows quantitative results, the FIG. 7 panels illustrate representative fields of infected cardiomyocytes showing GFP fluorescence (green) overlay with actin filaments revealed by phalloidin (red) in GFP only, GFP-Pim-wt and GFP-Pim-DN samples.

Figure 8:
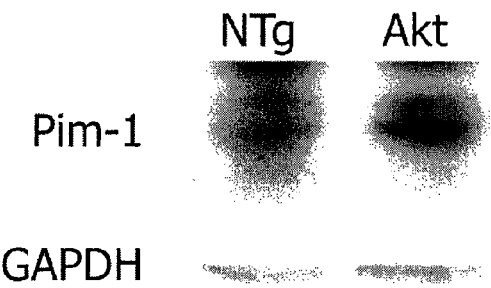
FIGS. 8A and 8B illustrate that nuclear accumulation of Akt induces expression of Pim-1 kinase in the myocardium: Immunoblot (FIG. 8A) and confocal microscopy (FIG. 8B) of sections from 6 month old normal (NTG) and transgenic mice expressing cardiac-specific nuclear-targeted Akt; a separated grayscale images in scans correspond to pim-1, actin, and nuclei that correspond to the overlay colors of green, red, and blue respectively, as described in detail in Example 2, below.
Figure 8:
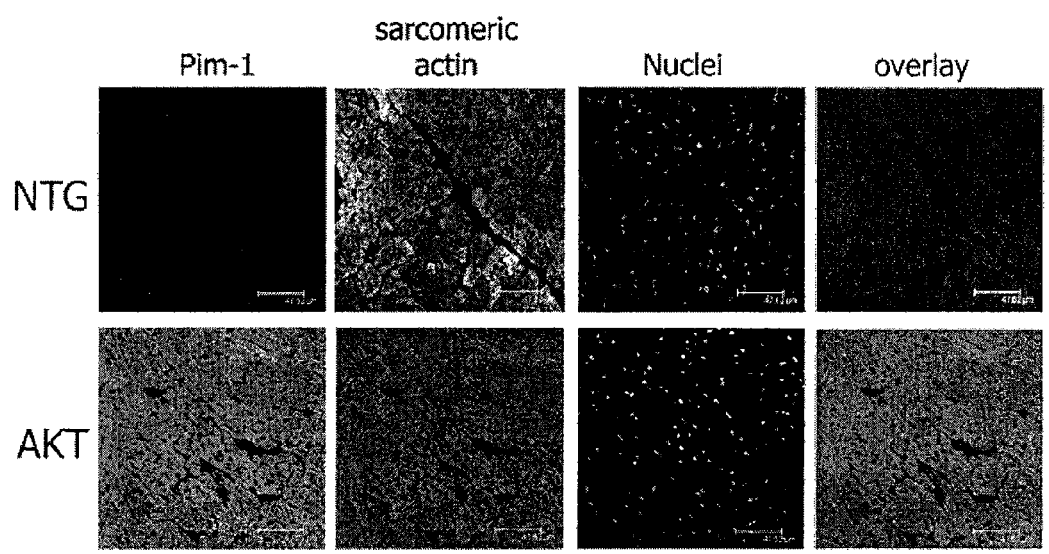

PIM-1 overexpression promotes anti-apoptotic signaling via cascades involving Bcl-2 family members as well as Mdm2. Overexpression of PIM-1 increases accumulation of Bcl-2 and Bcl-XL family members, both of whom antagonize intrinsic apoptotic signaling by preserving mitochondrial integrity, as illustrated in FIG. 8A. Additional signaling to promote survival induced by PIM-1 includes accumulation of Mdm2 and phosphorylation of Bad. Mdm2 antagonizes p53-dependent cell death[36] and Bad phosphorylation inhibits the pro-apoptotic action of this protein.[26] Thus, PIM-1 impacts upon cell survival by promoting the anti-apoptotic action of Bcl-2 family members as well as enhancing Mdm2.

PIM-1 expression is induced by nuclear accumulation of activated Akt. Induction of PIM-1 promoter activity by Akt kinase indicates that PIM-1 expression lies downstream of Akt activation.[18] This observation has now been validated in both transgenic mouse hearts expressing nuclear-targeted Akt (as illustrated in FIG. 8B) as well as cultured cardiomyocytes infected with an adenoviral vector expressing nuclear-targeted Akt.

In summary, FIGS. 8A and 8B illustrate that nuclear accumulation of Akt induces expression of Pim-1 kinase in the myocardium: Immunoblot (FIG. 8A) and confocal microscopy (FIG. 8B) of sections from 6 month old normal (NTG) and transgenic mice expressing cardiac-specific nuclear-targeted Akt.[38] Separated grayscale images in scans correspond to pim-1, actin, and nuclei that correspond to the overlay colors of green, red, and blue respectively.

Nuclear accumulation of Akt promotes increased PIM-1 expression detectable by both immunofluorescence as well as immunoblot analyses. The implications of this result are profound for survival signaling in the myocardium, since inhibition of Akt activation would also lead to reduction in PIM-1 levels. Furthermore, pharmacologic treatment with LY294002 that has traditionally been used for inhibition of Akt also inhibits PIM-1 kinase activity.[5] These findings provide strong circumstantial evidence that the protective effects previously ascribed to Akt activation may be due, in part, to actions of PIM-1 kinase. Since the role for PIM-1 in myocardial signaling has been overlooked to date, important aspects of cardiac Akt biology related to cell survival and growth need reassessment.

Figure 9:
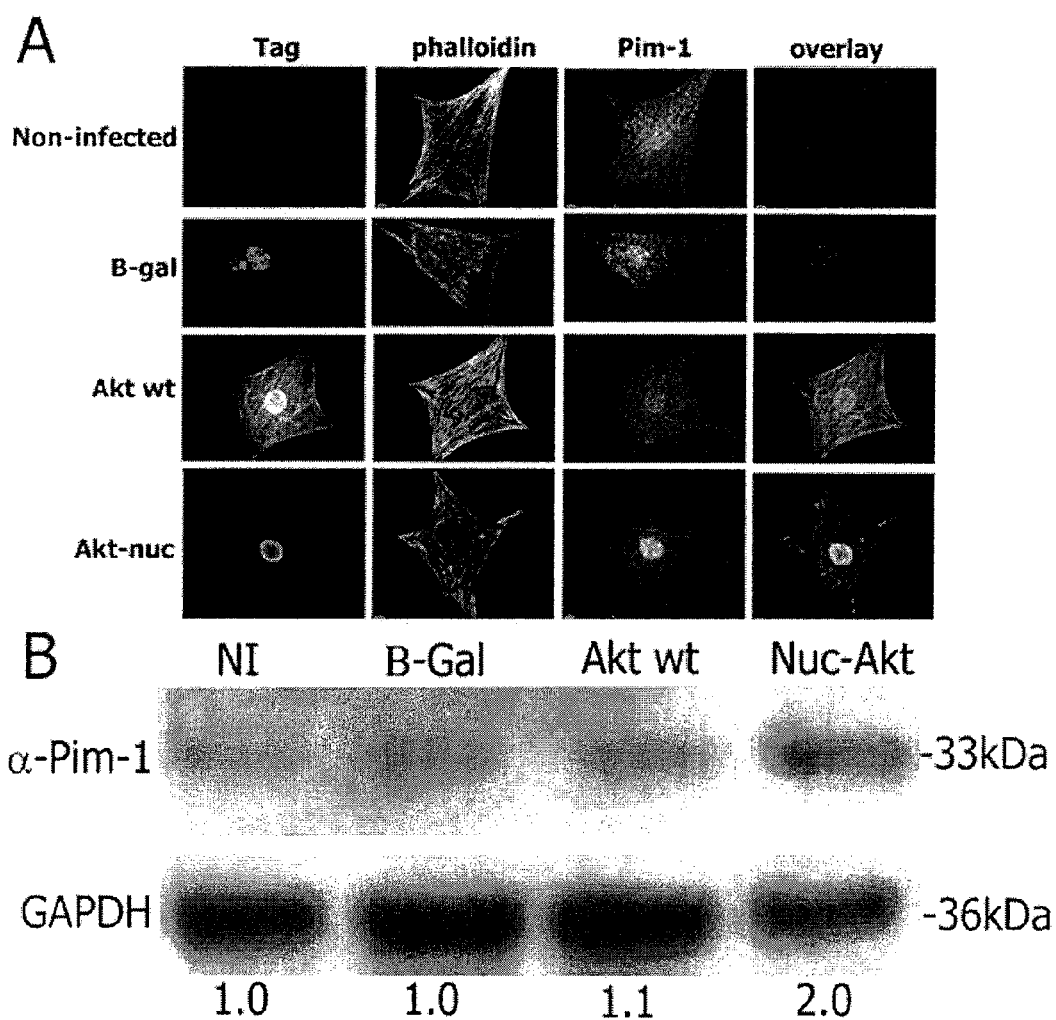
FIG. 9 illustrates that nuclear accumulation of Akt induces Pim-1 expression.

FIG. 9 illustrates that nuclear accumulation of Akt induces Pim-1 expression. FIG. 9(A) illustrates a confocal microscopy of cultured cardiomyocytes infected with adenoviruses expressing nuclear-targeted β-galactosidase (B-gal), Akt wild-type (Akt wt), or nuclear targeted Akt (Akt-nuc) detected with myc-tag antibody (Tag). Adenovirally encoded proteins are green in overlay. Nuclear-targeted Akt promotes accumulation of Pim-1 in the nucleus (shown blue in overlay). Phalloidin shows actin filaments (red in overlay). FIG. 9(B) illustrates an immunoblot blot showing increased Pim-1 expression in cardiomyocyte cells infected with adenovirus encoding nuclear-targeted Akt (Akt-nuc). GAPDH is shown to show comparable loading between samples.

Loss of PIM-1 activity results in compensatory elevation of Akt. Previously documented overlaps between PIM-1 and Akt in terms of functional effects and crosstalk warrant further investigation to determine the role of PIM-1 kinase in myocardial biology. Experiments using adenoviruses expressing PIM-1 in either wild-type or dominant negative forms demonstrate that loss of PIM-1 signaling leads to elevation of Akt protein expression and activity. Similarly, immunoblot evaluation of the PIM-1 knockout line shows increased levels of phospho-Akt$^{473}$ as well as total Akt protein (data not shown). The basis for this induction of Akt expression may lie with compensatory signaling to counterbalance loss of downstream PIM-1 activity. Since dominant negative PIM-1 is capable of enhancing cell death, as illustrated in FIG. 10, our data are consistent with the conclusion that PIM-1 mediates certain facet(s) of survival signaling in the Akt cascade.

Figure 10:
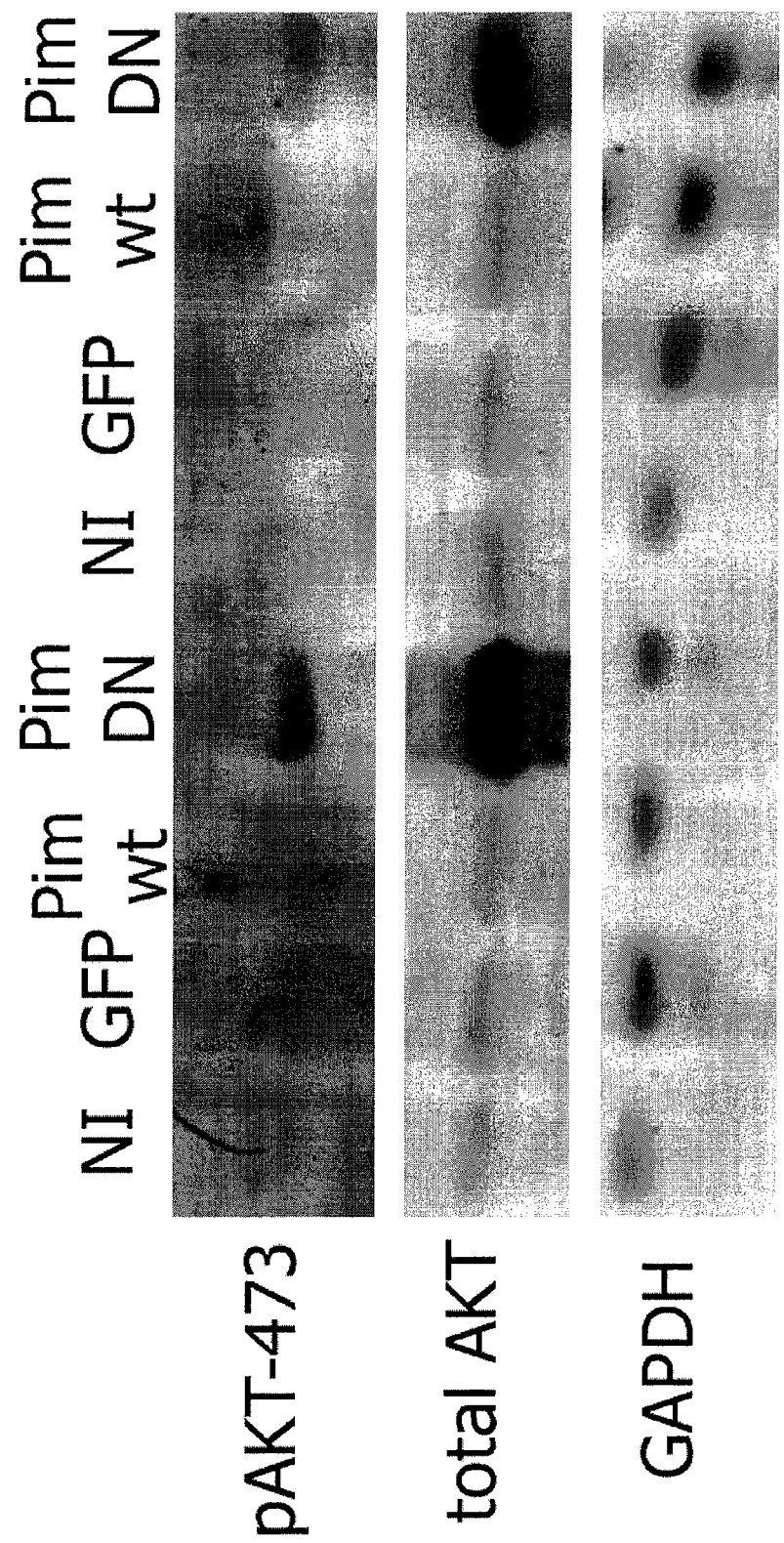
FIG. 10 illustrates an immunoblot blot showing expression of dominant negative Pim-1 prompts Akt accumulation in cardiomyocytes; immunoblot shows infection of neonatal rat cardiomyocytes with adenoviruses expressing Pim-1 in either wild type (wt) or dominant-negative (DN) forms, as described in detail in Example 2, below.

In summary, FIG. 10 illustrates an immunoblot blot showing expression of dominant negative Pim-1 prompts Akt accumulation in cardiomyocytes. Immunoblot showing infection of neonatal rat cardiomyocytes with adenoviruses expressing Pim-1 in either wild type (wt) or dominant-negative (DN) forms. Levels of phospho-Akt$^{473}$ as well as total Akt protein levels are elevated in lysates prepared from the cells expressing DN Pim-1. Two separate sets of experimental results are shown with controls of uninfected cells (NI), GFP-expressing cells (GFP), and GAPDH loading controls to standardize for variation in protein loading between samples.

Figure 11:
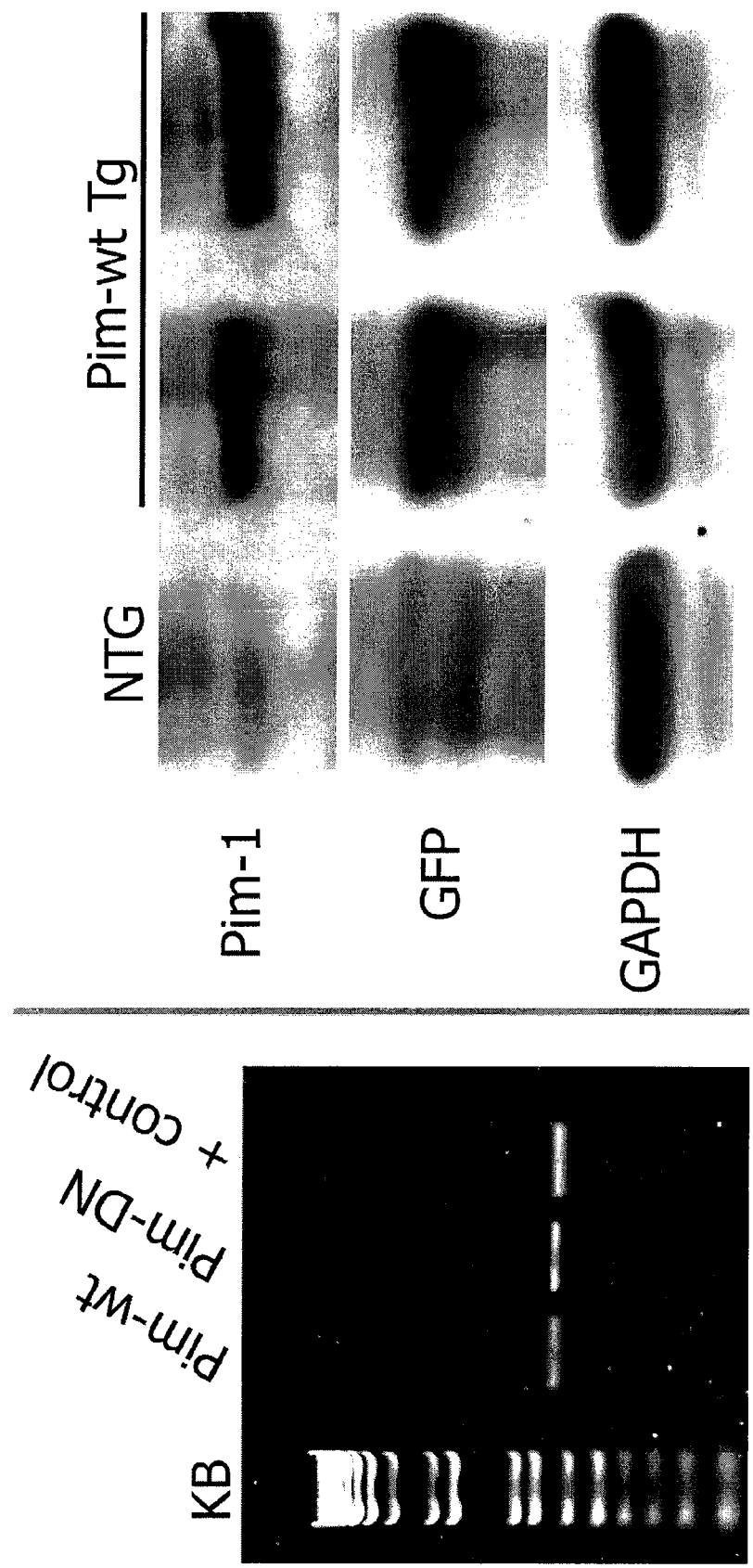
FIG. 11 illustrates data characterizing founder lines and protein expression in Pim-1 transgenic mice.

FIG. 11 illustrates data characterizing founder lines and protein expression in Pim-1 transgenic mice. PCR of genomic DNA samples (FIG. 11 left) and immunoblot of cardiac lysates (FIG. 11 right). Confirmation of vertical transmission of the cardiac-specific Pim-1 wild-type (wt) as well as dominant-negative (DN) transgene is confirmed in samples from the F1 generation. An immunoblot of cardiac lysates from the Pim-1 wt transgenic line shows accumulation of Pim-1 and GFP with coincident mobility at approximately 60 kDa (resulting from Pim-1 with a GFP-tag) indicative of substantial transgene expression in these 6 week old mouse hearts. GAPDH shown to indicate comparable loading of samples between lanes.

LITERATURE CITED

EXAMPLE 2

1) Sussman M A and Anversa P. Myocardial again and senescence: where have the stem cells gone? Ann. Rev. Physiol. 2004; 66: 29-48.
2) Bachmann M and Moroy T. The serine/threonine kinase PIM-1. Int J Biochem Cell Biol. 2005; 37: 726-730.
3) Neri L M, Borgatti P, Capitani S, Martelli A M. The nuclear phosphoinositide 3-kinase/AKT pathway: a new second messenger system. Biochim Biophys Acta. 2002; 1584:73-80.
4) Wang Z, Bhattacharya N, Weaver M, Petersen K, Meyer M, Gapter L and Magnuson N S. PIM-1: a serine/threonine kinase with a role in cell survival, proliferation, differentiation, and tumorigenesis. J Vet Sci. 2001; 2: 167-179.
5) Jacobs M D, Black J, Futer O, Swenson L, Hare B, Fleming M and Saxena K. PIM-1 ligand-bound structures reveal the mechanism of serine/threonine kinase inhibition by LY294002. J Biol. Chem. 2005; 280: 13728-13734.
6) Hammerman P S, Fox C J, Birnbaum M J, Thompson C B. PIM and Akt oncogenes are independent regulators of hematopoietic cell growth and survival. Blood. 2005; 105: 4477-83.
7) Fox C J, Hammermann, Cinalli R M, Master S R, Chodosh L A and Thompson C B. The serine/threonine kinase PIM-2 is a transcriptionally regulated apoptotic inhibitor. Genes & Dev. 2003; 17: 1841-1854.
8) Bachmann M, Hennemann H, Xing P X, Hoffmann I and Moroy T. The oncogenic serine/threonine kinase PIM-1 phosphorylates and inhibits the activity of Cdc25C-associated kinase 1 (C-TAK1). J Biol. Chem. 2004; 279: 48319-48328.
9) Roh M, Gary B, Song C, Said-Al-Naief N, Tousson A, Kraft, Eltoum I-E and Abdulkadir S A. Overexpression of the oncogenic kinase PIM-1 leads to genomic instability. Cancer Res. 2003; 63: 8079-8084.
10) Lilly M, Sandholm J, Cooper J J, Kosikinen P J and Kraft A. The PIM-1 serine kinase prolongs survival and inhibits apoptosis-related mitochondrial dysfunction in part through a bcl-2-dependent pathway. Oncogene 1999; 18: 4022-4031.
11) Kim K T, Baird K, Ahn J Y, Meltzer P, Lilly M, Levis M and Small D. PIM-1 is up-regulated by constitutively activated FLT3 and plays a role in FLT3-mediated survival. Blood 2005; 105: 1759-1767.
12) Zippo A, De Robertis A, Bardelli M, Galvagni F, Oliviero S. Identification of Flk-1 target genes in vasculogenesis: PIM-1 is required for endothelial and mural cell differentiation in vitro. Blood. 2004; 103:4536-44.
13) Aho T L, Lund R J, Ylikoski E K, Matikainen S, Lahesmaa R, Koskinen P J. Expression of human PIM family genes is selectively up-regulated by cytokines promoting T helper type 1, but not T helper type 2, cell differentiation. Immunology. 2005; 116: 82-8.
14) Katakami N, Kaneto H, Hao H, Umayahara Y, Fujitani Y, Sakamoto K, Gorogawa, S, Yasuda T, Kawamori D, Kajimoto Y, Matsuhisa M, Yutani C, Hori M and Yamasaki Y. Role of PIM-1 in smooth muscle cell proliferation. J Biol. Chem. 2004; 279: 54742-54749.
15) Bhattacharya N, Wang Z, Davitt C, McKenzie I F C, Xing P-X and Magnuson N S. PIM-1 associates with protein complexes necessary for mitosis. Chromosoma 2002; 111: 80-95.
16) White E. The PIMs and outs of survival signaling: role for the PIM-1 protein kinase in the suppression of apoptosis by cytokines. Gene & Dev. 2003; 17: 1813-1816.
17) Chen X P, Losman J A, Cowan S, Donahue E, Fay, S, Vuong B Q, Nawjin M C, Capece D, Cohan V L and Rothman P. PIM serine/threonine kinases regulate the stability of Socs-1 protein. Proc Nat Acad. Sci. 2002; 99: 2175-2180.
18) Krishnan N, Pan H, Buckley D J, Buckley A. Prolactin-regulated PIM-1 transcription: identification of critical promoter elements and Akt signaling. Endocrine 2003; 20:123-30.
19) Mikkers H, Nawijn M, Allen J, Brouwers C, Verhoeven E, Jonkers J and Berns A. Mice deficient for all PIM kinases display reduced body size and impaired responses to hematopoetic growth factors. Mol Cell Biol. 2004; 24: 6104-6115.
20) Losman J A, Chen X P, Vuong B Q, Fay S, Rothman P B. Protein phosphatase 2A regulates the stability of PIM protein kinases. J Biol. Chem. 2003; 278:4800-4805.
21) Peltola K J, Paukku K, Aho T L T, Ruuska M, Silvennoinen O and Koskinen P J. PIM-1 kinase inhibits STAT-5-dependent transcription via its interactions with SOCS1 and SOCS3. Blood. 2004; 103: 3744-3750.
22) Kunisada K, Negoro S, Tone E, Funamoto M, Osugi T, Yamada S, Okabe M, Kishimoto T and Yamauchi-Takihara K. Signal transducer and activator of transcription 3 in the heart transduces not only a hypertrophic signal but a protective signal against doxorubicin-induced cardiomyopathy. Proc Natl Acad Sci USA. 2000; 97: 315-9.
23) Yasukawa H, Yajima T, Duplain H, Iwatate M, Kido M, Hoshijima M, Weitzman M D, Nakamura T, Woodard S, Xiong D, Yoshimura A, Chien K R, Knowlton K U. The suppressor of cytokine signaling-1 (SOCS1) is a novel therapeutic target for enterovirus-induced cardiac injury. J Clin Invest. 2003; 111: 469-78.
24) Brewis N, Ohst K, Fields K, Rapacciuolo A, Chou D, Bloor C, Dillmann W, Rockman H, Walter G. Dilated cardiomyopathy in transgenic mice expressing a mutant A subunit of protein phosphatase 2A. Am J Physiol Heart Circ Physiol. 2000; 279: H1307-18.
25) Yan B, Zemskova M, Holder S, Chin V, Kraft A, Koskinen P J and Lilly M. The PIM-2 kinase phosphorylates BAD on Serine 112 and reverses BAD-induced cell death. J Biol. Chem. 2003; 278: 45358-45367.
26) Aho T L T, Sandholm J, Peltola K J, Mankonen H P, Lilly M and Koskinen P J. PIM-1 kinase promotes inactivation of the pro-apoptotic Bad protein by phosphorylating it on the Ser112 gatekeeper site. FEBS Lett. 2004; 571: 43-49.
27) Uchiyama T, Engelman R M, Maulik N, Das D K. Role of Akt signaling in mitochondrial survival pathway triggered by hypoxic preconditioning. Circulation. 2004; 109: 3042-3049.
28) Kato K, Yin H, Agata J, Yoshida H, Chao L, Chao J. Adrenomedullin gene delivery attenuates myocardial inf- 29) Lum J J, DeBerardinis R J, Thompson C B. Autophagy in metazoans: cell survival in the land of plenty. Nat Rev Mol Cell Biol. 2005; 6: 439-48.
30) Shirogane T, Fukada T, Muller J M, Shima D T, Hibi M, Hirano T. Synergistic roles for PIM-1 and c-Myc in STAT3-mediated cell cycle progression and antiapoptosis. Immunity 1999; 11: 709-19.
31) Hirano T, Ishihara K, Hibi M. Roles of STAT3 in mediating the cell growth, differentiation and survival signals relayed through the IL-6 family of cytokine receptors. Oncogene 2000; 19: 2548-56.
32) Matsui T and Rosenzweig A. Convergent signal transduction pathways controlling cardiomyocyte survival and function: the role of PI 3-kinase and Akt. J Mol Cell Cardiol. 2005; 38: 63-71.
33) Latronico M V, Costinean S, Lavitrano M L, Peschle C, Condorelli G. Regulation of cell size and contractile function by AKT in cardiomyocytes. Aim N Y Acad. Sci. 2004; 1015: 250-60.
34) Sussman M A, Welch S, Cambon N, Klevitsky R, Hewett T, Price R L, Witt S A and Kimball T R. Myofibril degeneration caused by tropomodulin overexpression in juvenile mice leads to dilated cardiomyopathy. J. Clin. Invest. 1998; 101, 51-61.
35) Morrison L E, Whittaker R J, Klepper R E, Wawrousek E F, Glembotski C C. Roles for alphaB-crystallin and HSPB2 in protecting the myocardium from ischemia-reperfusion-induced damage in a KO mouse model. Am J Physiol Heart Circ Physiol. 2004; 286: H847-55.
36) Yang Y, Li C C, Weissman A M. Regulating the p53 system through ubiquitination. Oncogene. 2004; 23: 2096-106.
37) Shioi T, McMullen J R, Kang P M, Douglas P S, Obata T, Franke T F, Cantley L C, Izumo S. Akt/protein kinase B promotes organ growth in transgenic mice. Mol Cell Biol. 2002; 22: 2799-2809.
38) Matsui T, Li L, Wu J C, Cook S A, Nagoshi T, Picard M H, Liao R, Rosenzweig A. Phenotypic spectrum caused by transgenic overexpression of activated Akt in the heart. J Biol. Chem. 2002; 277: 22896-22901.
39) Condorelli G, Drusco A, Stassi G, Bellacosa A, Roncarati R, Iaccarino G, Russo M A, Gu Y, Dalton N, Chung C, Latronico M V, Napoli C, Sadoshima J, Croce C M, Ross J, Jr. Akt induces enhanced myocardial contractility and cell size in vivo in transgenic mice. Proc Natl Acad Sci USA. 2002; 99: 12333-12338.
40) Shiojima I, Yefremashvili M, Luo Z, Kureishi Y, Takahashi A, Tao J, Rosenzweig A, Kahn C R, Abel E D, Walsh K. Akt signaling mediates postnatal heart growth in response to insulin and nutritional status. J Biol. Chem. 2002; 277:37670-37677.
41) Shiraishi I, Melendez, J, Ahn Y, Welch S, Schaefer E, Walsh K, Rosenzweig A, Kajstura J, Leri A, Anversa P and Sussman M A. Nuclear targeting of Akt enhances kinase activity and survival of cardiomyocytes. Circ Res. 2004; 94: 884-891.
42) Camper-Kirby D, Welch S, Walker A, Setchell K D R, Schaefer E, Kajstura J, Anversa P and Sussman M A. Myocardial Akt activation and gender: increased nuclear activity in females versus males. Circ. Res. 2001; 88: 1020-1027.
43) Welch S, Plank D, Witt S, Glascock B, Chimenti S, Andreoli A M, Limana F, Leri A, Kajstura J, Anversa P and Sussman M A. Cardiac-specific IGF-1 expression attenuates dilated cardiomyopathy in Tropomodulin Overexpressing Transgenic mice. Circ Res. 2002; 90: 649-656.
44) Kato T, Muraski J, Chen Y, Tsujita Y, Wall J, Glembotski C C, Schaefer E, Beckerle M and Sussman M A. Atrial natriuretic peptide promotes cardiomyocyte survival by cGMP-dependent nuclear accumulation of zyxin and Akt. J Clin Invest 2005; in press.
45) Krishnamurthy J, Torrice C, Ramsey M R, Kovalev G I, Al-Regaiey K, Su L, Sharpless N E. Ink4a/Arf expression is a biomarker of aging. J Clin Invest. 2004; 114:1299-1307.
46) Peng X D, Xu P Z, Chen M L, Hahn-Windgassen A, Skeen J, Jacobs J, Sundararajan D, Chen W S, Crawford S E, Coleman K G, Hay N. Dwarfism, impaired skin development, skeletal muscle atrophy, delayed bone development, and impeded adipogenesis in mice lacking Akt1 and Akt2. Genes Dev. 2003; 17:1352-1365.
47) Cho H, Thorvaldsen J L, Chu Q, Feng F, Birnbaum M J. Akt1/PKBalpha is required for normal growth but dispensable for maintenance of glucose homeostasis in mice. J Biol. Chem. 2001; 276: 38349-52.
48) Grunweller A, Gillen C, Erdmann V A and Kurreck J. Cellular uptake and localization of a Cy-3-labeled siRNA specific for the serine/threonine kinase PIM-1. Oligonucleotides. 2003; 13: 345-352.
49) Sussman M A, Welch S, Gude N, Khoury P R, Daniels S R, Kirkpatrick D, Walsh R A, Price R L, Lim H W and Molkentin J D. Pathogenesis of dilated cardiomyopathy: molecular, structural, and population analyses in Tropomodulin Overexpressing Transgenics. Am. J. Pathol. 2005; 155: 2101-2113.
50) Tsujita Y, Kato T and Sussman M A. Evaluation of Left Ventricular Function in Cardiomyopathic Mice by Tissue Doppler and Color M-mode Doppler Echocardiography. Echocardiography 2005; 22: 245-253.
51) Sussman M A, Welch S, Cambon N, Klevitsky R, Hewett T, Price R L, Witt S A and Kimball T R. Myofibril degeneration caused by tropomodulin overexpression in juvenile mice leads to dilated cardiomyopathy. J. Clin. Invest. 1998, 101, 51-61.
52) Sanbe A, Gulick J, Hanks M C, Liang Q, Osinska H, and Robbins J. Reengineering inducible cardiac-specific transgenesis with an attenuated myosin heavy chain promoter. Circ Res. 2003; 92: 609-616.
53) Sohal D S, Nghiem M, Crackower M A, Witt S A, Kimball T R, Tymitz K M, Penninger J M, and Molkentin J D. Temporally regulated and tissue-specific gene manipulations in the adult and embryonic heart using a tamoxifen-inducible Cre protein. Circ Res. 2001; 89: 20-25.
54) Schiekofer S, Shiojima I, Sato K and Walsh K. Microarray cDNA profiles of acute and chronic Akt1 activation in transgenic mouse hearts reveal gene expression profiles associated with compensatory hypertrophy and failure. Circulation 2003; 108 (supplement); IV-77.
55) Jin Z Q, Goetzl E J and Karliner J S. Sphingosine kinase activation mediates ischemic preconditioning in murine heart. Circulation 110 2004; 110: 1980-1989.
56) Karliner J S, Honbo N, Summers K, Gray M O and Goetzl E L. The lysophospholipids sphingosine-1-phosphate and lysophosphatidic acid enhance survival dueing hypoxia in neonatal rat cardiac myocytes. J Mol Cell Cardiol. 2001; 33: 1713-1717.
57) Karliner J S. Mechanisms of cardioprotection by lysophospholipids. J Cell Biochem 2004; 92: 1095-1103.
58) Liang Q, Wiese R J, Bueno O F, Dai Y S, Markham B E, Molkentin J D. The transcription factor GATA4 is activated by extracellular signal-regulated kinase 1- and 2-mediated phosphorylation of serine 105 in cardiomyocytes. Mol Cell Biol. 2001; 21: 7460-7469.
59) Gao T, Furnari F, Newton A C. PHLPP: a phosphatase that directly dephosphorylates Akt, promotes apoptosis, and suppresses tumor growth. Mol. Cell. 2005; 18:13-24.
60) Wang Z, Bhattacharya N, Mixter P F, Wei W, Sedivy J, Magnuson N S. Phosphorylation of the cell cycle inhibitor p21Cip1/WAF1 by PIM-1 kinase. Biochim Biophys Acta. 2002; 1593: 45-55.
61) Gottlieb R A, Gruol D L, Zhu J Y, Engler R L. Preconditioning rabbit cardiomyocytes: role of pH, vacuolar proton ATPase, and apoptosis. J Clin Invest. 1996; 97:2391-2398.
62) Karwatowska-Prokopczuk E, Nordberg J A, Li H L, Engler R L, Gottlieb R A. Effect of vacuolar proton ATPase on pHi, Ca2+, and apoptosis in neonatal cardiomyocytes during metabolic inhibition/recovery. Circ Res. 1998; 82: 1139-44.
63) Plank D M, Sussman M A. Impaired intracellular Ca2+ dynamics in live cardiomyocytes revealed by rapid line scan confocal microscopy. Microsc Microanal. 2005; 11: 235-43.
64) Plank D M, Yatani A, Ritsu H, Witt S, Glascock B, Lalli M J, Periasamy M, Fiset C, Benkusky N, Valdivia H H, Sussman M A. Calcium dynamics in the failing heart: restoration by beta-adrenergic receptor blockade. Am J Physiol Heart Circ Physiol. 2003; 285: H305-15.
65) Zorov B Z, Filburn C R, Klotz L-O, Zwier J L and Sollott S J. Reactive oxygen species (ROS)-induced ROS release: a new phenomenon accompanying induction of the mitochondrial permeability transition in cardiac myocytes. J Exp Med. 2000; 192: 1001-1014.
66) Sayen M R, Gustafsson A B, Sussman M A, Molkentin J D and Gottlieb R A. Calcineurin transgenic mice have mitochondrial dysfunction and elevated superoxide production. Am J Physiol Cell Physiol 2003; □□□: C□□□□C□□.
67) Clarke S J, McStay G P and Halestrap A P. Sanglifehrin A acts as a potent inhibitor of the mitochondrial permeability transition and reperfusion injury of the heart by binding to cyclophilin-D at a different site from cyclosporin A. J Biol. Chem. 2002; 277: 34793-34799.
68) Yuan H, Williams S D, Adachi S, Oltersdorf T and Gottlieb R A. Cytochrome c dissociation and release from mitochondria by truncated Bid and ceramide. Mitochondrion 2003; 2: 237-244.
69) Gustafsson A B, Tsai J G, Logue S E, Crow M T and Gottlieb R A. Apoptosis repressor with caspase recruitment domain protects against cell death by interfering with Bax activation. J Biol. Chem. 2004; 279: 21233-21338.

EXAMPLE 3

Pim-1 Kinase Antagonizes Aspects of Myocardial Hypertrophy and Compensation to Pathological Pressure Overload The following data demonstrate that Pim-1 kinase exerts potent cardioprotective effects in the myocardium downstream of AKT, and that PIM-1 plays a role in cardiac hypertrophy. Cardiac-specific expression of Pim-1 (Pim-wt) or the dominant-negative mutant of Pim-1 (Pim-DN) in transgenic mice together with adenoviral-mediated overexpression of these Pim-1 constructs was used to delineate the role of Pim-1 in hypertrophy. Transgenic overexpression of Pim-1 protects mice from pressure overload induced hypertrophy relative to wild-type controls as evidenced by improved hemodynamic function, decreased apoptosis, increases in anti-hypertrophic proteins, smaller myocyte size, and inhibition of hypertrophic signaling after challenge. Similarly, Pim-1 overexpression in neonatal rat cardiomyocyte cultures inhibits hypertrophy induced by endothelin-1. On the cellular level, hearts of Pim-wt mice show enhanced incorporation of BrdU into myocytes as well as a hypercellular phenotype compared to wild-type controls after hypertrophic challenge. In comparison, transgenic overexpression of Pim-DN leads to dilated cardiomyopathy characterized by increased apoptosis, fibrosis, and severely depressed cardiac function. Furthermore, overexpression of Pim-DN leads to reduced contractility as evidenced by reduced $Ca^{2+}$ transient amplitude and decreased percent cell shortening in isolated myocytes. These data support a pivotal role for Pim-1 in modulation of hypertrophy by impacting responses on molecular, cellular, and organ levels.

Cardiac-Specific Pim-1 Transgenesis

The wildtype form of human Pim-1 (Pim-wt) and a kinase dead mutant that functions as a dominant negative protein (Pim-DN) (16) were fused to GFP under control of the cardiac specific α-myosin heavy chain promoter. PCR of mouse lines created with these constructs show incorporation of the transgenes into the genome. Immunoblot of whole heart lysates from transgenic samples revealed a 64-kDa GFP-Pim-1 fusion protein that is recognized by both Pim-1 and GFP antibodies. Bona fide inhibitory function of the Pim-DN construct was validated using the ability of Pim-1 to activate GATA-1 transcription (Magnuson, unpublished data). Pim-wt phosphorylates the transcription factor GATA-1 and induces GATA-1 luciferase reporter expression in C2C12 myoblasts, with increasing titration of Pim-DN inhibiting GATA-1 activity. Based on previous studies that showed Pim-1 phosphorylates p21 (29), in-vitro kinase assays confirmed activity of our Pim-wt construct using whole heart lysates that were prepared from GFP-Pim-1-wt, GFP-Pim-1-DN transgenic mice and non-transgenic (NTG) mice. GFP-Pim-1 proteins (wt or KD) were immunoprecipitated from whole heart lysates and incubated in the presence of [γ-32P] ATP with GST-p21 as substrates. Samples were resolved on SDS-PAGE, and $^{32}$P-labeled proteins were detected by autoradiography. Pim-wt overexpression phosphorylates p21 while this activity was abolished in the Pim-DN construct.

Pim-1 Inactivation Increases Cardiomyocyte Apoptosis and Fibrosis

Figure 12:
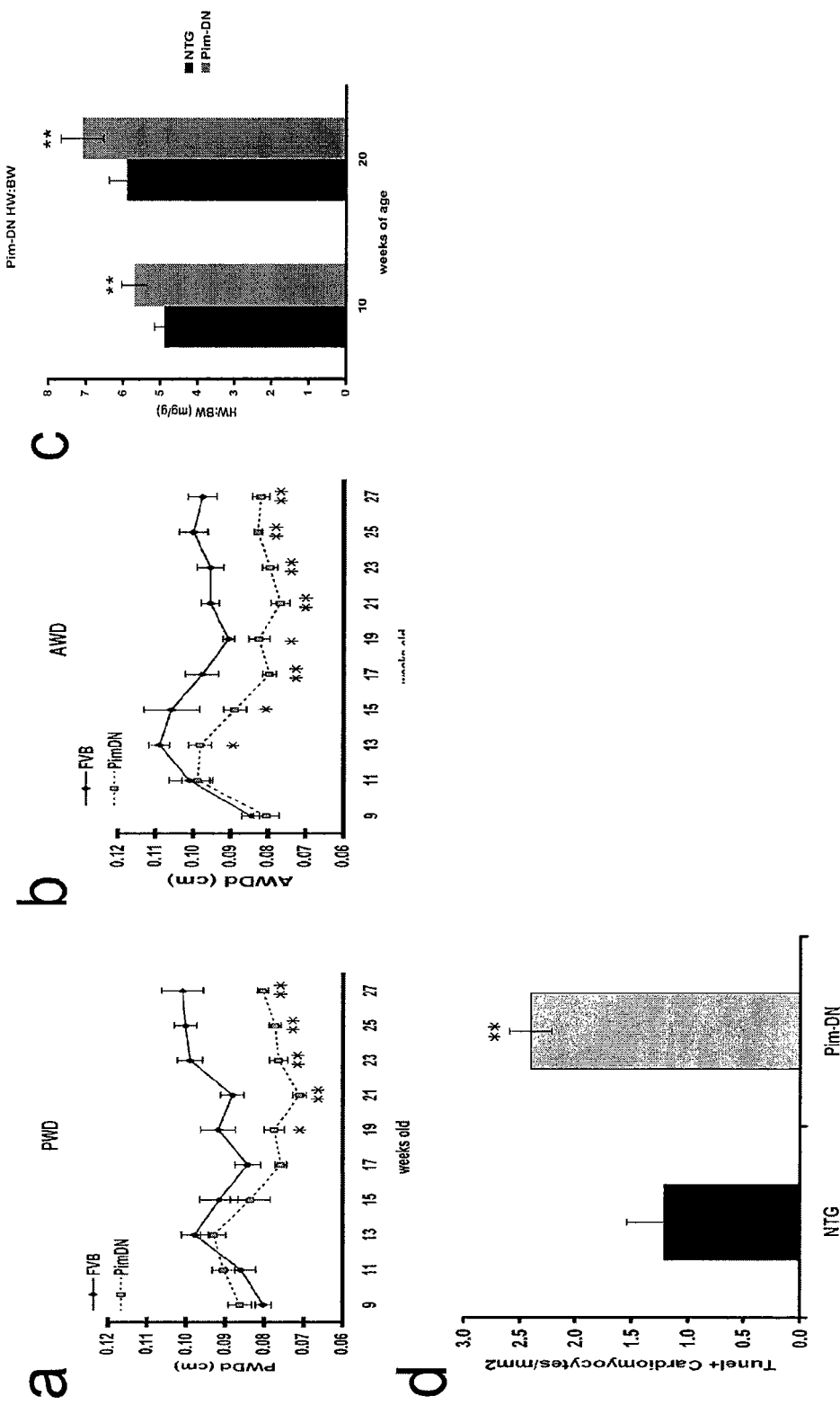
FIG. 12 graphically illustrates data showing that inactivation of Pim-1 in the myocardium increases apoptosis and fibrosis.

Hearts from mice created with genetic deletion of Pim-1 (Pim-1 KO) exhibit increased apoptosis in myocytes relative to NTG (non-transgenic) controls but show no evidence of overt cardiomyopathic remodeling (12). In comparison, Pim-DN overexpressing mice suffer from cardiomyopathy characterized by progressive wall thinning beginning at 3-4 months of age. FIG. 12 compares the characteristics of the wild-type NTG mice with the mice lacking active PIM-1. In FIG. 12a, echocardiographic measurement of posterior wall dimension over time shows the PIM-DN mice have a progressive thinning. This is also seen in the anterior wall dimension in FIG. 12b. As shown in FIG. 12c, the heart:body weight ratio at 10 and 22 weeks after birth is also significantly increased in the PIM-DN mice. Since Pim-DN overexpression induces cardiomyocyte apoptosis in vitro (12), assessment of apoptotic myocytes in the myocardium of Pim-DN animals was performed by TUNEL staining. Pim-DN animals exhibit a two-fold increase in apoptotic cardiomyocytes per $mm^2$ relative to age-matched controls ($1.2/mm^2$ and $2.4/mm^2$ respectively, FIG. 12d $p<0.01$) resulting in increased fibrosis and collagen deposits in the left ventricle. In addition, the amount of necrosis was quantified (p<0.01) and found to be significantly increased at basal levels in Pim-DN animals.

In summary, FIG. 12 graphically illustrates data showing that inactivation of Pim-1 in the myocardium increases apoptosis and fibrosis. FIG. 12a and FIG. 12b graphically illustrate echocardiographic measurement of posterior (12a) and anterior (12b) wall dimension (PWD and AWD respectively) in NTG (n=5) and Pim-DN (n=7) animals at two week intervals (*p<0.05, p<0.01). FIG. 12c graphically illustrates heart weight to body weight ratios in NTG and Pim-DN animals at 10 and 22 weeks of age (n=6, p<0.01). FIG. 12d graphically illustrates histogram data representing counts of TUNEL positive myocytes per mm$^2$ in 17-22 week old NTG and Pim-DN transgenics (n=3, **p<0.01).

Pim-DN Hearts Exhibit Depressed Cardiac Function

Hearts of Pim-DN mice show progressive dilation from 17 weeks of age (*p<0.05) with attendant depression of fractional shortening and ejection fraction (36.6% and 74.2% respectively) by 27 weeks of age (*p<0.05, **p<0.01) by echocardiographic analyses. Morphometric analysis performed on both NTG and Pim-DN hearts additionally confirmed that Pim-DN hearts were significantly dilated. In vivo hemodynamic assessments verified impaired hemodynamics with diminished ±dP/dt, increased left-ventricular end diastolic pressure (LVEDP), and decreased left-ventricular developed pressure (LVDP). Mechanistically, Pim-DN myocytes displayed reduced Ca$^{2+}$ transient amplitude coupled with decreased percent cell shortening in respect to NTG myocytes. Additionally, the time constant (ti) of the Ca$^{2+}$ transient decay was larger in Pim-DN myocytes. These results indicate that depressed contractile function of Pim-DN myocytes is mediated, at least in part, by a decline in Ca$^{2+}$ release from the sarcoplasmic reticulum together with a slower reuptake. Thus inactivation of Pim-1 by Pim-DN in the myocardium has a negative effect on cardiac function.

Overexpression of Pim-1 Inhibits Hypertrophy In Vitro

Induction of Pim-1 in the damaged myocardium is thought to be a protective survival response (12) occurring in cardiomyocytes such as those in the infarct border zone where Pim-1 colocalizes to cells expressing atrial natriuretic peptide. ANP is both anti-hypertrophic and cardioprotective (24), so the coincidence of these proteins prompted assessment of the role that Pim-1 accumulation plays in mitigation of hypertrophic signaling.

Figure 13:
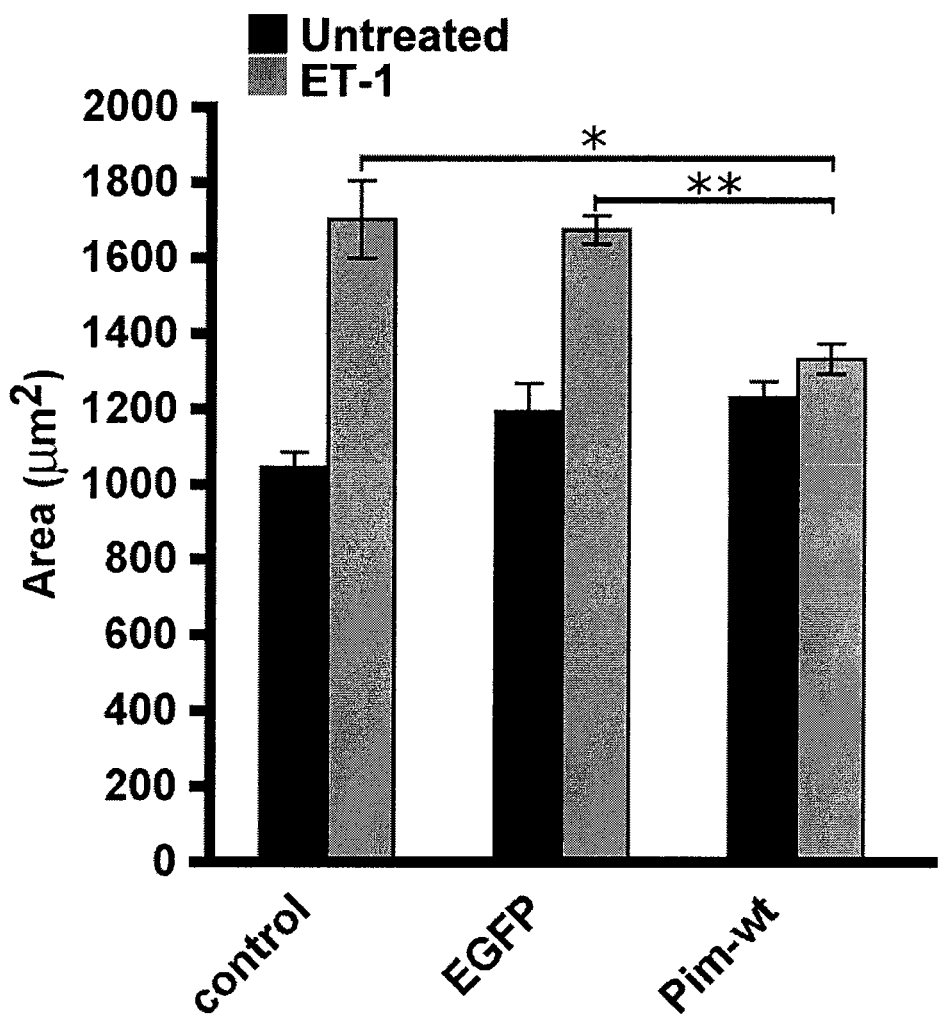
FIG. 13 shows individual cell surface area measurements from uninfected control, EGFP, and Pim-wt infected neonatal rat cardiomyocyte cultures treated and untreated with endothelin-1, as described in detail in Example 3, below.

The impact of Pim-wt overexpression upon cardiomyocyte hypertrophy was initially examined using neonatal rat cardiomyocytes (NRCMs) infected with adenoviruses encoding EGFP-Pim-wt or EGFP protein followed by stimulation with endothelin-1 (ET-1) for 24 hours. FIG. 13 shows individual cell surface area measurements from uninfected control, EGFP, and Pim-wt infected neonatal rat cardiomyocyte cultures treated and untreated with endothelin-1. As illustrated in FIG. 13, Pim-wt overexpression inhibits ET-1 induced hypertrophy (*p<0.05, **p<0.01) as assessed by cell surface area measurements relative to the increase in cell size seen in control and EGFP infected myocytes treated with ET-1. Molecular profiling of the hypertrophic signature of untreated cultures shows that Pim-wt expression decreases mRNA levels for atrial natriuretic peptide (ANP) by 60.6% and B-type natriuretic peptide (BNP) by 39.8% while increasing α-skeletal actin levels 89% compared to EGFP infected controls. However, upon treatment with ET-1, Pim-wt cultures exhibit a 2.5-fold increase in ANP levels and 10.2-fold decrease in β-myosin heavy chain levels versus ET-1 treated EGFP controls. Unfortunately, cultured cardiomyocytes overexpressing Pim-DN protein show diminished viability after the necessary time course to infect and treat with ET-1 as evidenced by high levels of TUNEL positive cells. As cardiomyocytes overexpressing Pim-DN protein begin to round up and detach from the plate, their morphology is drastically changed, thereby preventing an accurate assessment of cell size (12). However, the effect of Pim-DN on hypertrophy can be seen using the specific Pim-1 activity inhibitor quercetagetin. Pim-1 expressing NRCM cultures were treated for 1 hour with or without 10 nM quercetagetin prior to 48 hour incubation with ET-1 and cell size assessment. Cells treated with quercetagetin and ET-1 had significantly larger surface compared to ET-1 stimulated cells where Pim-1 activity was not blunted by inhibitor. Collectively these results support an anti-hypertrophic role when Pim-1 is overexpressed, albeit at levels well above normal physiological induction in this cell culture system.

In summary, FIG. 13 graphically illustrates data showing that Pim-1 overexpression protects cardiomyocytes from endothelin-1 induced hypertrophy. Individual cell surface area measurements from uninfected control, EGFP, and Pim-wt infected neonatal rat cardiomyocyte cultures treated and untreated with endothelin-1 (ET-1) (n=4, *p<0.05, **p<0.01).

Pim-1 Overexpression Inhibits Remodeling Induced by Pressure Overload Hypertrophy Consequences of Pim-1 overexpression upon hypertrophy in vivo was assessed with Pim-wt mice subjected to transaortic constriction (TAC) to induce pressure overload relative to age and gender matched NTG controls. With reference to FIGS. 14a-f, line graphs were generated representing weekly echocardiographic assessment of NTG and Pim-wt sham and TAC banded hearts for anterior wall dimension (AWD 14d, 14a), posterior wall dimension (PWD 14d, 14b), end diastolic dimension (EDD, c), end-systolic dimension (ESD, 14d), percent fractional shortening (FS, 14e), and ejection fraction (EF, 14f) (NTG sham n=6, Pim-wt sham n=6, NTG TAC n=9, Pim-wt TAC n=9; *p<0.05, **p<0.01) (FIG. 14a-14b, *p<0.05, **p<0.01).

Results show that TAC of control NTG hearts prompts remodeling at two weeks after challenge evidenced by anterior and posterior wall thickening. In comparison, Pim-wt animals do not show significant increases in wall thickness for up to 14 weeks after challenge (FIGS. 14a-14b). Similarly, NTG controls show left ventricular chamber enlargement measured by end diastolic diameter (EDD) within 8 weeks after banding, and end systolic diameter (ESD) increases significantly within 4 weeks. Neither EDD nor ESD parameters show significant changes in Pim-wt transgenics throughout the same time period (FIGS. 14c-14d, p<0.01 vs. sham, $p<0.01 vs. Pim-wt TAC). Furthermore, NTG controls show marked decreases in both fractional shortening (FS) and ejection fraction after challenge, while myocardial function is maintained in Pim-wt hearts (FIGS. 14e-14f; p<0.01 vs. Pim-wt TAC). Interestingly, although decreases in cardiac function are seen in NTG animals, Pim-1 protein is modestly elevated in response to pressure overload during early hypertrophy and progression to heart failure. Endogenous levels of Pim-1 expression increase early during adaptive hypertrophy and decline shortly thereafter, while during late -phase hypertrophy (9 weeks post-TAC), Pim-1 appears localized to nuclei within vasculature. These observations support the conclusion that Pim-1 is induced in response to stress.

Figure 14:
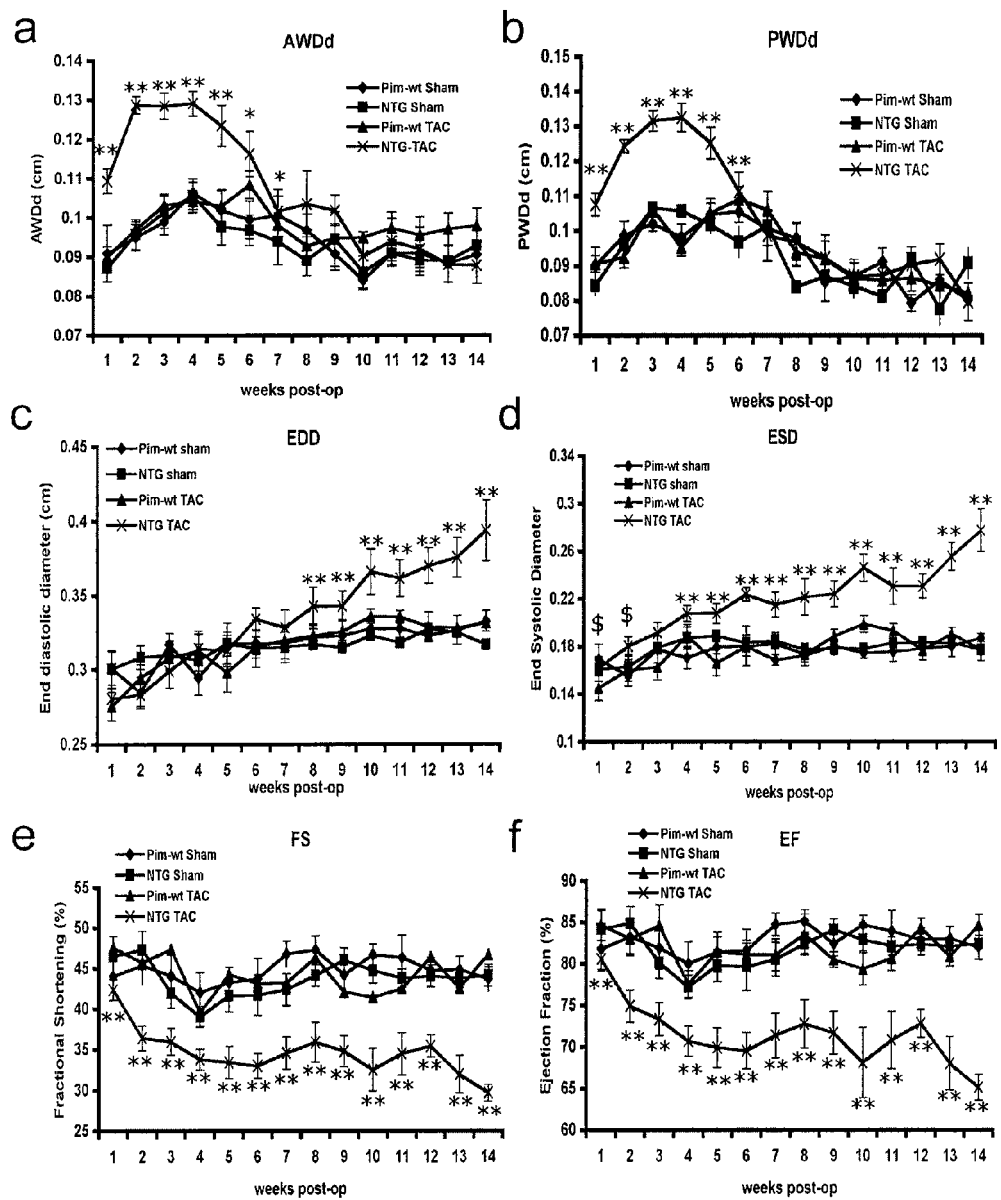
FIG. 14 graphically illustrates data showing Pim-wt transgenic animals are resistant to pressure overload induced hypertrophy.

In summary, FIG. 14 graphically illustrates data showing Pim-wt transgenic animals are resistant to pressure overload induced hypertrophy. FIG. 14a-f) Line graphs representing weekly echocardiographic assessment of NTG and Pim-wt sham and TAC banded hearts for anterior wall dimension (AWDd, a), posterior wall dimension (PWDd, b), end diastolic dimension (EDD, c), end-systolic dimension (ESD, d), percent fractional shortening (FS, e), and ejection fraction (EF, f) (NTG sham n=6, Pim-wt sham n=6, NTG TAC n=9, Pim-wt TAC n=9; *p<0.05, **p<0.01).

Pim-Wt Hearts are Resistant to TAC Induced Hypertrophy

NTG mice exhibit significant increases in heart size and succumb at a significantly faster rate compared to Pim-wt transgenic mice following TAC challenge. Molecular mRNA markers of hypertrophy including ANP, BNP, α-skeletal actin (αSKA), β-myosin heavy chain (β-MHC) and c-fos are significantly increased in NTG TAC challenged hearts compared to shams. In comparison, molecular hypertrophic markers are not significantly increased in hearts of Pim-wt mice subjected to TAC challenge, although Pim-wt hearts do express more c-fos mRNA under basal conditions. Quantitation of apoptotic myocytes by TUNEL labeling in sections reveals a 3.72-fold increase in NTG TAC-challenged hearts compared to shams ($3.2/mm^2$ and $0.86/mm^2$ respectively), whereas Pim-wt animals exhibit no significant increase in TUNEL positive cells ($1.31/mm^2$ versus $1.05/mm^2$). Consistent with improved myocardial viability, Pim-wt TAC-challenged hearts show decreased peri-vascular fibrosis as well as decreased necrosis relative to NTG TAC-challenged counterparts. Additionally, Pim-wt TAC banded hearts have significantly increased levels of anti-apoptotic proteins including Bcl-xl, Bcl-2, and increased phosphorylation of BAD relative to NTG counterparts. These data support the idea that protection afforded by Pim-1 overexpression is due in part to increased survival signaling.

Pim-Wt Hearts Exhibit Increased Contractile Function in Response to TAC Banding

Decreased fibrosis is present in Pim-wt hearts after TAC banding, suggesting Pim-1 overexpression preserves contractile function. Actions of Pim-1 overexpression upon cardiac contractility were examined using Pim-wt and NTG controls assessed by in vivo hemodynamic measurements conducted at 4 weeks and 10 weeks after TAC challenge. FIGS. 15a-c illustrate an in vivo hemodynamic assessment of NTG and Pim-wt hearts 4 and 10 weeks (black and gray bars respectively) after sham or TAC operation (14 and 20 weeks of age respectively). FIG. 15a shows ±dP/dt measurements; FIG. 15b shows left ventricular developed pressure (LVDP), and FIG. 15c illustrates left ventricular end-diastolic pressure (LVEDP). While contractile function is depressed in NTG TAC-challenged hearts at both time points, Pim-wt hearts possess better function after TAC challenge with slight decreases in +dP/dt and no significant change in –dP/dt compared to sham operated NTG controls. Comparison of 4-week and 10-week dP/dt assessments show significant decreases in function for both NTG and Pim-wt TAC challenged hearts, although performance of Pim-wt TAC-challenged hearts is relatively improved. Measurements reveal increases in left ventricular developed pressure and end-diastolic pressure in NTG hearts 4 and 10 weeks after TAC, but Pim-wt hearts show relative preservation of LVDP (FIG. 15b, Pim-wt 19.75% increase, p<0.01) and no change in LVEDP (FIG. 15c p<0.01, $$p<0.01 vs. NTG TAC). Hemodynamic function reflected in ±dP/dt and LVDP is improved in Pim-wt hearts compared to NTG at 4 and 10 week time points (FIGS. 15a-15b, ψp<0.05, ψψp<0.01).

Figure 15:
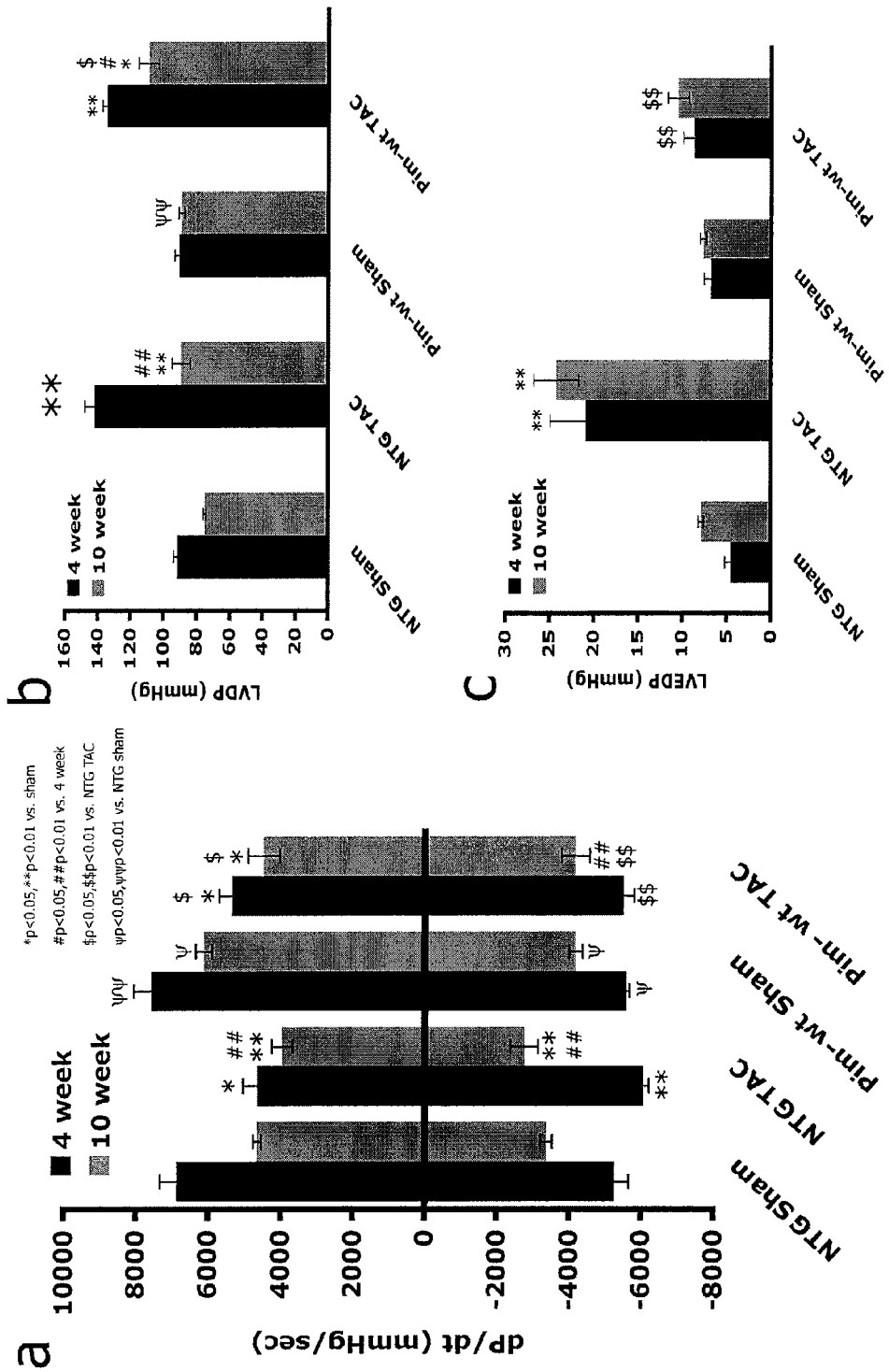
FIG. 15 graphically illustrates data showing that Pim-1 enhances cardiac function.

In summary, FIG. 15 graphically illustrates data showing that Pim-1 enhances cardiac function. FIG. 15a-c) In vivo hemodynamic assessment of NTG and Pim-wt hearts 4 and 10 weeks (black and gray bars respectively) after sham or TAC operation (14 and 20 weeks of age respectively). ±dP/dt measurements (FIG. 15a), left ventricular developed pressure (LVDP, b), left ventricular end-diastolic pressure (LVEDP, FIG. 15c). For 4-week animals NTG sham n=4, NTG TAC n=3, Pim-wt sham n=4, Pim-wt TAC n=4. For 10-week animals NTG sham n=5, NTG TAC n=10, Pim-wt sham n=14, Pim-wt TAC n=7 (*p<0.05, **p<0.01 vs. sham, ##p<0.01 vs. 4-week TAC, $p<0.05, $$p<0.01 vs. NTG TAC, ψp<0.05, ψψp<0.01 vs. NTG sham).

The mechanistic basis for preservation of contractile function in Pim-wt hearts may rest with the cellular response in TAC challenged animals. NTG and Pim-wt groups injected with BrdU for 10 days were used to assess stimulation of DNA synthesis and potential cellular proliferation after TAC challenge. Pim-wt hearts possess 67% more BrdU+ myocytes relative to NTG controls after TAC challenge. The majority of BrdU+ cells in Pim-wt hearts post-TAC are diploid, supporting the premise that increases in BrdU+ cells stemmed from new myocyte formation and not enhanced DNA synthesis in pre-existing cells. Consistent with improved contractility, we now show that in addition to increased SERCA2a levels (12), Pim-wt hearts also show increased levels of phosphorylated phospholamban (PLB) while Pim-DN animals show significant decreases in phospho-PLB compared to NTG control animals. These results support the conclusion that in the face of decreased cardiac function, overexpression of Pim-1 allows the heart to maintain function through increased contractility through elevation of SERCA2a and phosphorylated PLB.

Pim-1 Increases Myocardial Cellularity

The volume and cellularity of myocytes resulting from myocardial Pim-1 overexpression was assessed by quantitation of myocyte volume distribution. Results show Pim-wt hearts possess an increased percentage of small myocytes relative to NTG controls that is also reflected in decreased average myocyte size in these hearts, resulting in a hypercellular phenotype of approximately 33% more myocytes in Pim-wt compared to NTG. Additionally, isolated Pim-DN myocytes were 11% larger than NTG myocytes, indicating an inverse effect wherein impaired Pim-1 activity prompts formation of larger myocytes in the transgenic heart.

Inhibition of hypertrophy in vivo and in vitro indicates Pim-1 contributes to Akt-mediated blunting of hypertrophic remodeling. Pim-1 is only upregulated in localized regions close to acute injury or damage and is not increased throughout the myocardium until initiation of transit to end stage failure. Thus, Pim-1 likely serves as a survival and protective response to blunt maladaptive hypertrophic remodeling in early phases of reactive signaling. In comparison, Pim-1 elevation occurring in late stage decompensation probably represents a terminal effort to preserve function, although beneficial effects can be overridden by the sequelae of end stage failure. The differential expression of endogenous Pim-1 during transition from adaptive to maladaptive hypertrophy possibly represents a mechanism by which Pim-1 exerts cardioprotection.

Nuclear AKT delayed but did not overcome compensatory remodeling after TAC challenge (9), but Pim-wt transgenic hearts exhibit persistent blunting of myocardial hypertrophy (see e.g., FIG. 14) without increases in apoptosis, changes in hypertrophic signaling markers or deterioration of function (see e.g., FIG. 15). In addition, Pim-wt transgenic hearts perform significantly better functionally than NTG counterparts at 14 and 20 weeks of age (see e.g., FIG. 15). A potential basis for this remarkable resiliency to pressure overload is in part related to Pim-1-mediated induction of sarco/endoplasmic reticulum $Ca^{+2}$ATP-ase 2a (SERCA2a) (12) and phospholamban (PLB) expression. Overexpression of Pim-DN in the myocardium increases myocyte apoptosis (see e.g., FIG. 12d) associated with dilated cardiomyopathy, whereas genetic deletion of Pim-1 also results in increased apoptosis although dilated cardiomyopathy is not observed (12). The cardiomyopathic consequences of Pim-DN overexpression suggest this kinase is critical to cardiomyocyte viability, as compensatory up-regulation of Pim-2 occurs in the Pim-1 knockout line could help account for lack of cardiomyopathic changes (12). These findings are also consistent with our previous study that shows the dominant negative form of Pim-1 induces PARP and caspase 3 cleavage, increasing cardiomyocyte apoptosis in vitro (12). Furthermore for the effect on hypertrophy, Pim-DN seem to be able to mount a hypertrophic response as evidenced by increased anterior wall thickness at one week after TAC challenge (not shown).

Overexpression of Pim-1 in the pathologically challenged myocardium results in numerous salutary effects including decreased apoptosis, increased expression of anti-apoptotic proteins, and decreased fibrosis and necrosis. Pim-1 also increases the percentage of small myocytes and an overall increase in the number of myocytes constituting the myocardium. Consequently, PIM-1 overexpression provides an increased capacity to withstand TAC challenge by virtue of increased cell numbers of small cells and decreased cell death.

Genetic Ablation of Pim-1 increases infarction injury. Protective effects of Pim-1 were assessed following MI in Pim-KO animals. Left ventricular free wall infarct size is increased 22.7% in Pim-KO hearts compared to wild type controls. (FIG. 5a). Pim-KO mice possess a minor but significant increase in TUNEL positive myocytes in the left ventricle relative to wild type controls (Table S2, $p<0.01$), and this differential is exacerbated following MI up to a 4.0 fold increase in TUNEL positive myocytes relative to wild-type samples (FIG. 5b $p<0.01$). Hemodynamic performance is comparable between Pim-KO and wild type controls under normal conditions (FIG. S5), but developed ventricular pressure in Pim-KO mice is depressed and end diastolic pressure is increased with respect to wild type following infarction (FIG. 5c). Further, diastolic wall stress is significantly increased in both left ventricular free wall and septum after infarction in Pim-KO hearts (FIG. S5, $p<0.01$). Pim-KO mice were noted to possess decreased lymphocyte proliferation and hematopoetic cell differentiation[13-15] that could possibly decrease inflammatory responses following MI, but no significant differences were found in circulating c-kit+ cell number after MI or c-kit+/sca-1+ bone marrow cell number pre or post-MI (FIG. S5). Likewise, inflammatory cell recruitment following MI as indicated by CD45 staining is comparable between Pim-KO hearts versus controls (FIG. S5).

Pim-KO Hearts Exhibit Altered Protective Signaling.

Pim-1 may be a relatively promiscuous kinase based upon minimal target substrate recognition sequence requirements[16] and capacity for autophosphorylation[17], so molecular mechanisms responsible for Pim-1-mediated cardioprotection were examined.

Pim-1-KO heart samples possess increases in phospho-$AKT^{T308}$ (90.72%), phospho-$AKT^{S473}$ (2.76-fold), total AKT (2.10-fold), phospho-$STAT3^{Y705}$ (2.61-fold), total STAT3 (68.6%) and Pim-2 (4.6-fold) relative to wild type samples. However, no increases were observed for bcl-2, bcl-XL, phospho-$BAD^{S112}$, or Pim-3 expression compared to wild type controls (FIG. 16d). These survival-signaling molecules were also examined seven days after MI, when Pim-KO mice exhibit a 2.57-fold increase in Pim-3 expression, but decreases in bcl-$X_L$ (2.1-fold), phospho-$BAD^{S112}$ (75.9%), phospho-$AKT^{T308}$ (92.55%), phospho-$AKT^{S473}$ (2.24-fold), total AKT (73.66%), phospho-$STAT3^{Y705}$ (2.72-fold), total STAT3 (2.0-fold), with no significant changes in bcl-2 or Pim-2 expression compared to sham-operated controls (FIG. 5e). In comparison, wild type heart samples show significant increases in bcl-XL (57.0%), phospho-$BAD^{S1012}$ (64.58%), phospho-$AKT^{T308}$ (98.32%), phospho-$AKT^{S473}$ (2.81-fold), total AKT (2.26-fold), phospho-$STAT3^{Y765}$ (3.43-fold) total STAT3 (2.02-fold), with no change in Pim-2 or Pim-3 expression compared to sham (FIG. 16e). Thus, Pim-KO hearts exhibit significant increases in Pim-2 and Pim-3 compared to NTG hearts post-MI, but profound decreases in the other survival signaling molecules are observed (FIG. 16e).

Figure 16:
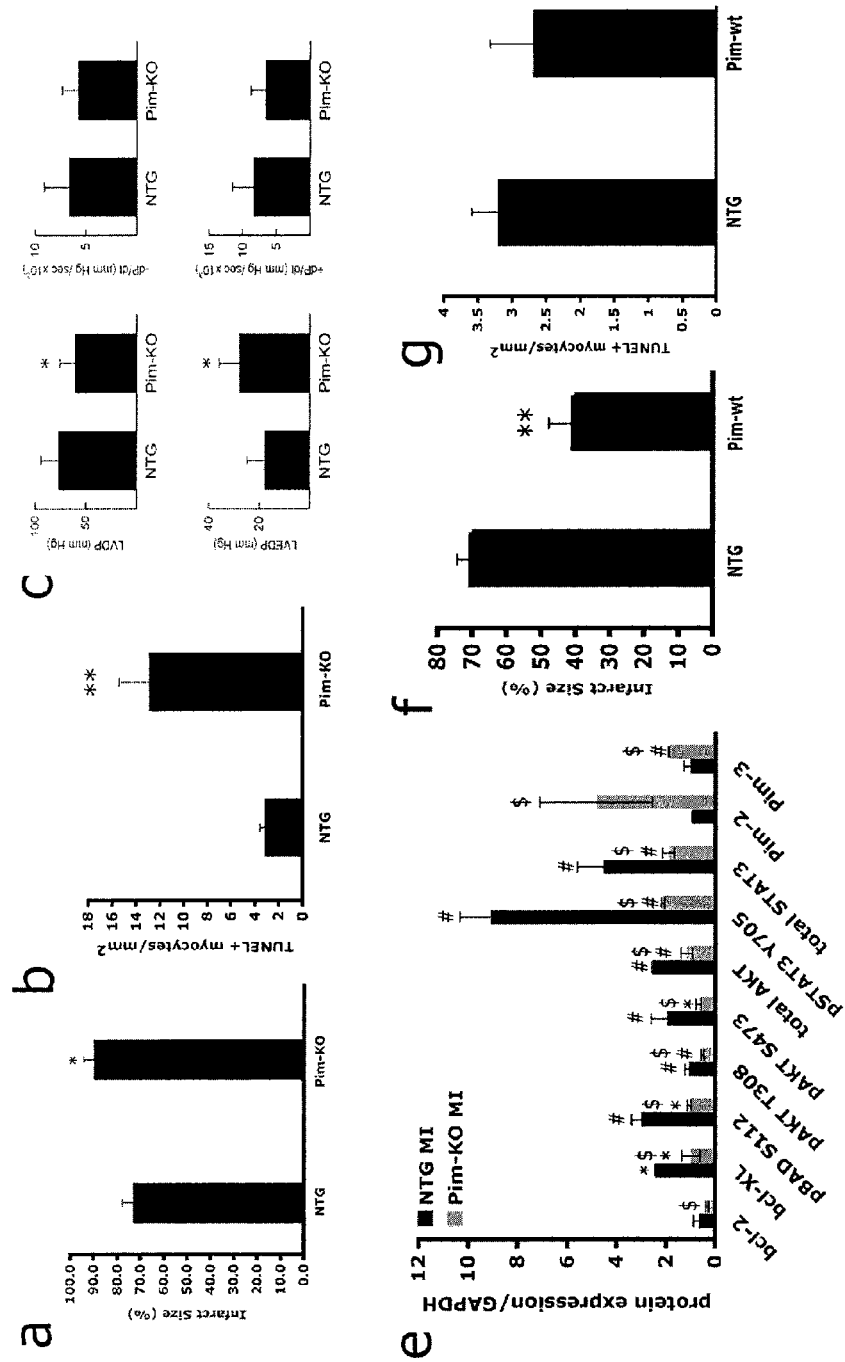
FIG. 16 graphically illustrates data demonstrating that Pim-1 protects against infarction injury.

In summary, FIG. 16 graphically illustrates data demonstrating that Pim-1 protects against infarction injury. FIG. 16a graphically illustrates a histogram representing infarct size 7 days post-MI as a percent of left-ventricular free wall in Pim-KO hearts (*$p<0.05$ v NTG MI). FIG. 16b graphically illustrates data showing the number of TUNEL positive myocytes per mm$^2$ 7 days post-MI in Pim-KO hearts (**$p<0.01$). FIG. 16c graphically illustrates in vivo hemodynamic measurements of NTG and Pim-KO mice 5 days following MI (*$p<0.05$). Left ventricular developed pressure (LVDP), left ventricular end-diastolic pressure (LVEDP), and ±change in pressure over change in time. FIG. 16e graphically illustrates Immunoblot quantitation of survival protein levels 7 days post-infarction in Pim-KO and NTG control hearts (*$p<0.05$ vs. sham, #$p<0.01$ vs. sham, $$p<0.01$ vs. NTG MI). FIG. 16f graphically illustrates Infarct size measurements 10 days post-infarction (n=3, **$p<0.01$). FIG. 16g graphically illustrates the number of TUNEL-labeled CM/m2 in LV 10 days after MI.

Materials and Methods

Generation of Transgenic Animals and Animal Use

Pim-wt and Pim-DN cDNA fragments (16) were subcloned into the α-MHC plasmid for transgenesis. Prior publications describe methods for TAC banding and echo (9), as well as HW:BW ratio determination and hemodynamics (12). Further details provided in the online supplement. All animal studies were approved by the Institutional Animal Use and Care Committee.

Confocal Microscopy, Immunoblotting and Assays

GFP-Pim-1 proteins immunoprecipitated from heart lysates were used in an in vitro kinase assay with GST-p21 as substrate. For luciferase assays, C2C12 cells transfected with indicated plasmids and pGATA-Luc reporter construct were analyzed for GATA-dependent luciferase activity. Methods for immunofluorescence microscopy were done as described in reference 26, listed below, immunoblotting were done as described in reference 24, listed below, quantitative RT-PCR and TUNEL ("terminal deoxynucleotidyl transferase-mediated dUTP-biotin nick end labeling") staining were done as described in reference 9, listed below.

In Vitro Cell Culture and Analyses

Neonatal rat cardiomyocyte cultures were prepared as described previously (10). Adult myocyte isolation, volume calculations, cell shortening and Ca$^{2+}$ transient experiments performed as previously described in references 12, 22, 25, listed below.

Figure Legends

REFERENCES FOR EXAMPLE 3

1. Neri, L. M., Borgatti, P., Capitani, S. & Martelli, A. M. (2002) The nuclear phosphoinositide 3-kinase/AKT pathway: a new second messenger system. *Biochim Biophys Acta* 1584, 73-80.

2. Sugden, P. H. (2003) Ras, Akt, and mechanotransduction in the cardiac myocyte. *Circ Res* 93, 1179-92.
3. McGowan, B. S., Ciccimaro, E. F., Chan, T. O. & Feldman, A. M. (2003) The balance between pro-apoptotic and anti-apoptotic pathways in the failing myocardium. *Cardiovasc Toxicol* 3, 191-206.
4. Kumar, D., Lou, H. & Singal, P. K. (2002) Oxidative stress and apoptosis in heart dysfunction. *Herz* 27, 662-8.
5. Hardt, S. E. & Sadoshima, J. (2002) Glycogen synthase kinase-3beta: a novel regulator of cardiac hypertrophy and development. *Circ Res* 90, 1055-63.
6. Sussman, M. A. & Anversa, P. (2004) Myocardial aging and senescence: where have the stem cells gone? *Annu Rev Physiol* 66, 29-48.
7. Latronico, M. V., Costinean, S., Lavitrano, M. L., Peschle, C. & Condorelli, G. (2004) Regulation of cell size and contractile function by AKT in cardiomyocytes. *Ann N Y Acad Sci* 1015, 250-60.
8. Condorelli, G., et al. (2002) Akt induces enhanced myocardial contractility and cell size in vivo in transgenic mice. *Proc Natl Acad Sci USA* 99, 12333-8.
9. Tsujita, Y., et al. (2006) Nuclear targeting of Akt antagonizes aspects of cardiomyocyte hypertrophy. *Proc Natl Acad Sci USA* 103, 11946-51.
10. Shiraishi, I., et al. Nuclear targeting of Akt enhances kinase activity and survival of cardiomyocytes. (2004) *Circ Res* 94, 884-91.
11. Gude, N., et al. (2006) Akt promotes increased cardiomyocyte cycling and expansion of the cardiac progenitor cell population. *Circ Res* 99, 381-8.
12. Muraski J., et al. (2007) Pim-1 regulates cardiomyocyte survival downstream of Akt. *Nature Medicine* 13, 12, 1467-75.
13. Hammerman, P. S., Fox, C. J., Birnbaum, M. J. & Thompson, C. B. (2005) Pim and Akt oncogenes are independent regulators of hematopoietic cell growth and survival. *Blood* 105, 4477-83.
14. Fox, C. J., et al. (2003) The serine/threonine kinase Pim-2 is a transcriptionally regulated apoptotic inhibitor *Genes Dev* 17, 1841-54.
15. Wang, Z., et al. (2001) Pim-1: a serine/threonine kinase with a role in cell survival, proliferation, differentiation and tumorigenesis. *J Vet Sci* 2, 167-79.
16. Bhattacharya, N., et al. (2002) Pim-1 associates with protein complexes necessary for mitosis *Chromosoma* 111, 80-95.
17. Takizawa, T., et al. (1999) Transcription of the SERCA2 gene is decreased in pressure-overloaded hearts: A study using in vivo direct gene transfer into living myocardium. *J Mol Cell Cardiol* 31, 2167-74.
18. Prasad, A. M., et al. (2007) Phenylephrine hypertrophy, Ca2+-ATPase (SERCA2), and Ca2+ signaling in neonatal rat cardiac myocytes. *Am J Physiol Cell Physiol* 292, C2269-75.
19. Asahi, M., et al. (2004) Cardiac-specific overexpression of sarcolipin inhibits sarco(endo)plasmic reticulum $Ca^{2+}$ ATPase (SERCA2a) activity and impairs cardiac function in mice. *Proc Natl Acad Sci USA* 101, 9199-204.
20. Suarez, J., et al. (2004) oxycycline inducible expression of SERCA2a improves calcium handling and reverts cardiac dysfunction in pressure overload-induced cardiac hypertrophy. *Am J Physiol Heart Circ Physiol* 287, H2164-72.
21. Kim, Y. K., et al. (2003) Mechanism of Enhanced Cardiac Function in Mice with Hypertrophy Induced by Overexpressed Akt. *J Biol Chem* 278, 47622-8.
22. Rota, M., et al. (2005) Nuclear targeting of Akt enhances ventricular function and myocyte contractility. *Circ Res* 97, 1332-41.
23. Seimi, S. K., et al. (2004) Glycogen synthase kinase-3beta is involved in the process of myocardial hypertrophy stimulated by insulin-like growth factor-1. *Circ J* 68, 247-53.
24. Kato, T., et al. (2005) ANP Promotes Cardiomyocyte Survival by cGMP-dependent Nuclear Accumulation of Zyxin and Akt. *J Clin Invest* 115, 2716-2730.
25. Kajstura, J., et al. (1995) The cellular basis of pacing-induced dilated cardiomyopathy. Myocyte cell loss and myocyte cellular reactive hypertrophy. *Circulation* 92, 2306-17.
26. Fransioli, J., et al. (2008) Evolution of The c-kit Positive Cell Response to Pathological Challenge in the Myocardium. *Stem Cells* 10.1634, 2007-0751.
27. Hoshijima, M., et al. (2002) Chronic suppression of heart-failure progression by a pseudophosphorylated mutant of phospholamban via in vivo cardiac rAAV gene delivery *Nature Medicine* 8, 864-871.
28. Zhang Y., Wang, Z., Li, X., Magnuson N., (2008) Pim kinase-dependent inhibition of c-Myc degradation. *Oncogene*, 1-11.
29. Zhang Y., Wang, Z., Magnuson N., (2007) Pim-1 kinase-dependent phosphorylation of p21Cip1/WAF1 regulates its stability and cellular localization in H1299 cells. *Mol. Cancer Research* 5, 909-922.

EXAMPLE 4

Pim-1 Engineered Cardiac Stem (Progenitor) Cells

Pim-1 Increases the Proliferation of Cardiac Progenitor Cells

To evaluate the growth rate of CGW-Pim-wt CPCs (cardiac progenitor cells), the number of viable cells was determined by trypan blue exclusion over a six day time course (FIG. 17A). At day six CGW-Pim-wt CPCs continued to expand significantly over that of CGW ($p<0.05$) and non-treated ($p<0.001$) CPCs. CGW-Pim-wt CPCs also exhibited an increased metabolic rate over CGW CPCs at one ($p<0.001$) and three days ($p<0.001$), as determined by MTT assay (FIG. 17B). A specific Pim-1 activity inhibitor, Quercetagentin, was used to confirm that the growth advantage acquired by CGW-Pim-wt CPCs was due to overexpression of Pim-1. When added to the culture media, the Pim-1 inhibitor significantly decreased the growth rate of CGW-Pim-wt CPCs at day two and three ($p<0.001$) compared to untreated CGW-Pim-wt CPCs (FIG. 17C).

Figure 17:
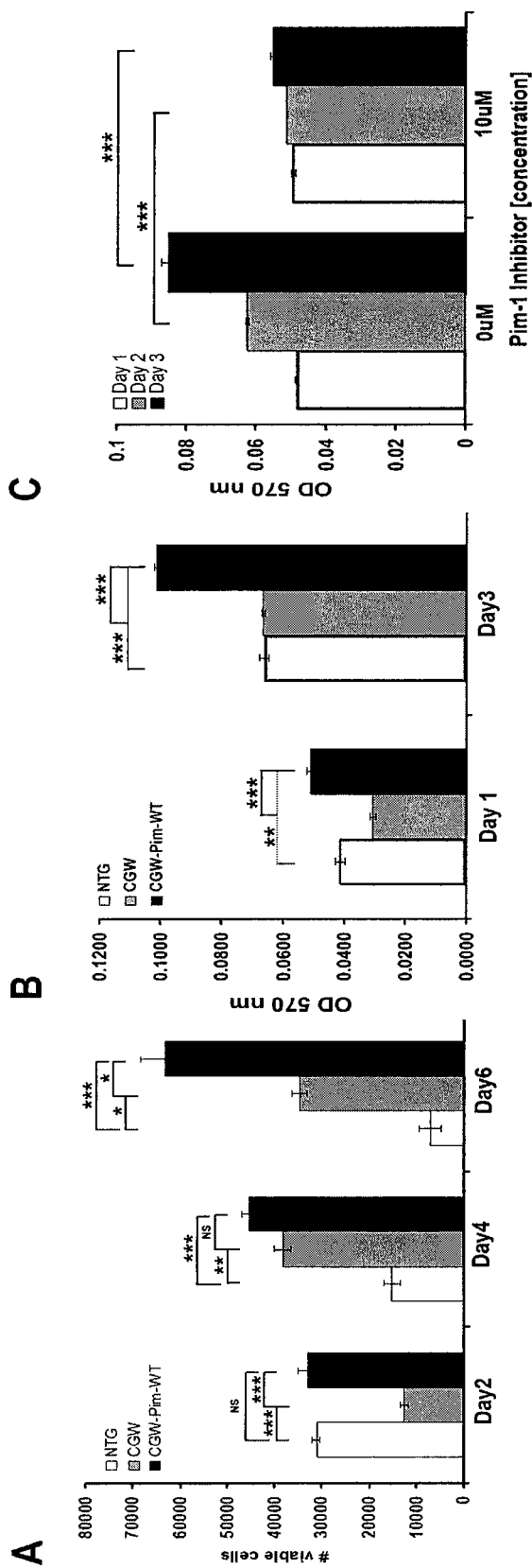
FIG. 17 illustrates data showing increased proliferative rate of Pim-1 engineered CSCs.

In summary, FIG. 17 illustrates data showing increased proliferative rate of Pim-1 engineered CSCs: FIG. 17A illustrates a cell growth assessment using trypan blue assay of control, CGW, and CGW-Pim-wt transduced CPCs; FIG. 17B illustrates an MTT assay on control, CGW, CGW-Pim-wt transduced CPCs (mean±SEM, n=3); FIG. 17C illustrates the proliferation rate of Pim-1 expressing CPC's treated with or without 10 uM of Quercetagentin, a specific Pim-1 activity inhibitor (mean±SEM, n=3)*$p<0.05$, $p<0.01$, *$p<0.001$.

Pim-1 Overexpressing CPCs Improve Cardiac Function Post-Myocardial Infarction

Previous studies have shown that Pim-1 transgenic mice elicit a significant resiliency to pathological challenge. To test whether Pim-1 modified CPCs would also confer substantial resistance to infarction damage, twelve week old female FVB mice were given a myocardial infarction and intramyocardially injected with CGW or CGW-Pim-wt CPCs surrounding the border zone (n=15-20/group). Echocardiography measurement at two weeks showed mice that received CGW-Pim-wt CPCs had a thicker anterior wall dimension (AWD) compared to that of saline (p<0.001) and CGW CPC (p<0.01) injected mice (FIG. 18A). In order to determine if intramyocardial injection of Pim-1 modified CPCs provides long term increased functional improvement after pathological challenge; mice were followed for 12 weeks post infarction. At 6 weeks post infarction mice that received CGW-Pim-wt CPCs maintained EF and FS (FIGS. 18B, C), and were statistically improved over CGW CPC injected mice. By 7 weeks, CGW CPCs failed to maintain cardiac function (FS and EF) and were not statistically different than those animals that received saline injections. At 12 weeks, echocardiography again indicated that CGW-Pim-wt CPC injected animals continued to maintain EF and FS, whereby animals that received control CPCs had a 2-fold and 1.6-fold decrease, respectively (FIGS. 18B, C). Hemodynamic measurements of DP (FIG. 18D), Ped (FIG. 18E), and changes in ±dp/dt (FIG. 18F), confirmed significant enhanced cardiac function in CGW-Pim-wt CPC injected mice over CGW CPC and saline injected animals.

Figure 18:
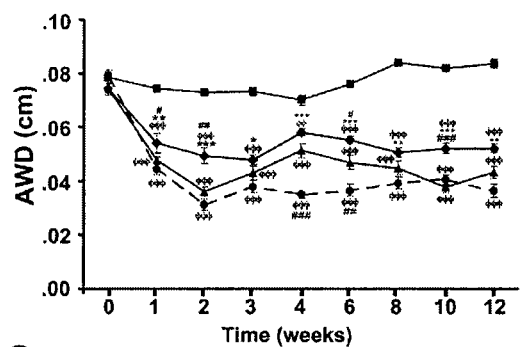
FIG. 18 graphically illustrates data showing that intra-myocardial injection of Pim-1 expressing CPCs improves cardiac function.
Figure 18:
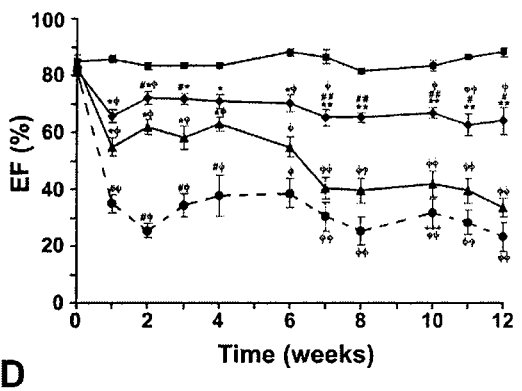
Figure 18:
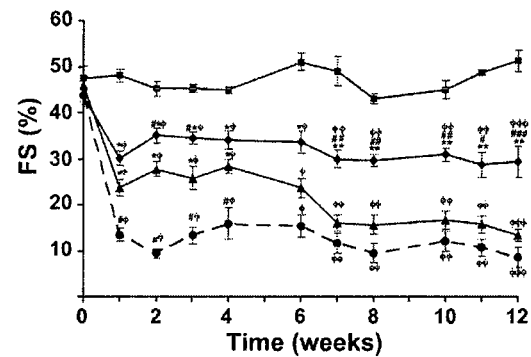
Figure 18:
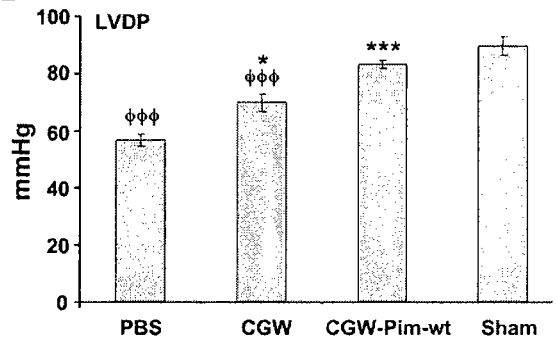
Figure 18:
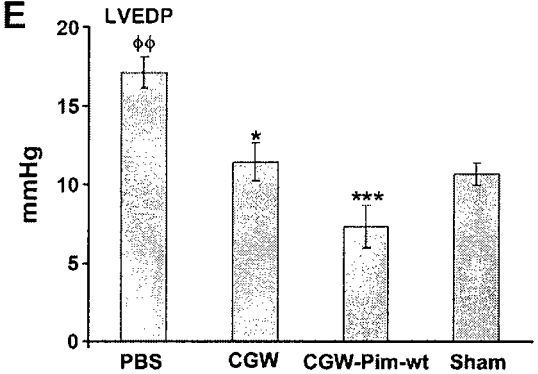
Figure 18:
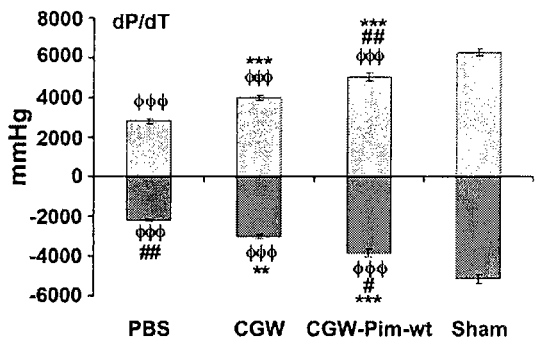

In summary, FIG. 18 graphically illustrates data showing that intra-myocardial injection of Pim-1 expressing CPCs improves cardiac function. FIG. 18A-C graphically illustrates electrocardiographic assessment of AWD (FIG. 18A), EF (FIG. 18B), and FS (FIG. 18C), in sham (■), PBS injected (●), CGW (▲), and CGW-Pim-WT (◆) cardiac progenitor cells 12 weeks post CPC transplantation. Echocardiography measurements represent n≥9 animals for each group. FIG. 18D-F graphically illustrates in vivo hemodynamic measurements of left ventricular developed pressure (LVDP) (18D), left ventricular end diastolic pressure (LVEDP) (18E), and dP/dT maximum and minimum (18F) were used to assess cardiac function 12 weeks post-intramyocardial injection of PBS, eGFP, and Pim-1 expressing CPCs (n≥5). ANOVA statistical tests were run for echocardiography and in-vivo hemodynamic measurements, using Tukey's post-hoc test. Results are represented as mean±SEM.

Injection of Pim-1 Modified CPCs Results in a Reduction of Infarct Size

Figure 19:
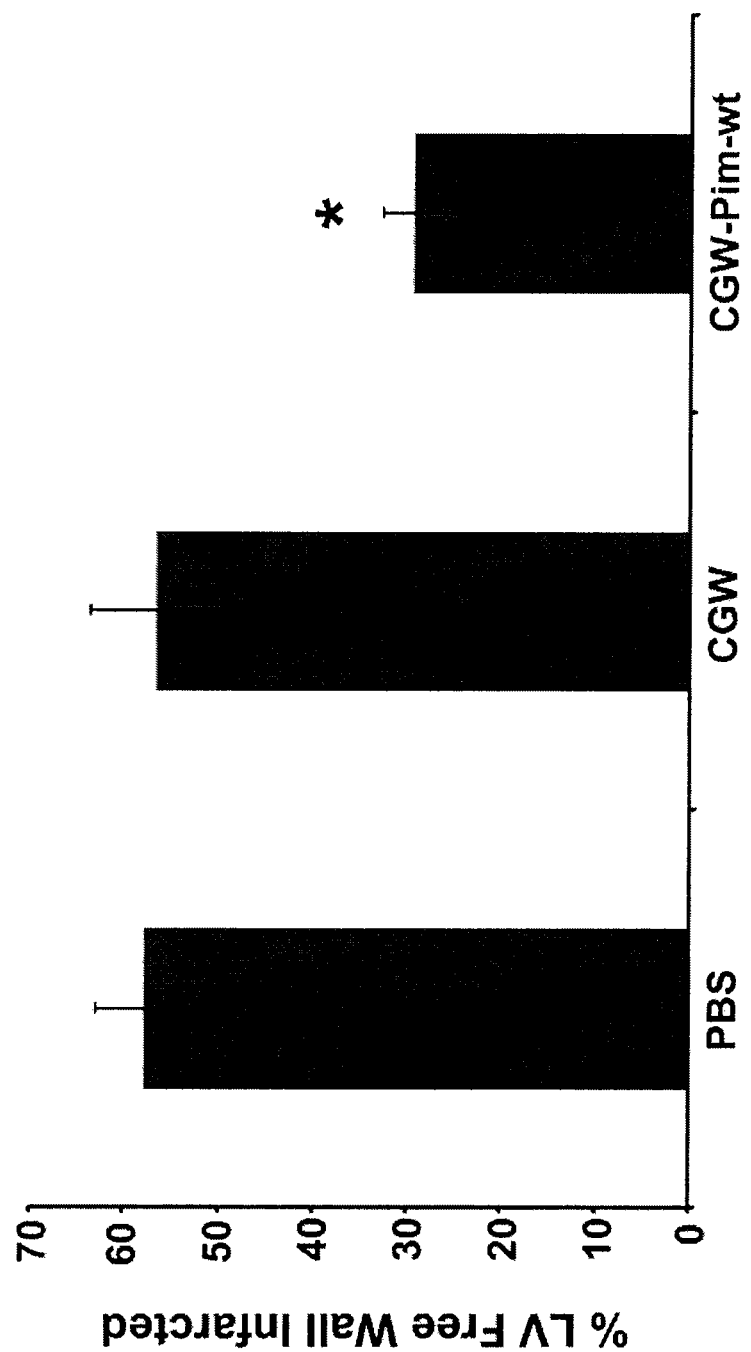
FIG. 19 graphically illustrates data showing that CGW-Pim-wt CPCs form myocytes and vasculature in infarcted heart tissue reducing infarction area; and shows a quantitation of infarction area 12 weeks post CPC injection, as described in detail in Example 4, below.

Quantitation of tropomyosin over left ventricular free wall area (LVFW) showed mice injected with Pim-1 modified CPCs had a significant 2-fold decrease in infarct area (p=0.02) (FIG. 3B). FIG. 19 graphically illustrates data showing that CGW-Pim-wt CPCs form myocytes and vasculature in infarcted heart tissue reducing infarction area; and shows a quantitation of infarction area 12 weeks post CPC injection. Results are represented as mean±SEM, n=3 animals, *p<0.02.

Long Term Cardiac Functional Improvement is Only Afforded by Pim-1 Modified CPCs In an effort to extend our previous studies we repeated our initial experiments and monitored injection of PBS, CGW, and CGW-Pim-wt CPC injected mice over 32 weeks by echocardiography and hemodynamic assessment. At 3 days all groups of mice had decreased FS (FIG. 20A) and EF (FIG. 20B), and were not statistically different from saline controls. As was previously seen, mice that received CGW CPCs had an initial early improvement at one week with onset of cardiac failure at six weeks, becoming statistically insignificant to saline controls by eight weeks. However, mice that received Pim-1 modified CPCs had an increase in FS and EF at 1 week that was maintained through 32 weeks (FIGS. 20A, B).

Figure 20:
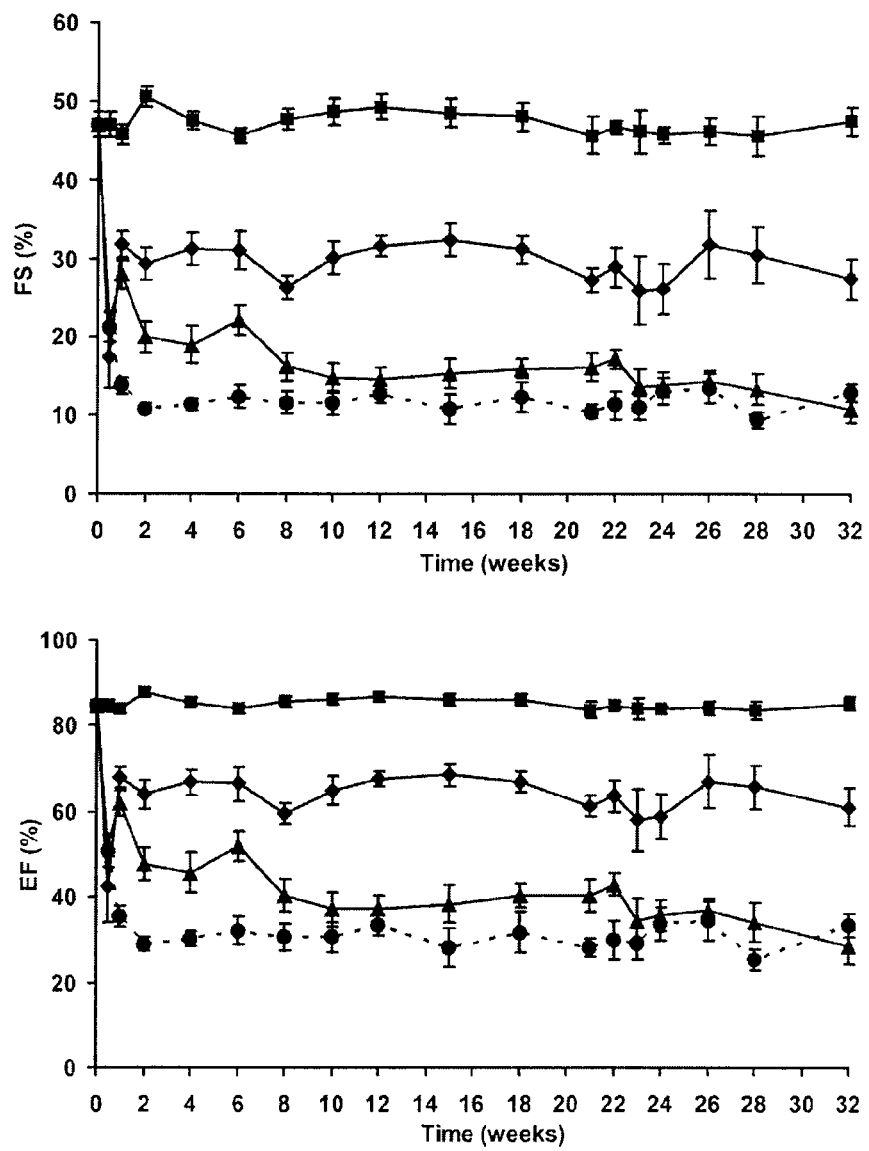
FIG. 20 graphically illustrates that long term cardiac functional recovery is afforded by CGW-Pim-wt expressing CPCs 32 weeks after intra-myocardial injection.

In summary, FIG. 20 graphically illustrates that long term cardiac functional recovery is afforded by CGW-Pim-wt expressing CPCs 32 weeks after intra-myocardial injection: FIG. 20A-C illustrates electrocardiographic assessment of FS (FIG. 20A), EF (FIG. 20B), and AWD (FIG. 20C), in sham (■), PBS injected (●), CGW (▲), and CGW-Pim-WT (◆) cardiac progenitor cells 32 weeks post CPC transplantation. Echocardiography measurements represent an n≥7 animals for each group.

Exemplary Bicistronic Vectors of the Invention

Vectors are bicistronic whereby the MND promoter drives Pim-1 expression and the reporter, enhanced green florescent protein (eGFP), is driven off a viral internal ribosomal entry site (vIRES). All constructs are third generation self-inactivating (SIN) lentiviral vectors and incorporate several elements to ensure long-term expression of the transgene. The MND (MND, myeloproliferative sarcoma virus LTR-negative control region deleted) promoter allows for high expression of the transgene, while the LTR allows for long-term expression after repeated passage. The vectors also include (IFN)-□-scaffold attachment region (SAR) element. The SAR element has been shown to be important in keeping the vector transcriptionally active by inhibiting methylation and protecting the transgene from being silenced.

In order to investigate the potential myocardial benefits of long term overexpression of Pim-1 in CPCs, a bicistronic lentiviral vector was designed to deliver the human Pim-1 gene, CGW-Pim-wt, as well as a control vector, CGW (FIG. S1A). Expression of the Pim-1 gene is controlled through a myeloproliferative sarcoma virus LTR-negative control region deleted (MND) promoter, while the eGFP reporter is driven off of a viral internal ribosomal entry site (vIRES).

Figure 21:
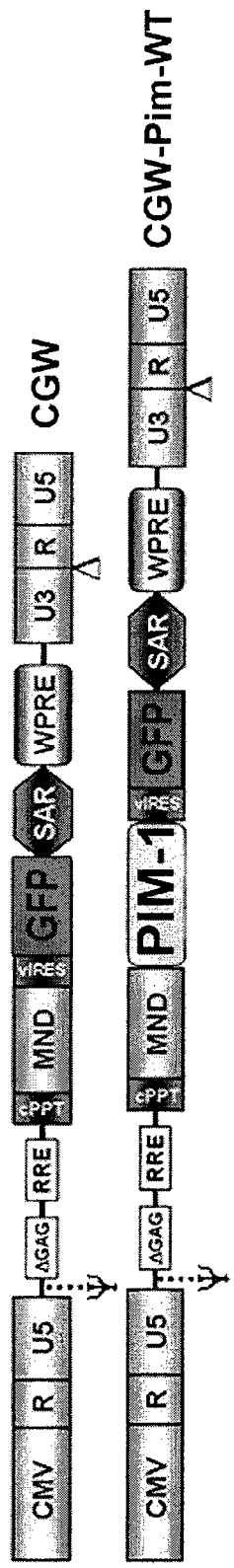
FIG. 21 illustrates an exemplary lentiviral constructs of the invention, as described in detail in Example 4, below.

FIG. 21 illustrates an exemplary lentiviral constructs of the invention for e.g., gene expression in cardiac progenitor cells, e.g., gene expression in c-kit+cardiac progenitor cells (CPCs). The figures illustrates a self-inactivating (SIN) lentiviral vectors, termed CGW (GFP control) and CGW-Pim-wt; they were designed such that the Pim-1 gene is driven off an MND promoter while the eGFP reporter is driven off an internal ribosomal entry site.

The following sequence is an exemplary lentiviral vector backbone for practicing the invention, e.g., to express PIM-1 in a cell, including a human cell, e.g., a stem cell or a cardiac or myocyte cell.

(SEQ ID NO: 4)

```
gacggatcgggagatctcccgatccctatggtcgactctcagtacaatctgctctgatgccgcatagttaagccagtatctgctccctgcttg tgtgttggaggtcgctgagtagtgcgcgagcaaaatttaagctacaacaaggcaaggcttgaccgacaattgcatgaagaatctgcttagg gttaggcgttttgcgctgcttcgcgatgtacgggccagatatacgcgttgacattgattattgactagttattaatagtaatcaattacggggtca ttagttcatagcccatatatggagttccgcgttacataacttacggtaaatggcccgcctggctgaccgcccaacgaccccgcccattgac gtcaataatgacgtatgttcccatagtaacgccaatagggactttccattgacgtcaatgggtggagtatttacggtaaactgcccacttggca gtacatcaagtgtatcatatgccaagtacgccccctattgacgtcaatgacggtaaatggcccgcctggcattatgcccagtacatgaccttat
```

-continued gggactttcctacttggcagtacatctacgtattagtcatcgctattaccatggtgatgcggttttggcagtacatcaatgggcgtggatagcg gtttgactcacggggatttccaagtctccaccccattgacgtcaatgggagtttgttttggcaccaaaatcaacgggactttccaaaatgtcgt aacaactccgcccattgacgcaaatgggcggtaggcgtgtacggtgggaggtctatataagcagcgcgttttgcctgtactgggtctctct ggttagaccagatctgagcctgggagctctctggctaactagggaacccactgcttaagcctcaataaagcttgccttgagtgcttcaagtag tgtgtgcccgtctgttgtgtgactctggtaactagagatccctcagacccttttagtcagtgtggaaaatctctagcagtggcgcccgaacag ggacctgaaagcgaaagggaaaccagaggagctctctcgacgcaggactcggcttgctgaagcgcgcacggcaagaggcgagggc ggcgactggtgagtacgccaaaaattttgactagcggaggctagaaggagagagatgggtgcgagagcgtcagtattaagcggggag aattagatcgcgatgggaaaaaattcggttaaggccagggggaaagaaaaaatataaattaaaacatatagtatgggcaagcagggagct agaacgattcgcagttaatcctggcctgttagaaacatcagaaggctgtagacaaatactgggacagctacaaccatcccttcagacaggat cagaagaacttagatcattatataatacagtagcaaccctctattgtgtgcatcaaaggatagagataaaagacaccaaggaagctttagaca agatagaggaagagcaaaacaaaagtaagaccaccgcacagcaagcggccgctgatcttcagacctggaggaggagatatgagggac aattggagaagtgaattatataaatataaagtagtaaaaattgaaccattaggagtagcacccaccaaggcaaagagaagagtggtgcaga gagaaaaaagagcagtgggaataggagctttgttccttgggttcttgggagcagcaggaagcactatgggcgcagcgtcaatgacgctga cggtacaggccagacaattattgtctggtatagtgcagcagcagaacaatttgctgagggctattgaggcgcaacagcatctgttgcaactc acagtctggggcatcaagcagctccaggcaagaatcctggctgtggaaagatacctaaaggatcaacagctcctggggatttggggttgct ctggaaaactcatttgcaccactgctgtgccttggaatgctagttggagtaataaatctctggaacagatttggaatcacacgacctggatgg agtgggacagagaaattaacaattacacaagcttaatacactccttaattgaagaatcgcaaaaccagcaagaaaagaatgaacaagaatt attggaattagataaatgggcaagtttgtggaattggtttaacataacaaattggctgtggtatataaaattattcataatgatagtaggaggctt ggtaggtttaagaatagttttgctgtactttctatagtgaatagagttaggcagggatattcaccattatcgtttcagacccacctcccaacccc gaggggacccgacaggcccgaaggaatagaagaagaaggtggagagagagacagagacagatccattcgattagtgaacggatccg atccacaaatggcagtattcatccacaatttttaaaagaaaaggggggattggggggtacagtgcaggggaaagaatagtagacataatag caacagacatacaaactaaagaattacaaaaacaaattacaaaaattcaaaattttcgggtttattacagggacagcagagatccagtttggc ctgcagagatccagagttaggcagggacattcaccattatcgtttcagacccacctcccaacccggtcatatgggaatgaaagaccccac ctgtaggtttggcaagctaggatcaaggttaggaacagagagacagcagaatatgggccaaacaggatatctgtggtaagcagttcctgcc ccggctcagggccaagaacagttggaacaggagaatatgggccaaacaggatatctgtggtaagcagttcctgccccggctcagggcca agaacagatggtccccagatgcggtcccgccctcagcagtttctagagaaccatcagatgtttccagggtgccccaaggacctgaaatga ccctgtgccttatttgaactaaccaatcagttcgcttctcgcttctgttcgcgcgcttctgctcccgagctctatataagcagagctcgtttagtg aaccgtcagatcgcctggagacgccatccacgctgttttgacctccatagaagatcagttaattaagaattcgccctctccctccccccccc ctaacgttactggccgaagccgcttggaataaggccggtgtgcgtttgtctatatgttattttccaccatattgccgtcttttggcaatgtgaggg cccggaaacctggccctgtcttcttgacgagcattcctaggggtctttcccctctcgccaaaggaatgcaaggtctgttgaatgtcgtgaagg aagcagttcctctggaagcttcttgaagacaaacaacgtctgtagcgaccctttgcaggcagcggaaccccccacctggcgacaggtgcc tctgcggccaaaagccacgtgtataagatacacctgcaaaggcggcacaaccccagtgccacgttgtgagttggatagttgtggaaagag tcaaatggctctcctcaagcgtattcaacaaggggctgaaggatgcccagaaggtacccccattgtatgggatctgatctggggcctcggtg cacatgctttacatgtgtttagtcgaggttaaaaaaacgtctaggccccccgaaccacggggacgtggttttcctttgaaaaacacgatgata atatggccacaaccatggtgagcaagggcgaggagctgttcaccggggtggtgcccatcctggtcgagctggacggcgacgtaaacgg ccacaagttcagcgtgtccggcgagggcgagggcgatgccacctacggcaagctgaccctgaagttcatctgcaccaccggcaagctg cccgtgccctggcccaccctcgtgaccaccctgacctacggcgtgcagtgcttcagccgctaccccgaccacatgaagcagcacgacttc ttcaagtccgccatgcccgaaggctacgtccaggagcgcaccatcttcttcaaggacgacggcaactacaagacccgcgccgaggtgaa gttcgagggcgacaccctggtgaaccgcatcgagctgaagggcatcgacttcaaggaggacggcaacatcctggggcacaagctggag tacaactacaacagccacaacgtctatatcatggccgacaagcagaagaacggcatcaaggtgaacttcaagatccgccacaacatcgag gacggcagcgtgcagctcgccgaccactaccagcagaacacccccatcggcgacggccccgtgctgctgcccgacaaccactacctga -continued

```
gcacccagtccgccctgagcaaagaccccaacgagaagcgcgatcacatggtcctgctggagttcgtgaccgccgcgggatcactctc ggcatggacgagctgtacaagtaaagcggccgcactgttctcatcacatcatatcaaggttatataccatcaatattgccacagatgttacttagcct tttaatatttctctaatttagtgtatatgcaatgatagttctctgatttctgagattgagtttctcatgtgtaatgattatttagagtttctctttcatctg ttcaaatttttgtctagattattttttactgatttgtaagacttattttataatctgcatattacaattctctttactggggtgttgcaaatattttctgtc attctatggcctgacttttcttaatggttttttaattttaaaaataagtcttaatattcatgcaatctaattaacaatcttttctttgtggttaggactttga gtcataagaaattttctctacactgaagtcatgatggcatgcttctatatttttctaaaagatttaaagttttgccttctccatttagacttataattc actggaattttttgtgtgtatggtatgacatatgggttccctttatttttacatataaatatatttccctgttttctaaaaagaaaaagatcatcat tttcccattgtaaaatgccatatttttttcataggtcacttacatatatcaatgggtctgtttctgagctctactctattttatcagcctcactgtctatcc ccacacatctcatgctttgctctaaatcttgatatttagtggaacattctttcccattttgttctacaagaatattttttgttattgtctttgggctttctata tacattttgaaatgaggttgacaagtttctagagttaactcgagggatcaagcttatcgataatcaacctctggattacaaaatttgtgaaagatt gactggtattcttaactatgttgctccttttacgctatgtggatacgctgattaatgcctttgtatcatgctattgcttcccgtatggctttcattttctc ctccttgtataaatcctggttgctgtctctttatgaggagttgtggcccgttgtcaggcaacgtggcgtggtgtgcactgtgtttgctgacgcaa ccccactggttggggcattgccaccacctgtcagctcattccgggactttcgctttccccctcccattgccacggcggaactcatcgccg cctgccttgcccgctgctggacaggggctcggctgttgggcactgacaattccgtggtgttgtcgggaagctgacgtcctttccatggctg ctcgcctgtgttgccacctggattctgcgcgggacgtccttctgctacgtcccttcggccctcaatccagcggaccttccttcccgcggcctg ctgccggctctgcggcctcttccgcgtcttcgccttcgccctcagacgagtcggatctcccctttgggccgcctccccgcatcgataccgtcg agacctagaaaaacatggagcaatcacaagtagcaacacagcagctaccaatgctgattgtgcctggctagaagcacaagaggaggag gaggtgggttttccagtcacacctcaggtacctttaagaccaatgacttacaaggcagctgtagatcttagccacttttttaaaagaaaagggg ggactggaagggctaattcactcccaacgaagacaagatatccttgatctgtggatctaccacacacaaggctacttccctgattggcagaa ctacacaccagggccagggatcagatatccactgacctttggatggtgctacaagctagtaccagttgagcaagagaaggtagaagaagc caatgaaggagagaacacccgcttgttacaccctgtgagcctgcatgggatggatgacccggagagagaagtattagagtggaggtttga cagccgcctagcatttcatcacatggcccgagagctgcatccggactgtactgggtctctctggttagaccagatctgagcctgggagctct ctggctaactagggaacccactgcttaagcctcaataaagcttgccttgagtgatcaagtagtgtgtgcccgtctgttgtgtgactctggtaa ctagagatccctcagacccttttagtcagtgtggaaaatctctagcagggcccgtttaaacccgctgatcagcctcgactgtgccttctagttg ccagccatctgttgtttgcccctcccccgtgccttccttgaccctggaaggtgccactcccactgtcctttcctaataaaatgaggaaattgcat cgcattgtctgagtaggtgtcattctattctgggggtggggtggggcaggacagcaaggggggaggattgggaagacaatagcaggcat gctgggatgcggtgggctctatggcttctgaggcggaaagaaccagctggggctctaggggtatccccacgcgccctgtagcggcg cattaagcgcggcgggtgtggtggttacgcgcagcgtgaccgctacacttgccagcgccctagcgcccgctcctttcgctttcttcccttcct ttctcgccacgttcgccggcttccccgtcaagctctaaatcggggcatccctttagggttccgatttagtgctttacggcacctcgaccccaa aaaacttgattagggtgatggttcacgtagtgggccatcgccctgatagacggtttttcgccctttgacgttggagtccacgttctttaatagtg gactcttgttccaaactggaacaacactcaacccatctcggtctattcttttgatttataaggggatttttggggatttcggcctattggttaaaaaat gagcgatttaacaaaaattttaacgcgaattaattctgtggaatgtgtgtcagttagggtgtggaaagtccccaggctccccaggcaggcag aagtatgcaaagcatgcatctcaattagtcagcaaccaggtgtggaaagtccccaggctccccagcaggcagaagtatgcaaagcatgca tctcaattagtcagcaaccatagtcccgcccctaactccgcccatcccgcccctaactccgcccagttccgcccattctccgccccatggct gactaattttttttatttatgcagaggccgaggccgcctctgcctctgagctattccagaagtagtgaggaggcttttttggaggcctaggcttt gcaaaaagctcccgggagcttgtatatccattttcggatctgatcagcacgtgttgacaattaatcatcggcatagtatatcggcatagtataat acgcaaggtgaggaactaaaccatggccaagttgaccagtgccgttccggtgctcaccgcgcgcgacgtcgccggagcggtcgagttc tggaccgaccggctcgggttctcccgggacttcgtggaggacgacttcgccggtgtggtccgggacgacgtgaccctgttcatcagcgcg gtccaggaccaggtggtgccggacaacacccctggcctgggtgtgggtgcgcggcctggacgagctgtacgccgagtggtcggaggtc gtgtccacgaacttccgggacgcctccgggccggccatgaccgagatcggcgagcagccgtgggggcgggagttcgccctgcgcgac
```

-continued
```
ccggccggcaactgcgtgcacttcgtggccgaggagcaggactgacacgtgctacgagatttcgattccaccgccgccttctatgaaagg ttgggctcggaatcgttttccgggacgccggctggatgatcctccagcgcggggatctcatgctggagttcttcgcccacccccaacttgttt attgcagcttataatggttacaaataaagcaatagcatcacaaatttcacaaataaagcattttttttcactgcattctagttgtggtttgtccaaact catcaatgtatcttatcatgtctgtataccgtcgacctctagctagagcttggcgtaatcatggtcatagctgtttcctgtgtgaaattgttatccgc tcacaattccacacaacatacgagccggaagcataaagtgtaaagcctggggtgcctaatgagtgagctaactcacattaattgcgttgcgc tcactgcccgctttccagtcgggaaacctgtcgtgccagctgcattaatgaatcggccaacgcgcggggagaggcggtttgcgtattgggc gctcttccgcttcctcgctcactgactcgctgcgctcggtcgttcggctgcggcgagcggtatcagctcactcaaaggcggtaatacggttat ccacagaatcaggggataacgcaggaaagaacatgtgagcaaaaggccagcaaaaggccaggaaccgtaaaaaggccgcgttgctgg cgtttttccataggctccgcccccctgacgagcatcacaaaaatcgacgctcaagtcagaggtggcgaaacccgacaggactataaagat accaggcgtttccccctggaagctccctcgtgcgctctcctgttccgaccctgccgcttaccggatacctgtccgcctttctcccttcgggaa gcgtggcgctttctcaatgctcacgctgtaggtatctcagttcggtgtaggtcgttcgctccaagctgggctgtgtgcacgaaccccccgttc agcccgaccgctgcgccttatccggtaactatcgtcttgagtccaacccggtaagacacgacttatcgccactggcagcagccactggtaa caggattagcagagcgaggtatgtaggcggtgctacagagttcttgaagtggtggcctaactacggctacactagaaggacagtatttggt atctgcgctctgctgaagccagttaccttcggaaaaagagttggtagctcttgatccggcaaacaaaccaccgctggtagcggtggtttttttg tttgcaagcagcagattacgcgcagaaaaaaaggatctcaagaagatcctttgatcttttctacggggtctgacgctcagtggaacgaaaac tcacgttaagggattttggtcatgagattatcaaaaaggatcttcacctagatccttttaaattaaaaatgaagttttaaatcaatctaaagtatata tgagtaaacttggtctgacagttaccaatgcttaatcagtgaggcacctatctcagcgatctgtctatttcgttcatccatagttgcctgactccc cgtcgtgtagataactacgatacgggagggcttaccatctggccccagtgctgcaatgataccgcgagacccacgctcaccggctccaga tttatcagcaataaaccagccagccggaagggccgagcgcagaagtggtcctgcaactttatccgcctccatccagtctattaattgttgccg ggaagctagagtaagtagttcgccagttaatagtttgcgcaacgttgttgccattgctacaggcatcgtggtgtcacgctcgtcgtttggtatg gcttcattcagctccggttcccaacgatcaaggcgagttacatgatccccatgttgtgcaaaaaagcggttagctccttcggtcctccgatc gttgtcagaagtaagttggccgcagtgttatcactcatggttatggcagcactgcataattctcttactgtcatgccatccgtaagatgcttttctg tgactggtgagtactcaaccaagtcattctgagaatagtgtatgcggcgaccgagttgctcttgcccggcgtcaatacgggataataccgcg ccacatagcagaactttaaaagtgctcatcattggaaaacgttatcggggcgaaaactacaaggatataccgctgttgagatccagttcg atgtaacccactcgtgcacccaactgatcttcagcatcttttactttcaccagcgtttctgggtgagcaaaaacaggaaggcaaatgccgca aaaaagggaataagggcgacacggaaatgttgaatactcatactcttccttttcaatattattgaagcatttatcagggttattgtacatgagc ggatacatatttgaatgtatttagaaaaataaacaaatagggggttccgcgcacatttccccgaaaagtgccacctgacgtc
```

EXAMPLE 5

Exemplary PIM Sequences Used to Practice this Invention

The invention provides compositions and methods comprising use of PIM-expressing nucleic acids and PIM polypeptides.

For example, in one embodiment the Human PIM-1 protein is used to practice the compositions and methods of this invention; an exemplary Human PIM-1 protein that can be used is Genbank accession no. AAA36447 (see also, e.g., Domen (1987) Oncogene Res. 1 (1):103-112) (SEQ ID NO:5):

(SEQ ID NO: 5)
```
  1 mllskinsla hlraapcndl hatklapgke keplesqyqv gpllgsggfg svysgirvsd 61 nlpvaikhve kdrisdwgel pngtrvpmev vllkkvssgf sgvirlldwf erpdsfvlil 121 erpepvqdlf dfitergalq eelarsffwq vleavrhchn cgvlhrdikd enilidlnrg 181 elkliidfgsg allkdtvytd fdgtrvyspp ewiryhryhg rsaavwslgi llydmvcgdi 241 pfehdeeiir gqvffrqrvs secqhlirwc lalrpsdrpt feeiqnhpwm qdvllpqeta 301 eihlhslspg psk
```

In one embodiment, a Human PIM-1 protein isoform is used to practice the compositions and methods of this invention; an exemplary Human PIM-1 protein isoform that can be used is the human pim-1 kinase 44 kDa isoform, see e.g., Genbank accession no. AAY87461 (see also, e.g., Xie (2006) Oncogene 25 (1), 70-78) (SEQ ID NO:6):

```
                                                              (SEQ ID NO: 6)
    1 mphepheplt ppfsalpdpa gapsrrqsrq rpqlssdsps afrasrshsr natrshshsh
   61 sprhslrhsp gsgscgsssg hrpcadilev gmllskinsl ahlraapcnd lhatklapgk
  121 ekeplesqyq vgpllgsggf gsvysgirvs dnlpvaikhv ekdrisdwge lpngtrvpme
  181 vvllkkvssg fsgvirlldw ferpdsfvli lerxepvqdl fdfitergal qeelarsffw
  241 qvleavrhch ncgvlhrdik denilidlnr gelklidfgs gallkdtvyt dfdgtrvysp
  301 pewiryhryh grsaavwslg illydmvcgd ipfehdeeii rgqvffrqry ssecqhlirw
  361 clalrpsdrp tfeeignhpw mqdvllpqet aeihlhslsp gpsk
```

In one embodiment, a Human PIM-1 message (mRNA) is used to practice the compositions and methods of this invention; an exemplary Human PIM-1 message that can be used is Genbank accession no. NM_002648 (see also, e.g., Zhang (2007) Mol. Cancer. Res. 5 (9), 909-922) (SEQ ID NO:7):

```
                                                              (SEQ ID NO: 7)
    1 cccgagagga gtcggtggca gcggcggcgg cgggaccggc agcagcagca gcagcagcag
   61 cagcaaccac tagcctcctg ccccgcggcg ctgccgcacg agcccacga gccgctcacc
  121 ccgccgttct cagcgctgcc cgaccccgct ggcgcgccct ccgccgcca gtcccggcag
  181 cgccctcagt tgtcctccga ctcgccctcg gccttccgcg ccagccgcag ccacagccgc
  241 aacgccaccc gcagccacag ccacagccac agcccaggc atagccttcg gcacagcccc
  301 ggctccggct cctgcggcag ctcctctggg caccgtccct gcgccgacat cctggaggtt
  361 gggatgctct tgtccaaaat caactcgctt gcccacctgc gcgccgcgcc ctgcaacgac
  421 ctgcacgcca ccaagctggc gcccggcaag gagaaggagc cctggagtc gcagtaccag
  481 gtgggcccgc tactgggcag cggcggcttc ggctcggtct actcaggcat ccgcgtctcc
  541 gacaacttgc cggtggccat caaacacgtg gagaaggacc ggatttccga ctggggagag
  601 ctgcctaatg gcactcgagt gcccatggaa gtggtcctgc tgaagaaggt gagctcgggt
  661 ttctccggcg tcattaggct cctggactgg ttcgagaggc ccgacagttt cgtcctgatc
  721 ctggagaggc ccgagccggt gcaagatctc ttcgacttca tcacggaaag gggagccctg
  781 caagaggagc tggcccgcag cttcttctgg caggtgctgg aggccgtgcg gcactgccac
  841 aactgcgggg tgctccaccg cgacatcaag gacgaaaaca tccttatcga cctcaatcgc
  901 ggcgagctca agctcatcga cttcgggtcg ggggcgctgc tcaaggacac cgtctacacg
  961 gacttcgatg ggacccgagt gtatagccct ccagagtgga tccgctacca tcgctaccat
 1021 ggcaggtcgg cggcagtctg gtccctgggg atcctgctgt atgatatggt gtgtggagat
 1081 attcctttcg agcatgacga agagatcatc aggggccagg ttttcttcag gcagagggtc
 1141 tcttcagaat gtcagcatct cattagatgg tgcttggccc tgagaccatc agataggcca
 1201 accttcgaag aaatccagaa ccatccatgg atgcaagatg ttctcctgcc caggaaact
 1261 gctgagatcc acctccacag cctgtcgccg gggcccagca aatagcagcc tttctggcag
 1321 gtcctcccct ctcttgtcag atgcccgagg aggggaagc ttctgtctcc agcttcccga
 1381 gtaccagtga cacgtctcgc caagcaggac agtgcttgat acaggaacaa catttacaac
 1441 tcattccaga tcccaggccc ctggaggctg cctcccaaca gtggggaaga gtgactctcc
 1501 aggggtccta ggcctcaact cctcccatag atactctctt cttctcatag gtgtccagca
```

-continued

```
1561 ttgctggact ctgaaatatc ccggggtgg ggggtgggggg tgggtcagaa ccctgccatg 1621 gaactgtttt cttcatcatg agttctgctg aatgccgcga tgggtcaggt aggggggaaa 1681 caggttggga tgggatagga ctagcaccat tttaagtccc tgtcacctct tccgactctt 1741 tctgagtgcc ttctgtgggg actccggctg tgctgggaga aatacttgaa cttgcctctt 1801 ttacctgctg cttctccaaa aatctgcctg ggttttgttc cctattttc tctcctgtcc 1861 tccctcaccc cctccttcat atgaaaggtg ccatggaaga ggctacaggg ccaaacgctg 1921 agccacctgc cctttttct gcctccttta gtaaaactcc gagtgaactg gtcttccttt 1981 ttggttttta cttaactgtt tcaaagccaa gacctcacac acacaaaaaa tgcacaaaca 2041 atgcaatcaa cagaaaagct gtaaatgtgt gtacagttgg catggtagta tacaaaaga 2101 ttgtagtgga tctaattttt aagaaatttt gcctttaagt tattttacct gttttgttt 2161 cttgttttga aagatgcgca ttctaacctg gaggtcaatg ttatgtattt atttatttat 2221 ttatttggtt cccttcctat tccaagcttc catagctgct gccctagttt tctttcctcc 2281 tttcctcctc tgacttgggg accttttggg ggagggctgc gacgcttgct ctgtttgtgg 2341 ggtgacggga ctcaggcggg acagtgctgc agctccctgg cttctgtggg gcccctcacc 2401 tacttaccca ggtgggtccc ggctctgtgg gtgatgggga ggggcattgc tgactgtgta 2461 tataggataa ttatgaaaag cagttctgga tggtgtgcct tccagatcct ctctgggct 2521 gtgttttgag cagcaggtag cctgctggtt ttatctgagt gaaatactgt acaggggaat 2581 aaaagagatc ttatttttt ttttatactt ggcgttttt gaataaaaac cttttgtctt 2641 aaaaaaaaaa aaaaaaaa aaaaaaaaaa aaaaaaaa aaaa
```

In one embodiment, a Human PIM-1 gene is used to practice the compositions and methods of this invention; an exemplary Human PIM-1 gene that can be used is (SEQ ID NO:8):

LOCUS NC_000023 5826 by DNA linear CON 3 Mar. 2008
DEFINITION *Homo sapiens* chromosome X, reference assembly, complete sequence.
ACCESSION NC_000023 REGION: complement (48655403..48661228)
VERSION NC_000023.9 GI:89161218
PROJECT GenomeProject:168
SOURCE *Homo sapiens* (human)
  ORGANISM *Homo sapiens*
REFERENCE 1 (bases 1 to 5826)
  AUTHORS International Human Genome Sequencing Consortium.
  TITLE Finishing the euchromatic sequence of the human genome
  JOURNAL Nature 431 (7011), 931-945 (2004)
  PUBMED 15496913

(SEQ ID NO: 8)
```
  1 cgcgcgcggc gaatctcaac gctgcgccgt ctgcgggcgc ttccgggcca ccagtttctc 61 tgctttccac cctggcgccc cccagccctg gctccccagc tgcgctgccc cgggcgtcca 121 cgccctgcgg gcttagcggg ttcagtgggc tcaatctgcg cagcgccacc tccatgttga 181 ccaagcctct acaggggcct cccgcgcccc ccgggacccc cacgccgccg ccaggtgagt 241 acatcctccc ctactgcaac cagacggggt gggctggaat gatgggttgc agcgcggggg 301 gagggagtcg tggctgggct cagcacgccg ccaccctgac ttcctcgcct ccgcctgcgt 361 aggaggcaag gatcgggaag cgttcgaggc cgagtatcga ctcggccccc tcctgggtaa 421 gggggctttt ggcaccgtct tcgcaggaca ccgcctcaca gatcgactcc aggtatccgt 481 catgagggtc ttgggagggt caggtgcgtg tggcggggc ggggtcctg gccctggaat 541 gctggttgac cgaggagtga gcctgcagag tgtgtagagg accaggtgtg tgtgtgtgtg 601 tgtccgtgtc cgtgtccgag gagtgagcct gcagtgtgtg tagagggcca ggtgtgtgtg 661 cgtgcgcgtg tgtgtgtcgg tctaggaggt tatgggcggg ggggggggc aggggcttc 721 agattccgga gttccttgac cccggggtcc aggctgtgta tgtgtgggaa agcagggacc
```

-continued

```
 781 tagatgtgag atttgtggga cttttggagg taggtgtcca gtgtggagtc atgcggacca
 841 ggaccctggt acagagttgg ggtgtcgtag agctaaatag gaagattgtg ggcctgggt
 901 atcaggaaat ctagaactca ggacttggag tgatgagtcc tgatgcctga gaacggagag
 961 cccagggcta aggaaggtgg gagagataaa cttggttccg aggacctgga gggcagggga
1021 gacgccctgg tacgcgttct gtggggtgct gtggttgggg accagaaaga ctagagtgct
1081 ggtagatgga ggaatactgg aggtaggcag aaggtctaga ctgggagggg tctggggatc
1141 acctgctggc ctccttatca cggccttctt ctccaggtgg ccatcaaagt gattccccgg
1201 aatcgtgtgc tgggctggtc cccttggtg agtaccttcg gagcccttcc taacctacct
1261 actccatcac tgatgtattc acctccttgc ttttccaggg gatgtatgac tccctgggcc
1321 ctgtaacagt gagaatactg ccagtccatt tatactccct tggggtgaca tacagttctg
1381 attcacccca attcccctag agccctggat tctcccctcc aacaaacctt taccatcctt
1441 cctccaaaca ctgctggggg actgcccgca gggcgtgctg gtggggaaca aggggcagag
1501 gtcactggtt gccatggtga tggtggctgc ttctctcttg ccgttataac gctaacggac
1561 atcagggcgg gtctgggcaa gttgtagagt tgggagcgcc ccctggcggg ctctagggga
1621 aactgcgcct gcgcagtcca tgggacccaa agggagaggg tgcgcctgcg caatatcggt
1681 atttttgcat ctcggtgaga aaacgtctgc tgccgtgcaa gtcagcagcc tggccaggag
1741 agggctctac ctcatcccag aaggttgctg ctcgaagtgt acctgcgcag ggcttgggga
1801 ggcagtgggg ggcggatttt gtggccccca gcgtttatac tttttttttt ttggagacac
1861 agtctccctc tgttgcccag gctggagtga ggtgacgcga tctcggctca ctgcaacctc
1921 cgtctcctgg gttcaagtga ttctcctgcc tcagcctccc aagtagctgg gactacagga
1981 gcgcacaacc atgcccggct aattttttgta tttttagtag agacagggtt tcaccatgtt
2041 ggccaggcgg ttttgaact gctgacctca ggtgatccgc ctgcctcggc cactcaaagt
2101 gctgggatta caggcatgag ccaccacgcc cggctgcatt tatgactttt ttttttcctt
2161 gagacggagt ttcgctctgc tgcctgggct ggagtgcagt ggcgtgatct cagctcactg
2221 cagcctccac ctcctgggtt caagcgattc tcctgcctca ggctcctgag tagctggaat
2281 tacaggcacc cgctgccatg cccggctaag ttttacgttt ttagtagaga ccgtgtttca
2341 ccatgttggc caggctggtc tcgaacccct gacctagtga tctgcccgcc ttgggcctcc
2401 caaagtgctg ggattacagg cgtgagccac cgcgcccagc ctctaatttt gtatttttag
2461 tagagacggg gtttctccat gttggtcagg ctggtctcga actcccgacc tcaggtgatc
2521 tgcccgtctc ggcctcccaa agtgctggga ttacaggcgt gagccactgc gcagggccac
2581 atttaggctt tttattggct ggttctaggt gcttggtgat gctgacaaaa cacatgataa
2641 cactaagtcc ttttgtgcta ggtcctttgt aataaatcac tcagctgttt aacaaattag
2701 gtatattgac cacctactat atgacagaca taattctaga cactcagcaa agtattacat
2761 aagtattgag agctcatttt gtgctaggtc ctttttact aattgttttc acctgtttaa
2821 caaatattta ttcagcccta ctctgttagc agccactgtt ctagtgcttc atatacgtcc
2881 gtgaacaaaa caaaccatta cacaataagt gtttattgag tgctaactgc ttgtcagagc
2941 ccatgctatt aagtgctgtc atctgtttaa catttattga tcacctgtgt aaggtactat
3001 tctaatctgg gatatgtcag ggaacaaaac aaaacacata atggtggtgc tgcttctgct
3061 gaaagccttc agttgataac cagatttttc tttgtatttt tgcttgtttg ttttgagaca
3121 gctggagtgc agtggtgtga tcttcactgc aacctctgcc ttcttggctc aagcgaccct
3181 cccacctgag cctcccaagt agctgggact acaggtgcat gccaccaagc ctggctaatt
```

```
3241 tttgtgtttg tgccattttg cccaggctga tcttgaactc ttgggctcaa gcaatccacc
3301 cacatcagcc tcccaaagtg ctgggattgc agggatgagc cactgtgcct ggccgaactt
3361 ctttcgttta ttcaaatgtt tattgatcta cgacatgcga gatttgtgca ggctctttgc
3421 tggtttcacc ctctcaatcg ctgtgtgagt ttgtgtcttt agggaaagtg aggcccagga
3481 agggaagtga gttgcttagc gacacactgt caggaaaagg ggccctgagt tgagcttagg
3541 taaaaagcct cagagctgtt gccctgacat ctgtcttttt tctctccctg cttcccaccc
3601 cacctgtgcc cccagtcaga ctcagtcaca tgcccactcg aagtcgcact gctatggaaa
3661 gtgggtgcag gtggtgggca ccctggcgtg atccgcctgc ttgactggtt tgagacacag
3721 gagggcttca tgctggtcct cgagcggcct ttgcccgccc aggatctctt tgactatatc
3781 acagagaagg gccactgggt gaaggccca agccgctgct tctttggcca agtagtggca
3841 gccatccagc actgccattc ccgtggagtt gtccatcgtg acatcaagga tgagaacatc
3901 ctgatagacc tacgccgtgg ctgtgccaaa ctcattgatt ttggttctgg tgccctgctt
3961 catgatgaac cctacactga ctttgatggt aaggcttctc taaatctccc tggagggatt
4021 gttttttactt gatggccttg tgacctttgg cctccagtgg tggggtgtcc tgtaatcctt
4081 gacccatact gcattatata agatgatcga ttgctaatac tggggattct cagccttgcc
4141 ctctgataaa gtccatcttt taatggtgtg ctaaccttat tctgggctcc tattctggtg
4201 aggggatcct gttaccatcc tgagtattct ttctctggta aggggatcct gttactttc
4261 agtgctttta ttctgttgag gggactctgt tattttagct gcttttatc tagtgagggg
4321 actctgcttt tatcttgagt gctcttaatt gtggtgaggc catccttcct ggagagtttg
4381 gggttggaga agggcatcat gagattgagt tggtctaacc cctggcttgt gtgcagggac
4441 aagggtgtac agcccccag agtggatctc tcgacaccag taccatgcac tcccggccac
4501 tgtctggtca ctgggcatcc tcctctatga catggtgtgt gggacattc cctttgagag
4561 ggaccaggag attctggaag ctgagctcca cttcccagcc catgtctccc caggtgaggc
4621 ctcactgacc ccagcccaga agactccatc cttctcaggg accagtaccc cctactgact
4681 gctaatcttc cctctctgct tcttggccta cagactgctg tgccctaatc cgccggtgcc
4741 tggcccccaa accttcttcc cgaccctcac tggaagagat cctgctggac ccctggatgc
4801 aaacaccagc cgaggatgta cccctcaacc cctccaaagg aggccctgcc cctttggcct
4861 ggtccttgct accctaagcc tggcctggcc tggcctggcc cccaatggtc agaagagcca
4921 tcccatggcc atgtcacagg gatagatgga catttgttga cttggtttta caggtcatta
4981 ccagtcatta aagtccagta ttactaaggt aagggattga ggatcagggg ttagaagaca
5041 taaaccaagt ctgcccagtt cccttcccaa tcctacaaag gagccttcct cccagaacct
5101 gtggtccctg attctggagg gggaacttct tgcttctcat tttgctaagg aagtttattt
5161 tggtgaagtt gttcccattc tgagccccgg gactcttatt ctgatgatgt gtcaccccac
5221 attggcacct cctactacca ccacacaaac ttagttcata tgctcttact tgggcaaggg
5281 tgctttcctt ccaataccccc agtagctttt attttagtaa agggacccctt tccctagcc
5341 tagggtccca tattgggtca agctgcttac ctgcctcagc ccaggattct ttattctggg
5401 ggaggtaatg cccctgttgtt accccaaggc ttcttttttt ttttttttt tttgggtgag
5461 gggaccctac tctgttatcc caagtgctct tattctggtg agaagaacct tacttccata
5521 atttgggaag gaatggaaga tggacaccac cggacaccac cagacactag gatgggatgg
5581 atggtttttt gggggatggg ctaggggaaa taaggcttgc tgtttgttct cctggggcgc
```

```
5641 tccctccaac ttttgcagat tcttgcaacc tcctcctgag ccgggattgt ccaattacta 5701 aaatgtaaat aatcacgtat tgtggggagg ggagttccaa gtgtgccctc ctctcttctc 5761 ctgcctggat tatttaaaaa gccatgtgtg gaaacccact atttaataaa agtaatagaa 5821 tcagaa
```

In one embodiment, exemplary Human PIM-1 polypeptides and message that can be used are:

(SEQ ID NO: 9)

MLLSKFGSLAHLCGPGGVDHLPVKILQPAKADKESFEKAYQVGA (SEQ ID NO: 10)

VLGSGGEGTVYAGSRIADGLPVAVKHVVKERVTEWGSLGGATVPLEVVLLRKVGAAGG

ARGVIRLLDWFERPDGFLLVLERPEPAQDLFDFITERGALDEPLARRFFAQVLAAVRH

CHSCGVVHRDIKDENLLVDLRSGELKLIDFGSGALLKDTVYTDFDGTRVYSPPEWIRY

HRYHGRSATVWSLGVLLYDMVCGDIPFEQDEEILRGRLLFRRRVSPECQQLIRWCLSL

RPSERPSLDQIAAHPWMLGADGGAPESCDLRLCTLDPDDVASTTSSSESL"

(SEQ ID NO: 11)
```
   1 agcggaccga cgcgacacgc cgtgcgcctc cgcggctgcg ctacgaaaac gagtcccgga 61 gcggccccgc gcccgccgca cccggccctc gcccacccga agacaggcgc ccagctgccc 121 cgccgtctcc ccagctagcg cccggccgcc gccgcctcgc gggcccgggg cggaagggggg 181 cggggtcccg attcgccccg ccccccgcgga gggatacgcg gcgccgcggc ccaaaacccc 241 cgggcgaggc ggccgggggcg ggtgaggcgc tccgcctgct gctcgtctac gcggtccccg 301 cgggccttcc gggcccactg cgccgcgcgg accgcctcgg gctcggacgg ccggtgtccc 361 cggcgcgccg ctcgcccgga tcggccgcgg cttcggcgcc tggggctcgg ggctccgggg 421 aggccgtcgc ccgcgatgct gctctccaag ttcggctccc tggcgcacct ctgcgggccc 481 ggcggcgtgg accacctccc ggtgaagatc ctgcagccag ccaaggcgga caaggagagc 541 ttcgagaagg cgtaccaggt gggcgccgtg ctgggtagcg gcggcttcgg cacggtctac 601 gcgggtagcc gcatcgccga cgggctcccg gtggctgtga agcacgtggt gaaggagcgg 661 gtgaccgagt ggggcagcct gggcggcgcg accgtgcccc tggaggtggt gctgctgcgc 721 aaggtgggcg cggcgggcgg cgcgcgcggc gtcatccgcc tgctggactg gttcgagcgg 781 cccgacggct tcctgctggt gctggagcgg cccgagccgg cgcaggacct cttcgacttt 841 atcacggagc gcggcgccct ggacgagccg ctggcgcgcc gcttcttcgc gcaggtgctg 901 gccgccgtgc gccactgcca cagctgcggg gtcgtgcacc gcgacattaa ggacgaaaat 961 ctgcttgtgg acctgcgctc cggagagctc aagctcatcg acttcggttc gggtgcgctg 1021 ctcaaggaca cggtctacac cgacttcgac ggcacccgag tgtacagccc ccggagtgg 1081 atccgctacc accgctacca cgggcgctcg gccaccgtgt ggtcgctggg cgtgcttctc 1141 tacgatatgg tgtgtgggga catcccccttc gagcaggacg aggagatcct ccgaggccgc 1201 ctgctcttcc ggaggagggt ctctccagag tgccagcagc tgatccggtg gtgcctgtcc 1261 ctgcggccct cagagcggcc gtcgctggat cagattgcgg cccatccctg gatgctgggg 1321 gctgacgggg gcgccccgga gagctgtgac ctgcggctgt gcaccctcga ccctgatgac 1381 gtggccagca ccacgtccag cagcgagagc ttgtgaggag ctgcacctga ctgggagcta 1441 ggggaccacc tgccttggcc agacctggga cgccccaga ccctgacttt ttcctgcgtg 1501 ggccgtctcc tcctgcggaa gcagtgacct ctgacccctg gtgaccttcg ctttgagtgc
```

-continued

```
1561 cttttgaacg ctggtcccgc gggacttggt tttctcaagc tctgtctgtc caaagacgct
1621 ccggtcgagg tcccgcctgc cctgggtgga tacttgaacc ccagacgccc ctctgtgctg
1681 ctgtgtccgg aggcggcctt cccatctgcc tgcccacccg agctctttc cgccggcgca
1741 gggtcccaag cccacctccc gccctcagtc ctgcggtgtg cgtctgggca cgtcctgcac
1801 acacaatgca agtcctggcc tccgcgcccg cccgcccacg cgagccgtac ccgccgccaa
1861 ctctgttatt tatggtgtga cccccctggag gtgccctcgg cccaccgggg ctatttattg
1921 tttaatttat ttgttgaggt tatttcctct gagatgtctg cctctcccaa gccccagggg
1981 acagtgggga ggcaggggag ggggtggctg tggtccaggg accccaggcc ctgattcctg
2041 tgcctggcgt ctgtcctggc cccgcctgtc agaagatgaa catgtatagt ggctaactta
2101 agggagtgg gtgaccctga cacttccagg cactgtgccc agggtttggg ttttaaatta
2161 ttgactttgt acagtctgct tgtgggctct gaaagctggg gtggggccag agcctgagcg
2221 tttaatttat tcagtacctg tgtttgtgtg aatgcggtgt gtgcaggcat cgcagatggg
2281 ggttcttca gttcaaaagt gagatgtctg gagatcatat tttttatac aggtatttca
2341 attaaaatgt ttttgtacat aaaaaaaaaa aaaaaaaaa aaaaaaaaa aa
```

(SEQ ID NO: 12)

Agcttcgaattatgctcttgtccaaaatcaactcgcttgcccacctgcgcgccgcgccctgcaacgacctgcacgccaccaagc
tggcgcccggcaaggagaaggagcccctggagtcgcagtaccaggtgggcccgctactgggcagcggcggcttcggctcggtctactc
aggcatccgcgtctccgacaacttgccggtggccatcaaacacgtggagaaggaccggatttccgactggggagagctgcctaatggca
ctcgagtgcccatggaagtggtcctgctgaagaaggtgagctcgggtttctccggcgtcattaggctcctgactggttcgagaggcccga
cagtttcgtcctgatcctggagaggcccgagccggtgcaagatctcttcgacttcatcacggaaaggggagccctgcaagaggagctggc
ccgcagcttcttctggcaggtgctggaggccgtgcggcactgccacaactgcggggtgctccaccgcgacatcaaggacgaaaacatcc
ttatcgacctcaatcgcggcgagctcaagctcatcgacttcgggtcgggggcgctgctcaaggacaccgtctacacggacttcgatggga
cccgagtgtatagccctccagagtggatccgctaccatcgctaccatggcaggtcggcggcagtctggtccctgggatcctgctgtatga
tatggtgtgtggagatattcctttcgagcatgacgaagagatcatcagggggccaggttttcttcaggcagagggtctcttcagaatgtcagcat
ctcattagatggtgcttggccctgagaccatcagataggccaaccttcgaagaaatccagaaccatccatggatgcaagatgttctcctgcc
ccaggaaactgctgagatccacctccacagcctgtcgccggggcccagcagcctgtcgccggggcccagcaaacaattggtaccgcgg
gcccgg (SEQ ID NO: 13)

```
    atgctct tgtccaaaat caactcgctt gcccacctgc gcgccgcgcc ctgcaacgac
421 ctgcacgcca ccaagctggc gcccggcaag gagaaggagc ccctggagtc gcagtaccag
481 gtgggcccgc tactgggcag cggcggcttc ggctcggtct actcaggcat ccgcgtctcc
541 gacaacttgc cggtggccat caaacacgtg gagaaggacc ggatttccga ctggggagag
601 ctgcctaatg gcactcgagt gcccatggaa gtggtcctgc tgaagaaggt gagctcgggt
661 ttctccggcg tcattaggct cctgactggt tcgagaggc cgacagtttt cgtcctgatc
721 ctggagaggc ccgagccggt gcaagatctc ttcgacttca tcacggaaag gggagccctg
781 caagaggagc tggcccgcag cttcttctgg caggtgctgg aggccgtgcg gcactgccac
841 aactgcgggg tgctccaccg cgacatcaag gacgaaaaca tccttatcga cctcaatcgc
901 ggcgagctca agctcatcga cttcgggtcg ggggcgctgc tcaaggacac cgtctacacg
961 gacttcgatg gacccgagt gtatagccct ccagagtgga tccgctacca tcgctaccat
1021 ggcaggtcgg cggcagtctg gtccctgggg atcctgctgt atgatatggt gtgtggagat
1081 attcctttcg agcatgacga agagatcatc aggggccagg ttttcttcag gcagagggtc
1141 tcttcagaat gtcagcatct cattagatgg tgcttggccc tgagaccatc agataggcca
```

-continued

```
1201 accttcgaag aaatccagaa ccatccatgg atgcaagatg ttctcctgcc ccaggaaact 1261 gctgagatcc acctccacag cctgtcgccg gggcccagca aatag
```

(SEQ ID NO: 14)

```
 100 a tgctcctgtc caagatcaac 121 tccctggccc acctgcgcgc cgcgccctgc aacgacctgc acgccaccaa gctggcgccg 181 ggcaaagaga aggagcccct ggagtcgcag taccaggtgg gcccgctgtt gggcagcggt 241 ggcttcggct cggtctactc tggcatccgc gtcgccgaca acttgccggt ggccattaag 301 cacgtggaga aggaccggat ttccgattgg ggagaactgc ccaatggcac ccgagtgccc 361 atggaagtgg tcctgttgaa gaaggtgagc tcggacttct cgggcgtcat tagacttctg 421 gactggttcg agaggcccga tagtttcgtg ctgatcctgg agaggcccga accggtgcaa 481 gacctcttcg actttatcac cgaacgagga gccctacagg aggacctggc ccgaggattc 541 ttctggcagg tgctggaggc cgtgcggcat tgccacaact gcgggttct ccaccgcgac 601 atcaaggacg agaacatctt aatcgacctg agccgcggcg aaatcaaact catcgacttc 661 gggtcggggg cgctgctcaa ggacacagtc tacacggact ttgatgggac ccgagtgtac 721 agtcctccag agtggattcg ctaccatcgc taccacggca ggtcggcagc tgtctggtcc 781 cttgggatcc tgctctatga catggtctgc ggagatattc cgtttgagca cgatgaagag 841 atcatcaagg gccaagtgtt cttcaggcaa actgtctctt cagagtgtca gcaccttatt 901 aaatggtgcc tgtccctgag accatcagat cggccctcct ttgaagaaat ccggaaccat 961 ccatggatgc agggtgacct cctgcccag gcagcttctg agatccatct gcacagtctg 1021 tcaccggggt ccagcaagta g
```

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

---

What is claimed is:

1. A method for treating a cardiac injury in an individual, comprising:
introducing into the heart of the individual a population of autologous or allogeneic cardiac progenitor cells that have been engineered to contain an expression vector comprising a heterologous promoter operatively linked to a PIM-1 encoding polynucleotide sequence for over-expression of a PIM-1 kinase in the cardiac progenitor cells, wherein the introduced cardiac progenitor cells differentiate into functional cardiomyocytes in the heart in sufficient numbers to treat said cardiac injury.

2. The method of claim 1, wherein the promoter is an inducible promoter.

3. The method of claim 1, wherein the cardiac progenitor cells are c-kit+cells.

4. The method of claim 1, wherein the cardiac progenitor cells are human cardiac progenitor cells.

5. The method of claim 1, wherein the introduced cardiac progenitor cells provide improved cardiac function in the individual for at least 32 weeks.

6. The method of claim 1, wherein the PIM-1 encoding polynucleotide encodes a human-1.

7. The method of claim 1, wherein the cardiac injury is associated with a myocardial infarction.

8. The method of claim 1, wherein the cardiac injury is associated with a congestive heart failure.

* * * * *

UNITED STATES PATENT AND TRADEMARK OFFICE
CERTIFICATE OF CORRECTION

PATENT NO. : 8,617,534 B2  Page 1 of 1
APPLICATION NO. : 12/742871
DATED : December 31, 2013
INVENTOR(S) : Sussman et al.

It is certified that error appears in the above-identified patent and that said Letters Patent is hereby corrected as shown below:

In The Claims

In line 2 of claim 6, delete "human-1" and please insert -- "human PIM-1" --.

Claim 6 should read as follows: "The method of claim 1, wherein the PIM-1 encoding polynucleotide encodes a human PIM-1"

Signed and Sealed this
Fifth Day of April, 2016

Michelle K. Lee
*Director of the United States Patent and Trademark Office*

UNITED STATES PATENT AND TRADEMARK OFFICE
CERTIFICATE OF CORRECTION

PATENT NO. : 8,617,534 B2
APPLICATION NO. : 12/742871
DATED : December 31, 2013
INVENTOR(S) : Mark A. Sussman and John A. Muraski It is certified that error appears in the above-identified patent and that said Letters Patent is hereby corrected as shown below:

In the Specification

Column 1, Lines 19-24 under the heading "FEDERAL FUNDING," please delete the following: "This invention was produced in part using funds from the Federal government under one or more of the following grants 5R01HL067245, 1R01HL091102, 1P01HL085577, and 1P01AG023071, all from the National Institutes of Health. Accordingly, the Federal government has certain rights in this invention."

And insert the following:
--This invention was made with government support under grant numbers HL067245, HL085577, HL091102, AG023071, HL105759 awarded by the National Institutes of Health. The government has certain rights in the invention.--

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 3

<210> SEQ ID NO 1
<211> LENGTH: 313
<212> TYPE: PRT
<213> ORGANISM: Homo sapiens
<220> FEATURE:
<221> NAME/KEY: DOMAIN
<222> LOCATION: (1)...(313)
<223> OTHER INFORMATION: human PIM-1

<400> SEQUENCE: 1

Met Leu Leu Ser Lys Ile Asn Ser Leu Ala His Leu Arg Ala Ala Pro
  1               5                  10                  15

Cys Asn Asp Leu His Ala Thr Lys Leu Ala Pro Gly Lys Glu Lys Glu
             20                  25                  30

Pro Leu Glu Ser Gln Tyr Gln Val Gly Pro Leu Leu Gly Ser Gly Gly
         35                  40                  45

Phe Gly Ser Val Tyr Ser Gly Ile Arg Val Ser Asp Asn Leu Pro Val
     50                  55                  60

Ala Ile Lys His Val Glu Lys Asp Arg Ile Ser Asp Trp Gly Glu Leu
 65                  70                  75                  80

Pro Asn Gly Thr Arg Val Pro Met Glu Val Val Leu Leu Lys Lys Val
```

-continued

```
                85                  90                  95
Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125

Leu Phe Asp Phe Ile Thr Glu Arg Gly Ala Leu Gln Glu Glu Leu Ala
    130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310

<210> SEQ ID NO 2
<211> LENGTH: 405
<212> TYPE: PRT
<213> ORGANISM: Homo sapiens
<220> FEATURE:
<221> NAME/KEY: DOMAIN
<222> LOCATION: (1)...(405)
<223> OTHER INFORMATION: human pim-1 kinase 44 kDa isoform
<220> FEATURE:
<221> NAME/KEY: SITE
<222> LOCATION: 214
<223> OTHER INFORMATION: Xaa = any naturally occurring amino acid

<400> SEQUENCE: 2

Met Pro His Glu Pro His Glu Pro Leu Thr Pro Pro Phe Ser Ala Leu
1               5                   10                  15

Pro Asp Pro Ala Gly Ala Pro Ser Arg Arg Gln Ser Arg Gln Arg Pro
            20                  25                  30

Gln Leu Ser Ser Asp Ser Pro Ser Ala Phe Arg Ala Ser Arg Ser His
        35                  40                  45

Ser Arg Asn Ala Thr Arg Ser His Ser His Ser His Ser Pro Arg His
    50                  55                  60

Ser Leu Arg His Ser Pro Gly Ser Gly Ser Cys Gly Ser Ser Ser Gly
65                  70                  75                  80

His Arg Pro Cys Ala Asp Ile Leu Glu Val Gly Met Leu Leu Ser Lys
                85                  90                  95

Ile Asn Ser Leu Ala His Leu Arg Ala Ala Pro Cys Asn Asp Leu His
            100                 105                 110
```

Ala Thr Lys Leu Ala Pro Gly Lys Glu Lys Glu Pro Leu Glu Ser Gln
            115                 120                 125

Tyr Gln Val Gly Pro Leu Leu Gly Ser Gly Gly Phe Gly Ser Val Tyr
        130                 135                 140

Ser Gly Ile Arg Val Ser Asp Asn Leu Pro Val Ala Ile Lys His Val
145                 150                 155                 160

Glu Lys Asp Arg Ile Ser Asp Trp Gly Glu Leu Pro Asn Gly Thr Arg
                165                 170                 175

Val Pro Met Glu Val Val Leu Leu Lys Lys Val Ser Ser Gly Phe Ser
            180                 185                 190

Gly Val Ile Arg Leu Leu Asp Trp Phe Glu Arg Pro Asp Ser Phe Val
        195                 200                 205

Leu Ile Leu Glu Arg Xaa Glu Pro Val Gln Asp Leu Phe Asp Phe Ile
210                 215                 220

Thr Glu Arg Gly Ala Leu Gln Glu Glu Leu Ala Arg Ser Phe Phe Trp
225                 230                 235                 240

Gln Val Leu Glu Ala Val Arg His Cys His Asn Cys Gly Val Leu His
            245                 250                 255

Arg Asp Ile Lys Asp Glu Asn Ile Leu Ile Asp Leu Asn Arg Gly Glu
        260                 265                 270

Leu Lys Leu Ile Asp Phe Gly Ser Gly Ala Leu Leu Lys Asp Thr Val
275                 280                 285

Tyr Thr Asp Phe Asp Gly Thr Arg Val Tyr Ser Pro Pro Glu Trp Ile
            290                 295                 300

Arg Tyr His Arg Tyr His Gly Arg Ser Ala Ala Val Trp Ser Leu Gly
305                 310                 315                 320

Ile Leu Leu Tyr Asp Met Val Cys Gly Asp Ile Pro Phe Glu His Asp
                325                 330                 335

Glu Glu Ile Ile Arg Gly Gln Val Phe Phe Arg Gln Arg Val Ser Ser
            340                 345                 350

Glu Cys Gln His Leu Ile Arg Trp Cys Leu Ala Leu Arg Pro Ser Asp
        355                 360                 365

Arg Pro Thr Phe Glu Glu Ile Gln Asn His Pro Trp Met Gln Asp Val
370                 375                 380

Leu Leu Pro Gln Glu Thr Ala Glu Ile His Leu His Ser Leu Ser Pro
385                 390                 395                 400

Gly Pro Ser Lys Leu
                405

<210> SEQ ID NO 3
<211> LENGTH: 2684
<212> TYPE: DNA
<213> ORGANISM: Homo sapiens
<220> FEATURE:
<221> NAME/KEY: misc_feature
<222> LOCATION: (1)...(2684)
<223> OTHER INFORMATION: human pim-1 kinase message (mRNA)

<400> SEQUENCE: 3
cccgagagga gtcggtggca gcggcggcgg cgggaccggc agcagcagca gcagcagcag    60
cagcaaccac tagcctcctg ccccgcggcg ctgccgcacg agcccacgga gccgctcacc   120
ccgccgttct cagcgctgcc cgaccccgct ggcgcgccct cccgccgcca gtcccggcag   180
cgccctcagt tgtcctccga ctcgccctcg gccttccgcg ccagccgcag ccacagccgc   240
aacgccaccc gcagccacag ccacagccac agccccaggc atagccttcg gcacagcccc   300

```
ggctccggct cctgcggcag ctcctctggg caccgtccct gcgccgacat cctggaggtt    360
gggatgctct tgtccaaaat caactcgctt gcccacctgc gcgccgcgcc ctgcaacgac    420
ctgcacgcca ccaagctggc gcccggcaag gagaaggagc ccctggagtc gcagtaccag    480
gtgggcccgc tactgggcag cggcggcttc ggctcggtct actcaggcat ccgcgtctcc    540
gacaacttgc cggtggccat caaacacgtg gagaaggacc ggatttccga ctggggagag    600
ctgcctaatg cactcgagt gcccatggaa gtggtcctgc tgaagaaggt gagctcgggt    660
ttctccggcg tcattaggct cctggactgg ttcgagaggc ccgacagttt cgtcctgatc    720
ctggagaggc ccgagccggt gcaagatctc ttcgacttca tcacggaaag gggagccctg    780
caagaggagc tggcccgcag cttcttctgg caggtgctgg aggccgtgcg gcactgccac    840
aactgcgggg tgctccaccg cgacatcaag gacgaaaaca tccttatcga cctcaatcgc    900
ggcgagctca agctcatcga cttcgggtcg ggggcgctgc tcaaggacac cgtctacacg    960
gacttcgatg gacccgagt gtatagccct ccagagtgga tccgctacca tcgctaccat   1020
ggcaggtcgg cggcagtctg gtccctgggg atcctgctgt atgatatggt gtgtggagat   1080
attccttcg agcatgacga agagatcatc agggccagg ttttcttcag gcagagggtc   1140
tcttcagaat gtcagcatct cattagatgg tgcttggccc tgagaccatc agataggcca   1200
accttcgaag aaatccagaa ccatccatgg atgcaagatg ttctcctgcc ccaggaaact   1260
gctgagatcc acctccacag cctgtcgccg gggcccagca atagcagcc tttctggcag   1320
gtcctcccct ctcttgtcag atgcccgagg gaggggaagc ttctgtctcc agcttcccga   1380
gtaccagtga cacgtctcgc caagcaggac agtgcttgat acaggaacaa catttacaac   1440
tcattccaga tcccaggccc ctggaggctg cctcccaaca gtggggaaga gtgactctcc   1500
aggggtccta ggcctcaact cctcccatag atactctctt cttctcatag gtgtccagca   1560
ttgctggact ctgaaatatc ccgggggtgg ggggtgggg tgggtcagaa ccctgccatg   1620
gaactgtttt cttcatcatg agttctgctg aatgccgcga tgggtcaggt aggggggaaa   1680
caggttggga tgggatagga ctagcaccat tttaagtccc tgtcacctct tccgactctt   1740
tctgagtgcc ttctgtgggg actccggctg tgctgggaga aatacttgaa cttgcctctt   1800
ttacctgctg cttctccaaa aatctgcctg ggttttgttc cctatttttc tctcctgtcc   1860
tccctcaccc cctccttcat atgaaaggtg ccatggaaga ggctacaggg ccaaacgctg   1920
agccacctgc ccttttttct gcctccttta gtaaaactcc gagtgaactg gtcttccttt   1980
ttggttttta cttaactgtt tcaaagccaa gacctcacac acacaaaaaa tgcacaaaca   2040
atgcaatcaa cagaaaagct gtaaatgtgt gtacagttgg catggtagta tacaaaaga   2100
ttgtagtgga tctaattttt aagaattttt gcctttaagt tatttttacct gtttttgttt   2160
cttgttttga agatgcgca ttctaacctg gaggtcaatg ttatgtattt atttatttat   2220
ttatttggtt cccttcctat tccaagcttc catagctgct gccctagttt tctttcctcc   2280
tttcctcctc tgacttgggg acctttttggg ggagggctgc gacgcttgct ctgtttgtgg   2340
ggtgacggga ctcaggcggg acagtgctgc agctccctgg cttctgtggg gcccctcacc   2400
tacttacccca ggtgggtccc ggctctgtgg gtgatgggga ggggcattgc tgactgtgta   2460
tataggataa ttatgaaaag cagttctgga tggtgtgcct tccagatcct ctctggggct   2520
gtgttttgag cagcaggtag cctgctggtt ttatctgagt gaaatactgt acaggggaat   2580
aaaagagatc ttatttttt ttttatactt ggcgttttt gaataaaaac cttttgtctt   2640
aaaaaaaaaa aaaaaaaaaa aaaaaaaaaa aaaaaaaaaa aaaa              2684
```